(12) United States Patent
Bonjouklian et al.

(10) Patent No.: US 7,320,995 B2
(45) Date of Patent: Jan. 22, 2008

(54) BENZIMIDAZOLES AND BENZOTHIAZOLES AS INHIBITORS OF MAP KINASE

(75) Inventors: Rosanne Bonjouklian, Zionsville, IN (US); Jose Eugenio De Diego Gomez, Madrid (ES); Alfonso De Dios, Madrid (ES); Chafiq Hamdouchi Hamdouchi, Carmel, IN (US); Tiecho Li, Fishers, IN (US); Beatriz Lopez De Uralde Garmendia, Madrid (ES); Michal Vieth, Carmel, IN (US); Jeremy Schulenberg York, Indianapolis, IN (US); Robert Dean Dally, Indianapolis, IN (US); Miriam Filadelfa Del Prado Catalina, Madrid (ES); Carlos Jaramillo Aguado, Madrid (ES); Luisa Maria Martin-Cabrejas, Madrid (ES); Carlos Montero Salgado, Madrid (ES); Sheila Pleite Selgas, Madrid (ES); Concepcion Sanchez-Martinez, Madrid (ES); Timothy Alan Shepherd, Indianapolis, IN (US); James Howard Wikel, Greenwood, IN (US)

(73) Assignee: Eli Lilly and Company, Indianapolis, IN (US)

( * ) Notice: Subject to any disclaimer, the term of this patent is extended or adjusted under 35 U.S.C. 154(b) by 243 days.

(21) Appl. No.: 10/522,227

(22) PCT Filed: Jul. 31, 2003

(86) PCT No.: PCT/US03/19890

§ 371 (c)(1),
(2), (4) Date: Jan. 25, 2005

(87) PCT Pub. No.: WO2004/014900

PCT Pub. Date: Feb. 19, 2004

(65) Prior Publication Data

US 2005/0272791 A1 Dec. 8, 2005

Related U.S. Application Data

(60) Provisional application No. 60/421,939, filed on Oct. 28, 2002.

(30) Foreign Application Priority Data

Aug. 9, 2002 (EP) .................... 02380178

(51) Int. Cl.
*A61K 31/4184* (2006.01)
*A61K 31/428* (2006.01)
*C07D 277/68* (2006.01)
*C07D 235/10* (2006.01)

(52) U.S. Cl. .................. 514/367; 514/394; 548/152; 548/235; 548/255; 548/302.1; 548/315.1; 548/343.5; 548/364.7; 548/366.1; 548/373.1; 548/379.4

(58) Field of Classification Search ................ 546/199; 548/202, 235, 255, 302.1, 315.1, 343.5, 364.7, 548/366.1, 373.1, 379.4, 152; 514/367, 394
See application file for complete search history.

(56) References Cited

U.S. PATENT DOCUMENTS

| 5,686,455 A | 11/1997 | Adams et al. |
| 5,717,100 A | 2/1998 | Selnick et al. |
| 6,335,336 B1 | 1/2002 | Anantanarayan et al. |
| 6,335,340 B1 | 1/2002 | Gallagher et al. |
| 6,426,360 B1 | 7/2002 | Weier et al. |

FOREIGN PATENT DOCUMENTS

| WO | WO 96 40143 A | 12/1996 |
| WO | WO 97 25045 A | 7/1997 |
| WO | WO 00 10563 A | 3/2000 |
| WO | WO 00 61576 A | 10/2000 |
| WO | WO 01 72737 A1 | 10/2001 |
| WO | WO 02 072576 A | 9/2002 |
| WO | WO03042211 | * 5/2003 |

OTHER PUBLICATIONS

Kai et al., CA125:247806, 1994.*
Wang, Le et al, "Potent Orally Active Heterocycle-Based Combretastatin A-4 Analogues: Synthesis, Structure-Activity Relationship, Pharmacokinetics, and In Vivo Antitumor Activity Evaluation," J. Med. Chem. (45) 2002, pp. 1697-1711.*
Revesz L. et al: "SAR of 4-Hydroxypiperidine and Hydroxyalkyl Substituted Heteroycles as Novel p38 Map Kinase Inhibitors" Bioorganic & Medical Chemistry Letters vol. 10, 2000, pp. 1261-1264, XP002203507.
Le Wang, et al: "Potent, Orally Active Heterocycle-Based Combretastatin A-4 Analogues: Synthesis, Structure—Activity Relationship, Pharmacokinetics, and In Vivo Antitumor Activity Evaluation" J. Med. Chem. 2002, 45, 1697-1711.

* cited by examiner

*Primary Examiner*—Kamal A. Saeed
*Assistant Examiner*—Janet L. Coppins
(74) *Attorney, Agent, or Firm*—Tina M. Tucker; Robert D. Titus; Tonya Combs

(57) ABSTRACT

The present invention provides kinase inhibitors of Formula I: wherein W represents inter alia imidazol, oxazol, pyrazol, thiazol as triazol, which are substituted by phenyl or thienyl. The disclosed compounds inhibit p-38 kinase and are useful in the treatment of metastasis or rheumatoid arthritis

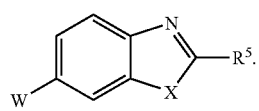

(I)

9 Claims, No Drawings

BENZIMIDAZOLES AND BENZOTHIAZOLES AS INHIBITORS OF MAP KINASE

This application is a United States national phase entry, pursuant to 35 U.S.C. 371, of PCT/US2003/19890, filed Jul. 31, 2003 which claims the benefit of European provisional patent application serial number 2380178.0 filed Sep. 8, 2002, and U.S. provisional patent application Ser. No. 60/421,939 filed Oct. 28, 2002.

BACKGROUND OF THE INVENTION

The p38 kinase is a mitogen-activated protein (MAP) kinase that belongs to the serine/threonine kinase superfamily. This kinase is activated by extracellular stresses such as heat, UV light, and osmotic stress, as well as by inflammatory stimuli such as lipopolysaccharide. When activated, p38 kinase phosphorylates intracellular protein substrates that regulate the biosynthesis of the pro-inflammatory cytokines tumor necrosis factor α (TNF-α) and interleukin-1β (IL-1β). These cytokines are implicated in the pathology of a number of chronic inflammatory disorders (Lee, et al., *Ann. N.Y. Acad. Sci.*, 696, 149-170 (1993); Muller-Ladner, *Curr. Opin. Rheumatol.*, 8, 210-220 (1996)), cardiovascular and central nervous system disorders (Salituro, et al., *Current Medicinal Chemistry*, 6, 807-823 (1999)), and autoimmune disorders (Pargellis, et al., *Nature Structural Biology*, 9(4), 268-272 (2002)).

A number of compounds within the pyridinylimidazole (WO9621452, WO9725045, U.S. Pat. No. 5,656,644, U.S. Pat. No. 5,686,455, U.S. Pat. No. 5,717,100, WO9712876, WO9821957, WO9847892, WO99903837, WO9901449, WO0061576, WO0172737) and pyrimidinyl-imidazole (WO9725048, WO9901452, WO9725046, WO9932121, WO9901131, WO9901130, WO9901136, WO9807452, WO9747618, WO9856788, WO9857996) structural platforms have been identified as inhibitors of p38 kinase or as cytokine inhibitors. Selective inhibitors of p38 kinase are known to suppress the expression of TNF-α and IL-1β (McKenna, et al., *J. Med. Chem.*, 45(11), 2173-2184 (2002)). Anti-inflammatory activity for compounds within the pyrimidinylimidazole structural platform has been reported (Lantos, et al., *J. Med. Chem.*, 27, 72-75 (1984)), and a number of inhibitors of p38 kinase are under active investigation for the treatment of a variety of disorders (Boehm and Adams, *Exp. Opin. Ther. Patents*, 10(1), 25-37 (2000)). There remains a need for treatment in this field for compounds that are cytokine suppressive, i.e., compounds that are capable of inhibiting p38 kinase.

The present invention provides new inhibitors of p38 kinase useful for the treatment of conditions resulting from excessive cytokine production.

BRIEF SUMMARY OF THE INVENTION

The present invention provides compounds of Formula I:

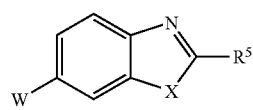

I where:

W is

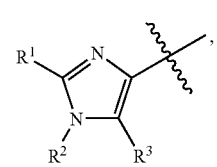
(i)

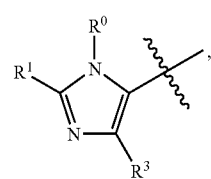
(ii)

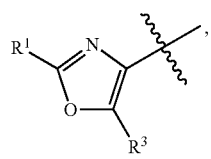
(iii)

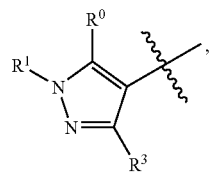
(iv)

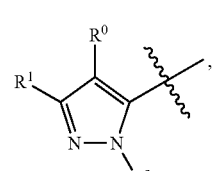
(v)

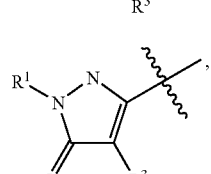
(vi)

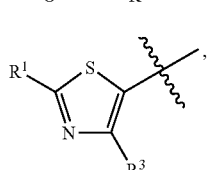
(vii)

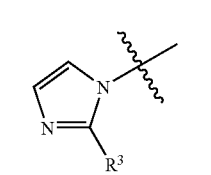
(viii)

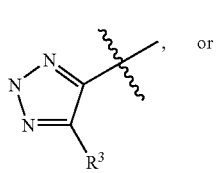
(ix)
or

-continued

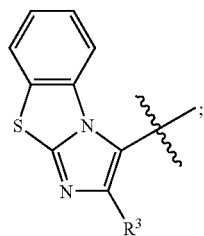
(x)

X is $N(R^4)$ or S;

$R^0$ is (a) selected from the group consisting of hydrogen, $C_1$-$C_6$ alkyl, cyano, ($C_1$-$C_4$ alkylene)-$R^{11}$, 3-hydroxyprop-2-yl, (1-phenyl)-2-hydroxyeth-1-yl, (1-cyclohexyl)-3-hydroxyprop-2-yl, 4-methoxybenzyl, 1,4-dioxoaspiro[4,5]dec-8-yl, tetrahydropyran, 2,2,6,6-tetramethylpiperidin-4-yl, and cyclohexan-1-on-4-yl, (b) phenyl optionally substituted with one substituent selected from the group consisting of nitro and amino, (c) piperidin-4-yl optionally substituted with one substituent selected from the group consisting of $C_1$-$C_4$ alkyl, $C_1$-$C_4$ alkoxycarbonyl, and benzyl, or (d) $C_3$-$C_6$ cycloalkyl optionally substituted with one substituent selected from the group consisting of $C_1$-$C_4$ alkoxycarbonylamino, amino, hydroxy, and $C_1$-$C_4$ alkylene-OH;

$R^1$ is (a) selected from the group consisting of hydrogen, $C_1$-$C_6$ alkyl, $C_2$-$C_4$ alkynyl, halo, amino, azido, formyl, 1-($C_1$-$C_4$ alkoxycarbonyl)ethen-2-yl, 1-($C_1$-$C_4$ alkoxycarbonyl)ethyl, 1-($C_1$-$C_4$ carboxy)ethyl, ($C_1$-$C_4$ alkylene)benzyloxy, trifluoromethyl, trimethylsilylethynyl, but-3-yn-1-ol, $C_3$-$C_6$ cycloalkyl, tetrahydropyran-4-yl, hydroxymethyl, 2-(piperidin-1-yl)methyl, N,N',N'-[trimethyl]-2-(aminoethylamino)methyl, (morpholin-4-yl)methyl, dimethylaminomethyl, N-[2-(piperidin-1-yl)eth-1-yl]-aminomethyl, N',N'-dimethyl-2-(aminoethylamino)methyl, pyridinyl, thiazolyl, triazolyl, benzo(1,3)dioxolan-5-yl, and imidazol-2-yl, (b) phenyl optionally substituted with one to three substituents independently selected from the group consisting of $C_1$-$C_4$ alkyl, halo, nitro, amino, $C_1$-$C_4$ alkoxy, trifluoromethyl, trifluoromethoxy, trifluoromethylsulfanyl, methylsulfonyl, methylsulfonamidyl, pyrrolidin-1-yl, morpholin-4-yl, 4($C_1$-$C_4$ alkyl)piperazin-1-yl, —$NR^6R^7$, and $C_1$-$C_4$ alkoxy optionally substituted with one substituent selected from the group consisting of piperidin-1-yl, pyrrolidin-1-yl, morpholin-4-yl, azepin-4-yl, and di($C_1$-$C_4$ alkyl)amino, (c) thienyl optionally substituted with one substituent selected from the group consisting of halo, nitro, amino, and $C_1$-$C_4$ alkyl, or (d) piperidin-4-yl optionally substituted at the 1-position from the group consisting of $C_1$-$C_4$ alkyl, $C_1$-$C_4$ alkoxycarbonyl, benzyloxycarbonyl, and ($C_1$-$C_4$ alkylene)-$R^8$;

Alternatively $R^0$ and $R^1$ may be taken together to form a fully saturated $C_3$-$C_4$ carbon chain or a fully unsaturated $C_3$-$C_4$ carbon chain optionally substituted with halo or $C_1$-$C_4$ alkyl;

$R^2$ is hydrogen, $C_1$-$C_4$ alkyl, or benzyl;

$R^3$ is thienyl or phenyl optionally substituted with one to two substituents independently selected from the group consisting of halo, $C_1$-$C_4$ alkyl, $C_1$-$C_4$ alkoxy, and trifluoromethyl;

$R^4$ is hydrogen, ($C_1$-$C_4$ alkyl)sulfonyl, or ($C_3$-$C_6$ cycloalkyl)sulfonyl; or ($C_1$-$C_4$ alkyl)$_2$N-sulfonyl;

$R^5$ is halo, hydrogen, or —$NR^9R^{10}$;

$R^6$ and $R^7$ are individually at each occurrence selected from hydrogen, carbonyl, or $C_1$-$C_4$ alkyl providing that at least one of $R^6$ and $R^7$ is hydrogen;

$R^8$ is hydroxy, trifluoromethyl, dimethylamino, phenyl, pyridinyl, or 1-methylimidazol-2-yl;

$R^9$ is independently at each instance hydrogen or $C_1$-$C_4$ alkyl;

$R^{10}$ is hydrogen, $C_1$-$C_4$ alkyl, or benzyl;

$R^{11}$ is $C_1$-$C_4$ alkoxy, hydroxy, $C_1$-$C_4$ alkoxycarbonyl, $C_1$-$C_4$ alkoxycarbonylamino, $C_3$-$C_6$ cycloalkyl, phenyl optionally substituted with one to two substituents independently selected from the group consisting of $C_1$-$C_4$ alkoxy and halo, morpholin-4-yl, or pyridinyl;

provided that when W is

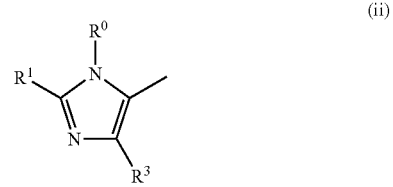
(ii)

then (a) at least one of $R^0$ and $R^1$ is hydrogen or $C_1$-$C_6$ alkyl; or (b) $R^0$ and $R^1$ may be taken together to form a fully saturated $C_3$-$C_4$ carbon chain or a fully unsaturated $C_3$-$C_4$ carbon chain optionally substituted with halo or $C_1$-$C_4$ alkyl;

also provided that when X is S, W is

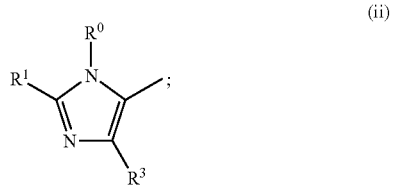
(ii)

or a pharmaceutically acceptable salt or a pharmaceutically acceptable solvate thereof.

The present invention provides a method of inhibiting p-38 kinase in a mammal comprising administering to a mammal in need of such treatment an effective amount of a compound of Formula I or a pharmaceutically acceptable salt or a pharmaceutically acceptable solvate thereof.

The present invention also provides a method of suppressing the production of tumor necrosis factor α (TNF-α) in a mammal comprising administering to a mammal in need of such treatment an effective amount of a compound of Formula I or a pharmaceutically acceptable salt or a pharmaceutically acceptable solvate thereof.

The present invention also provides a method of suppressing the production of interleukin-1β (IL-1β) in a mammal comprising administering to a mammal in need of such treatment an effective amount of a compound of Formula I or a pharmaceutically acceptable salt or a pharmaceutically acceptable solvate thereof.

The present invention further provides a method of treating conditions resulting from excessive cytokine production in a mammal comprising administering to a mammal in need of such treatment a cytokine-suppressing amount of a compound of Formula I or a pharmaceutically acceptable salt or a pharmaceutically acceptable solvate thereof.

The present invention also provides a method of inhibiting the growth of a susceptible neoplasm in a mammal comprising administering to a mammal in need of such treatment a p38 inhibiting amount of a compound of Formula I or a pharmaceutically acceptable salt or a pharmaceutically acceptable solvate thereof.

The present invention also provides a method of inhibiting metastasis in a mammal comprising administering to a mammal in need of such treatment a p38 inhibiting amount of a compound of Formula I or a pharmaceutically acceptable salt or a pharmaceutically acceptable solvate thereof.

The present invention also provides a method of treating rheumatoid arthritis in a mammal comprising administering to a mammal in need of such treatment a p38 inhibiting amount of a compound of Formula I or a pharmaceutically acceptable salt or a pharmaceutically acceptable solvate thereof.

The present invention also provides a pharmaceutical formulation comprising a compound of Formula I or a pharmaceutically acceptable salt or a pharmaceutically acceptable solvate thereof, in combination with a pharmaceutically acceptable carrier, diluent or excipient.

This invention also provides the use of a compound of Formula I or a pharmaceutically acceptable salt or a pharmaceutically acceptable solvate thereof for the manufacture of a medicament for the inhibition of p38 kinase. Additionally, this invention provides a compound of Formula I or a pharmaceutically acceptable salt or a pharmaceutically acceptable solvate thereof for use in the inhibition of p38 kinase in mammals. Furthermore, this invention provides a pharmaceutical composition adapted for the inhibition of p38 kinase comprising a compound of Formula I or a pharmaceutically acceptable salt or a pharmaceutically acceptable solvate thereof in combination with one or more pharmaceutically acceptable excipients, carriers, or diluents.

This invention also provides the use of a compound of Formula I or a pharmaceutically acceptable salt or a pharmaceutically acceptable solvate thereof for the manufacture of a medicament for the suppression of the production of tumor necrosis factor α (TNF-α). Additionally, this invention provides a compound of Formula I or a pharmaceutically acceptable salt or a pharmaceutically acceptable solvate therof for use in the suppression of the production of tumor necrosis factor α (TNF-α) in mammals. Furthermore, this invention provides a pharmaceutical composition adapted for the suppression of the production of tumor necrosis factor α (TNF-α) comprising a compound of Formula I or a pharmaceutically acceptable salt or a pharmaceutically acceptable solvate thereof in combination with one or more pharmaceutically acceptable excipients, carriers, or diluents.

This invention also provides the use of a compound of Formula I or a pharmaceutically acceptable salt or a pharmaceutically acceptable solvate thereof for the manufacture of a medicament for the suppression of the production of interleukin-1β (IL-1β). Additionally, this invention provides a compound of Formula I or a pharmaceutically acceptable salt or a pharmaceutically acceptable solvate thereof for use in the suppression of the production of interleukin-1β (IL-1β) in mammals. Furthermore, this invention provides a pharmaceutical composition adapted for the suppression of the production of interleukin-1β (IL-1β) comprising a compound of Formula I or a pharmaceutically acceptable salt or a pharmaceutically acceptable solvate thereof in combination with one or more pharmaceutically acceptable excipients, carriers, or diluents.

This invention also provides the use of a compound of Formula I or a pharmaceutically acceptable salt or a pharmaceutically acceptable solvate thereof for the manufacture of a medicament for the treatment of conditions resulting from excessive cytokine production. Additionally, this invention provides a compound of Formula I or a pharmaceutically acceptable salt or a pharmaceutically acceptable solvate thereof for use in the treatment of conditions resulting from excessive cytokine production in mammals. Furthermore, this invention provides a pharmaceutical composition adapted for the treatment of conditions resulting from excessive cytokine production comprising a compound of Formula I or a pharmaceutically acceptable salt or a pharmaceutically acceptable solvate thereof in combination with one or more pharmaceutically acceptable excipients, carriers, or diluents.

This invention also provides the use of a compound of Formula I or a pharmaceutically acceptable salt or a pharmaceutically acceptable solvate thereof for the manufacture of a medicament for the inhibition of growth of a susceptible neoplasm. Additionally, this invention provides a compound of Formula I or a pharmaceutically acceptable salt or a pharmaceutically acceptable solvate thereof for use in the inhibition of growth of a susceptible neoplasm in mammals. Furthermore, this invention provides a pharmaceutical composition adapted for the inhibition of growth of a susceptible neoplasm comprising a compound of Formula I or a pharmaceutically acceptable salt or a pharmaceutically acceptable solvate thereof in combination with one or more pharmaceutically acceptable excipients, carriers, or diluents.

This invention also provides the use of a compound of Formula I or a pharmaceutically acceptable salt or a pharmaceutically acceptable solvate thereof for the manufacture of a medicament for the inhibition of metastasis. Additionally, this invention provides a compound of Formula I or a pharmaceutically acceptable salt or a pharmaceutically acceptable solvate thereof for use in the inhibition of metastasis in mammals. Furthermore, this invention provides a pharmaceutical composition adapted for the inhibition of metastasis comprising a compound of Formula I or a pharmaceutically acceptable salt or a pharmaceutically acceptable solvate thereof in combination with one or more pharmaceutically acceptable excipients, carriers, or diluents.

This invention also provides the use of a compound of Formula I or a pharmaceutically acceptable salt or a pharmaceutically acceptable solvate thereof for the manufacture of a medicament for the treatment of rheumatoid arthritis. Additionally, this invention provides a compound of Formula I or a pharmaceutically acceptable salt or a pharmaceutically acceptable solvate thereof for use in the treatment of rheumatoid arthritis in mammals. Furthermore, this invention provides a pharmaceutical composition adapted for the treatment of rheumatoid arthritis comprising a compound of Formula I or a pharmaceutically acceptable salt or a pharmaceutically acceptable solvate thereof in combination with one or more pharmaceutically acceptable excipients, carriers, or diluents.

DETAILED DESCRIPTION OF THE INVENTION

The general chemical terms used in the formulae above have their usual meanings. For example, the term "$C_1$-$C_6$ alkyl" includes methyl, ethyl, propyl, isopropyl, butyl, isobutyl, sec-butyl, tert-butyl, pentyl, and hexyl moieties. The term "$C_1$-$C_4$ alkyl" is included within the meaning of "$C_1$-$C_6$ alkyl" and includes methyl, ethyl, propyl, isopropyl, butyl, isobutyl, sec-butyl, and tert-butyl moieties. The term "$C_1$-$C_4$ alkoxy" is taken to mean a $C_1$-$C_4$ alkyl group linked to the parent molecule through an oxygen atom, and includes the groups methoxy, ethoxy, isopropoxy, and the like. The term "$C_3$-$C_6$ cycloalkyl" includes cyclopropyl, cyclobutyl, cyclopentyl, and cyclohexyl moieties. The term "halo" includes fluoro, chloro, bromo, and iodo.

The term "($C_1$-$C_4$ alkylene)-$R^8$" is taken to mean a linear or branched alkylene chain substituted at any carbon atom with the variable $R^8$ and includes, for example, linear or branched alkyl chains, benzyl, and α-methylbenzyl moieties. Likewise, the term "($C_1$-$C_4$ alkylene)-$R^{12}$" is taken to mean a linear or branched alkylene chain substituted at any carbon atom with the variable $R^{12}$ and includes, for example, linear or branched alkyl chains, benzyl, and α-methylbenzyl moieties.

The term "$C_1$-$C_4$ alkylene-OH" is taken to mean a linear or branched alkylene chain substituted at any carbon atom with a hydroxy group.

The term "1,4-dioxaspiro[4.5]dec-8-yl" is taken to mean the following formula:

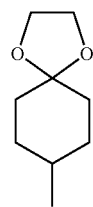

The term "fully saturated $C_3$-$C_4$ carbon chain" is taken to mean a chain of 3 or 4 methylene groups. The phrase "fully unsaturated $C_3$-$C_4$ carbon chain" is taken to mean a 3-carbon chain containing one carbon-carbon double bond or a 4-carbon chain containing two carbon-carbon double bonds.

The term "p-38 kinase" is taken to mean the p-38α and/or p-38β kinase isoforms.

The term "suppressing the production of TNF-α (IL-1β, cytokine)" is taken to mean decreasing excessive in vivo levels of TNF-α, IL-1β, or another cytokine in a mammal to normal or sub-normal levels. This may be accomplished by inhibition of the in vivo release of TNF-α, IL-1β, or another cytokine by all cells, including macrophages; by down regulation, at the genomic level, of excessive in vivo levels of TNF-α, IL-1β, or another cytokine in a mammal to normal or sub-normal levels; by inhibition of the synthesis of TNF-α, IL-1β, or another cytokine as a posttranslational event; or by a down regulation of TNF-α, IL-1β, or another cytokine at the transcriptional or translational level.

The skilled artisan will appreciate that certain compounds of Formula I contain at least one chiral center. The present invention contemplates all individual enantiomers or diastereomers, as well as mixtures of the enantiomers and diastereomers of said compounds including racemates. It is preferred that compounds of Formula I containing at least one chiral center exist as single enantiomers or diastereomers. The single enantiomers or diastereomers may be prepared beginning with chiral reagents or by stereoselective or stereospecific synthetic techniques. Alternatively, the single enantiomers or diastereomers may be isolated from mixtures by standard chiral chromatographic or crystallization techniques. The skilled artisan will also appreciate that the compounds of the present invention may exist as tautomers. The present invention contemplates all tautomeric forms.

Furthermore, certain compounds of Formula I may exist as the geometric cis- and trans-isomers. The present invention contemplates all individual geometric isomers as well as mixtures of the geometric isomers of said compounds. It is preferred that compounds of Formula I exist as single geometric isomers. The individual isomers may be prepared selectively by methods known to the skilled artisan, or mixtures of the isomers may be separated by standard chromatographic or crystallization techniques.

It will be understood by the skilled reader that most or all of the compounds of the present invention are capable of forming salts. In all cases, the pharmaceutically acceptable salts of all of the compounds are included in the names of them. The compounds of the present invention are amines, and accordingly react with any of a number of inorganic and organic acids to form pharmaceutically acceptable acid addition salts. Preferred pharmaceutically acceptable salts are those formed with hydrochloric acid, maleic acid, or methanesulfonic acid.

It will also be understood by the skilled reader that pharmaceutically acceptable solvates of compounds of Formula I are contemplated as part of this invention and may be prepared by conventional methods such as dissolving the compounds of Formula I in solvents such as water, methanol, ethanol, etc., and recrystallizing by using different crystallization techniques.

While all of the compounds of Formula I are useful inhibitors of p-38 kinase, certain classes of compounds are preferred. The following paragraphs describe such preferred classes:
a) $R^0$ is hydrogen;
b) $R^0$ is methyl;
c) $R^0$ is cyclopropyl;
d) $R^0$ is cyclohexyl;
e) $R^1$ is phenyl optionally substituted with one or two substituents individually selected from the group consisting of halo and trifluoromethyl;
f) $R^1$ is phenyl substituted with chloro;
g) $R^1$ is phenyl substituted with two chloros;
h) $R^1$ is phenyl substituted with two fluoros;
i) $R^1$ is phenyl substituted with fluoro and chloro;
j) $R^1$ is phenyl substituted with trifluoromethyl;
k) $R^1$ is 4-chlorophenyl;
l) $R^1$ is 2,6-dichlorophenyl;
m) $R^1$ is 2,6-difluorophenyl;
n) $R^1$ is 2-chloro-6-fluorophenyl;
o) $R^1$ is 2-fluoro-6-trifluoromethyl;
p) $R^1$ is methyl;
q) $R^1$ is ethyl;
r) $R^1$ is tert-butyl;
s) $R^1$ is isopropyl;
t) $R^1$ is 2,2-dimethylpropyl;
u) $R^1$ is cyclopropyl;
v) $R^1$ is cyclohexyl;
w) $R^1$ is hydrogen;
x) $R^2$ is hydrogen;
y) $R^3$ is phenyl;
z) $R^3$ is phenyl substituted with one fluoro;
aa) $R^3$ is phenyl substituted with two fluoros;
bb) $R^3$ is 4-fluorophenyl;
cc) $R^3$ is 2,4-difluorophenyl;
dd) $R^4$ is ($C_1$-$C_4$ alkyl)sulfonyl;
ee) $R^4$ is isopropylsulfonyl;
ff) $R^4$ is tert-butylsulfonyl;
gg) $R^4$ is ($C_3$-$C_6$ cycloalkyl)sulfonyl;
hh) $R^4$ is cyclopentylsulfonyl;
ii) $R^4$ is cyclohexylsulfonyl;
jj) $R^4$ is dimethylaminosulfonyl;
kk) $R^5$ is $NR^9R^{10}$;
ll) $R^5$ is —$NH_2$;
mm) $R^5$ is hydrogen;
nn) W is

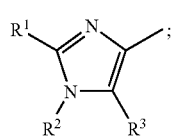
(i)

oo) W is

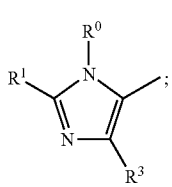
(ii)

pp) W is

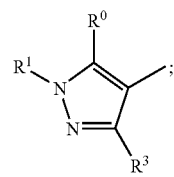
(iv)

qq) W is

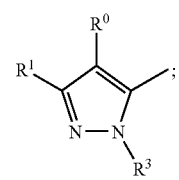
(v)

rr) X is $N(R^4)$;
ss) X is N(isopropylsulfonyl), $R^5$ is $NH_2$, W is

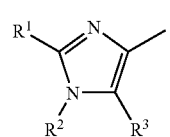
(i)

or

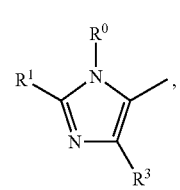
(ii)

$R^3$ is phenyl, and $R^1$ is phenyl optionally substituted with one to two halos or $C_1$-$C_4$ alkyl;
tt) the compound of Formula I is a free base;
uu) the compound of Formula I is a solvate;
vv) the compound of Formula I is a pharmaceutically acceptable salt;
ww) the compound of Formula I is the hydrochloride salt;
xx) the compound of Formula I is the napadysilate salt;
yy) the compound of Formula I is the dimaleate salt;
zz) the compound of Formula I is the methanesulfonate salt.

Preferred embodiments of the present invention include all combinations of a)-zz).

The compounds of Formula I are inhibitors of p38 kinase. Thus, the present invention also provides a method of inhibiting p38 kinase in a mammal that comprises administering to a mammal in need of said treatment a p38 kinase-inhibiting amount of a compound of Formula I. It is preferred that the mammal to be treated by the administration of the compounds of Formula I is human.

As inhibitors of p38 kinase, the compounds of the present invention are useful for suppressing the production of the pro-inflammatory cytokines, tumor necrosis factor α (TNF-α) and interleukin-1β (IL-1β), and therefore for the treatment of disorders resulting from excessive cytokine production. The present compounds are therefore useful in treating inflammatory disorders, including eczema, atopic dermatitis, rheumatoid arthritis, osteoarthritis, inflammatory bowel disease, and toxic shock syndrome. The compounds of the present invention are also believed to be useful in the treatment of cardiovascular disorders, such as acute myocardial infarction, chronic heart failure, atherosclerosis, viral myocarditis, cardiac allograft rejection, and sepsis-associated cardiac dysfunction. Furthermore, the compounds of the present invention are also useful for the treatment of central nervous system disorders, such as meningococcal meningitis, Alzheimer's disease, Parkinson's disease, and multiple sclerosis.

Most solid tumors increase in mass through the proliferation of malignant cells and stromal cells, including endothelial cells. In order for a tumor to grow larger than 2-3 millimeters in diameter, it must form a vasculature, a process known as angiogenesis. Suppression of tumor-induced angiogenesis by angiostatin and endostatin has been reported to result in antitumor activity (O'Reilly, et al., *Cell*, 88, 277-285 (1997)). The selective p38 kinase inhibitor SB22025 has been shown to inhibit angiogenesis (J. R. Jackson, et al., *J. Pharmacol. Exp. Therapeutics*, 284, 687 (1998)). Because angiogenesis is a critical component of the mass expansion of most solid tumors, the development of new p38 kinase inhibitors for the inhibition of this process represents a promising approach for antitumor therapy. This approach to antitumor therapy may lack the toxic side effects or drug resistance-inducing properties of conventional chemotherapy (Judah Folkman, *Endogenous Inhibitors of Angiogenesis*, The Harvey Lectures, Series 92, pages 65-82, Wiley-Liss Inc., (1998)).

As inhibitors of p38 kinase, the compounds of the present invention, therefore, are also useful in inhibiting growth of susceptible neoplasms. Schultz, R. M. *Potential of p38 MAP kinase inhibitors in the treatment of cancer*. In: E. Jucker (ed.), *Progress in Drug Research*, 60, 59-92, (2003). A susceptible neoplasm is defined to be a neoplasm that depends upon p38 kinase for its survival, growth, or metastasis. Susceptible neoplasms include tumors of the brain, genitourinary tract, lymphatic system, stomach, larynx, and lung (U.S. Pat. No. 5,717,100). Preferably, the term "susceptible neoplasms" as used in the present application includes human cancers including non-small cell lung carcinoma (A. Greenberg, et al., *Am. J. Respir. Cell Mol. Biol.*, 26, 558 (2002)), breast carcinoma (J. Chen, et al., *J. Biol. Chem.*, 276, 47901 (2001); B. Salh, et al., *Int. J. Cancer*, 98, 148 (2002); and S. Xiong, et al., *Cancer Res.*, 61, 1727 (2001)), gastric carcinoma (Y. D. Jung, et al., *Proc. Am. Assoc. Cancer Res.*, 43, 9 (2002)), colorectal carcinomas (S. Xiong, et al., *Cancer Res.*, 61, 1727 (2001)), and malignant melanoma (C. Denkert, et al., *Clin. Exp. Metastasis*, 19, 79 (2002)).

Inhibition of angiogenesis by suppression of TNF-α has also been taught to be useful in the inhibition or prevention of metastasis (U.S. Pat. No. 6,414,150; U.S. Pat. No. 6,335,336). Furthermore, suppression of TNF-α is indicated for the treatment and prevention of cachexia, a wasting syndrome experienced by about half of all cancer patients (T. Yoneda, et al., *J. Clin. Invest.*, 87, 977 (1991)).

Furthermore, inhibition of p38 kinase may be effective in the treatment of certain viral conditions such as influenza (K. Kujime, et al., *J. Immunology.*, 164, 3222-3228 (2000)), rhinovirus (S. Griego, et al., *J. Immunology*, 165, 5211-5220 (2000)), and HIV (L. Shapiro, et al., *Proc. Natl. Acad. Sci. USA*, 95, 7422-7426, (1998)).

Compounds of Formula I where W is imidazole (i) or (ii) and $R^5$ is $-NH_2$ may be prepared as illustrated in the following scheme where "TBS" is defined to be tert-butyldimethylsilyl and all other variables are as previously defined. In the following scheme, only W=imidazole (i) is illustrated. This is not intended to limit the scope in any way.

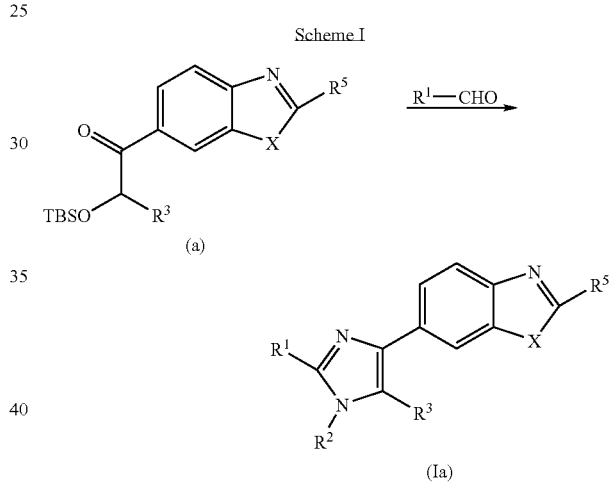

A mixture of the α-ketosilylether (a) is heated with an appropriate aldehyde in the presence of copper(II) acetate and ammonium acetate in a suitable solvent, typically acetic acid. The acid is neutralized and the desired imidazole (Ia) isolated by standard extractive and chromatographic techniques.

The requisite α-ketosilylether (a) may be prepared as described in the following scheme where "TBS" is defined to be tert-butyldimethylsilyl, $R^5$ is $-NH_2$, and all other variables are as previously defined.

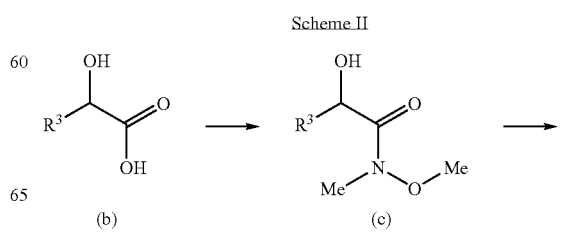

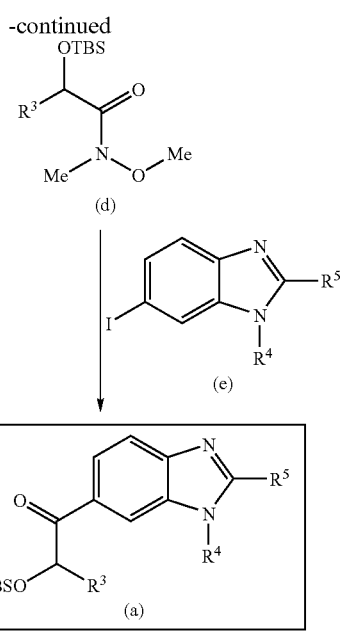

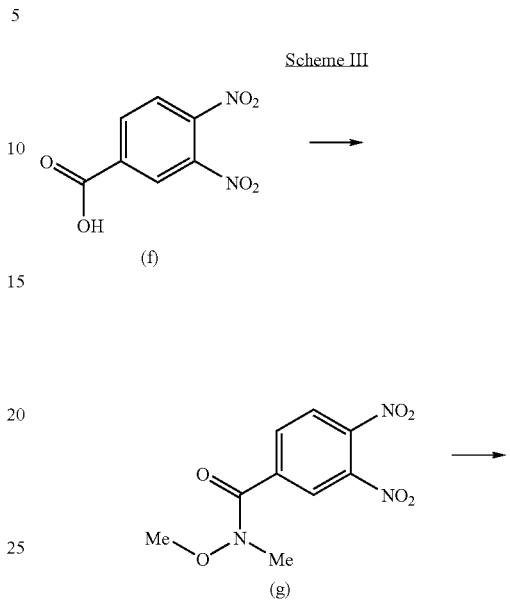

Scheme III

An appropriate α-hydroxyacid (b) is converted to the corresponding Weinreb amide (c) under standard conditions. Briefly, the α-hydroxyacid (b) is converted to the corresponding methyl ester and this ester is then reacted with N-methyl-O-methylhydroxylamine hydrochloride in the presence of trimethylaluminum in an appropriate solvent. The α-hydroxyamide (c) is then treated with tert-butyldimethylsilyl triflate in the presence of base under standard conditions to provide the α-silylether amide (d) (Tius, et al. (*Tetrahedron*, 56, 3339-3351 (2000)). Compound (d) is then coupled with 6-iodobenzimidazole or 6-iodobenzothiazole (e) in the presence of isopropylmagnesium chloride to provide the desired compound (a). The requisite iodobenzimidazole (e) may be prepared from 2-aminobenzimidazole as described by Mitchell, et al. (*Journal of Organic Chemistry*, 63, 5050-5058 (1998)).

Alternatively, 3,4-dinitrobenzoic acid (f) may be converted to the corresponding Weinreb amide (g) by converting the benzoic acid to the corresponding benzoyl halide, preferably by reaction with oxalyl chloride, and then reacting the benzoyl chloride with N-methyl-O-methylhydroxylamine in the presence of a suitable base, typically pyridine, to provide the corresponding amide. The amide (g) is then subjected to catalytic hydrogenation conditions to provide the corresponding diamine that is then treated with an appropriate sulfonyl halide in the presence of a base, typically pyridine, to provide the corresponding sulfonamide (h). This sulfonamide is first treated with base and then reacted with cyanogen bromide in a suitable solvent to provide the aminobenzimidazole (j). The aminobenzimidazole (j) is reacted with the anion generated from the silyl ether (k) and tert-butyllithium to provide the desired intermediate (a). The requisite silyl ether may be prepared from the corresponding alcohol under standard conditions (see, Greene, et al., *Protective Groups in Organic Synthesis*, John Wiley and Sons Ed., 1981).

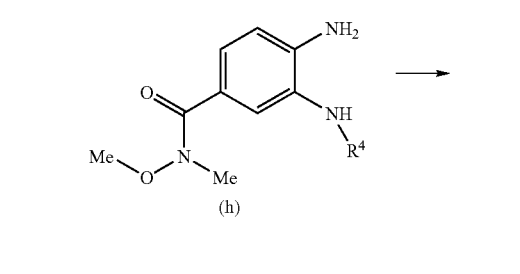

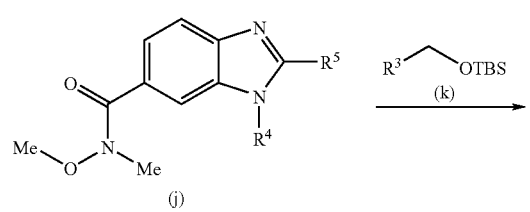

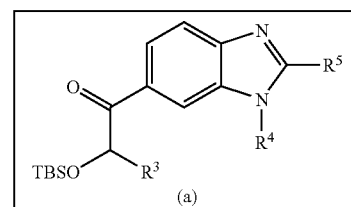

Alternatively, compounds of Formula I where W is the imidazole (i) may be prepared as illustrated in the following scheme where $R^5$ is —$NH_2$, $R^2$ is hydrogen, and all other variables are as previously defined.

Scheme IV

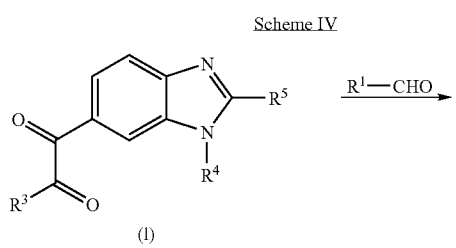

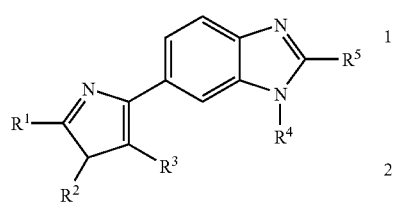

Diketone (l) is reacted with ammonium acetate and an appropriate aldehyde in an appropriate solvent, preferably acetic acid, to provide the corresponding imidazolyl benzimidazole or imidazolyl benzothiazole. The requisite diketones (l) may be prepared as described in the following scheme, where all variables are as previously defined.

Scheme V

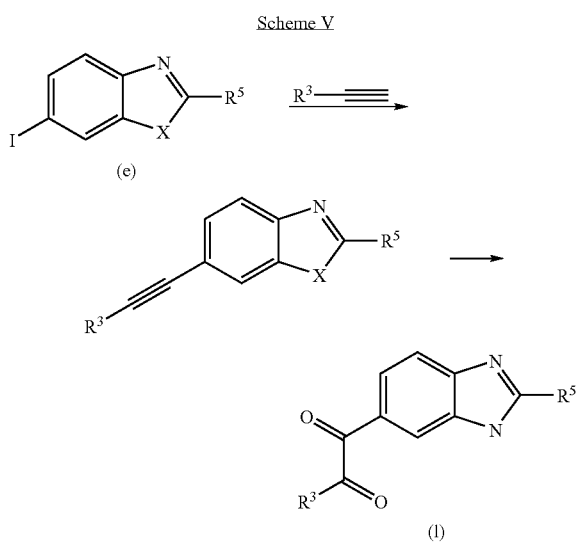

The appropriate alkynyl is coupled with 6-iodobenzimidazole or 6-iodobenzothiazole (e) and then oxidized to provide the desired diketone compound (l) by the method of Khan, et al. (*JOC*, 17, 1063-1065 (1952)).

Alternatively, the desired diketone compound may be prepared starting from α-ketosilylether (a), hydrolyzing the silyl group followed by oxidation.

Compounds of Formula I where W is imidazole (ii) may be prepared as described in the following scheme where $R^5$ is —$NH_2$ and all other variables are as previously defined.

Scheme VI

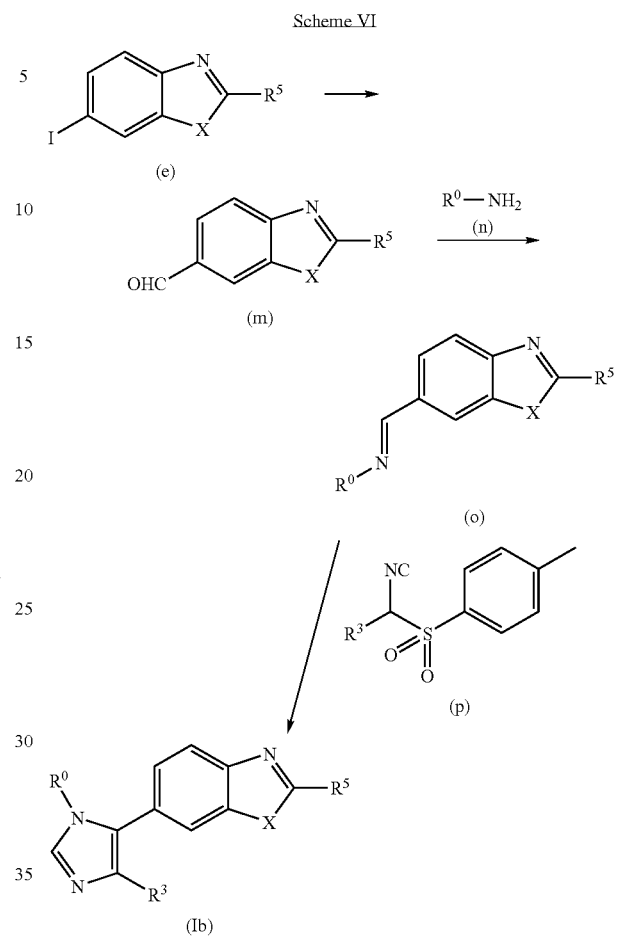

React the heteroaryl iodide (e) with phenyllithium followed by tert-butyllithium at low temperature. The dianion is quenched with dimethylformamide and the corresponding aldehyde (m) is isolated under standard conditions. This aldehyde is then reacted with an appropriate amine (n) in a suitable solvent, typically dimethylformamide, to form the corresponding imine (o). This imine is then reacted with an appropriately substituted p-toluenesulfonylmethyl isocyanate (p) in methanol with a primary alkyl amine at reflux to provide the desired compound (Ib). The requisite amines (n) are either commercially available or may be prepared by methods well known to the skilled artisan. The requisite p-toluenesulfonylmethyl isocyanates (p) may be prepared as described in the following scheme where all variables are as previously defined.

Scheme VII

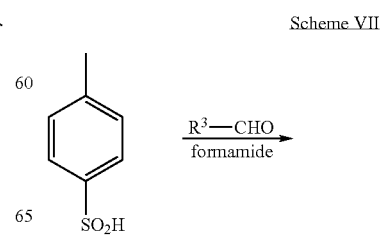

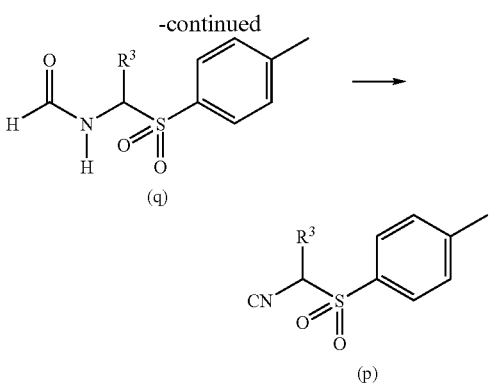

A mixture of p-toluenesulfinic acid, formamide, and an appropriate aldehyde are combined and heated together in the presence of a suitable acid to provide the N-formyl p-toluenesulfonylmethylamine (q). The intermediate (q) is reacted with a suitable dehydrating agent, typically phosphorus oxychloride, to provide the isocyanide (p). The requisite aldehydes are either commercially available or may be prepared by standard methods well known in the art.

Compounds of Formula I where W is a thiazole (vii) may be prepared as illustrated in the following scheme where $R^5$ is —$NH_2$ and all other variables are as previously defined.

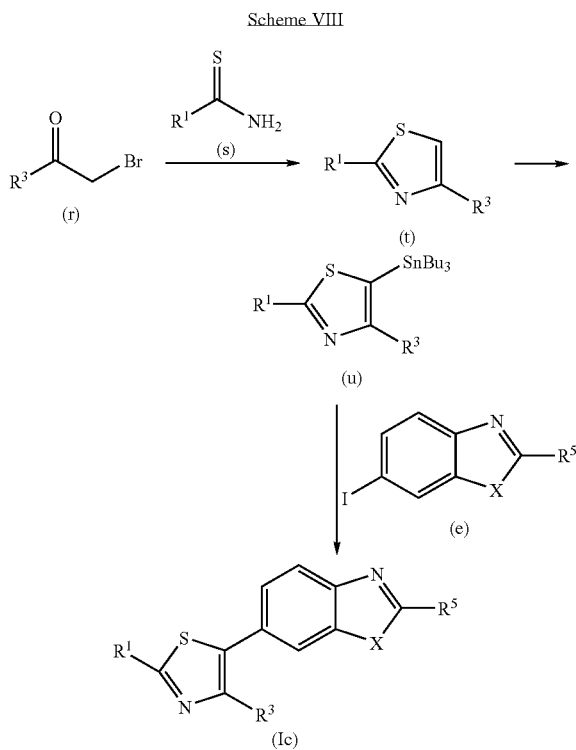

An appropriate α-haloketone (r) is reacted with an appropriate thioamide (s) in a suitable solvent to provide thiazole (t). This thiazole is treated n-butyllithium and the resulting anion is reacted with tributyltin chloride to provide the tin derivative (u). This intermediate is coupled with 1-(isopropylsulfonyl)-2-amino-6-iodobenzimidazole or 2-amino-6-iodobenzothiazole (e) in the presence of a palladium catalyst under standard conditions to provide the desired compound (Ic).

The requisite α-haloketones are either commercially available or may be prepared by standard conditions from the corresponding carbonyl compound, for example, as described by House (H. O. House, *Modern Synthetic Reactions*, W. A. Benjamin, Inc., Menlo Park, Calif. (1972), pages 459-478) and Larock (R. C. Larock, *Comprehensive Organic Transformations*, VCH Publishers, Inc., New York, N.Y. (1989), pages 369-471, 755). The requisite thioamides are either commercially available or may be prepared by standard methods well known to the skilled artisan, for example, by treatment of an appropriate amide with [2,4-bis(4-methoxyphenyl)-1,3-dithia-2,4-diphosphetane-2,4-disulfide] (Lawesson's Reagent).

Compounds of Formula I where W is the pyrazole (v) may be prepared as illustrated in the following scheme where $R^5$ is —$NH_2$ and all other variables are as previously defined.

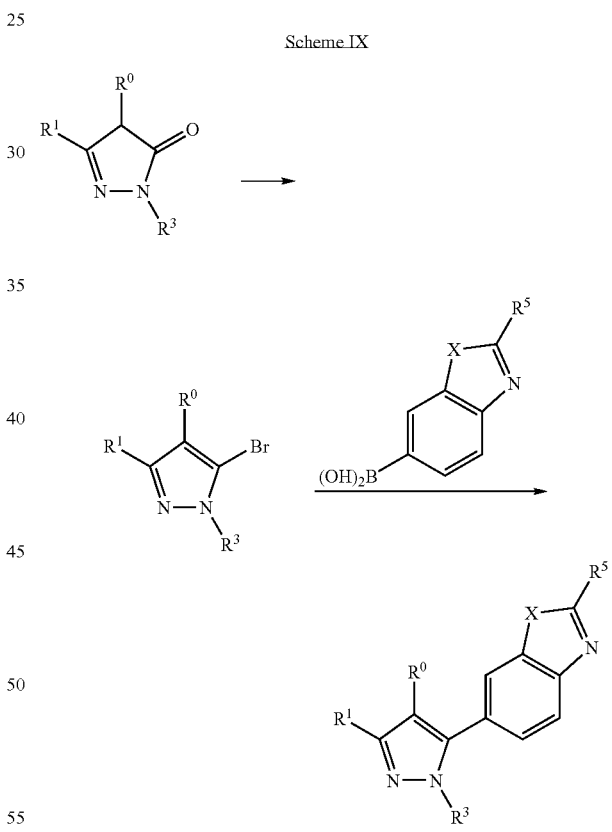

The appropriate pyrazol-5-one is brominated with an appropriate brominating agent such as phosphorus oxybromide to obtain the appropriate 5-bromo-1H-pyrazole. The pyrazole is then coupled with the appropriate benzimidazole 6-boronic acid to arrive at the appropriate pyrazolyl benzimidazole.

Alternatively, compounds where W=(iv) may be prepared as illustrated in the following scheme where $R^5$ is —$NH_2$ and all other variables are as previously defined.

Scheme X

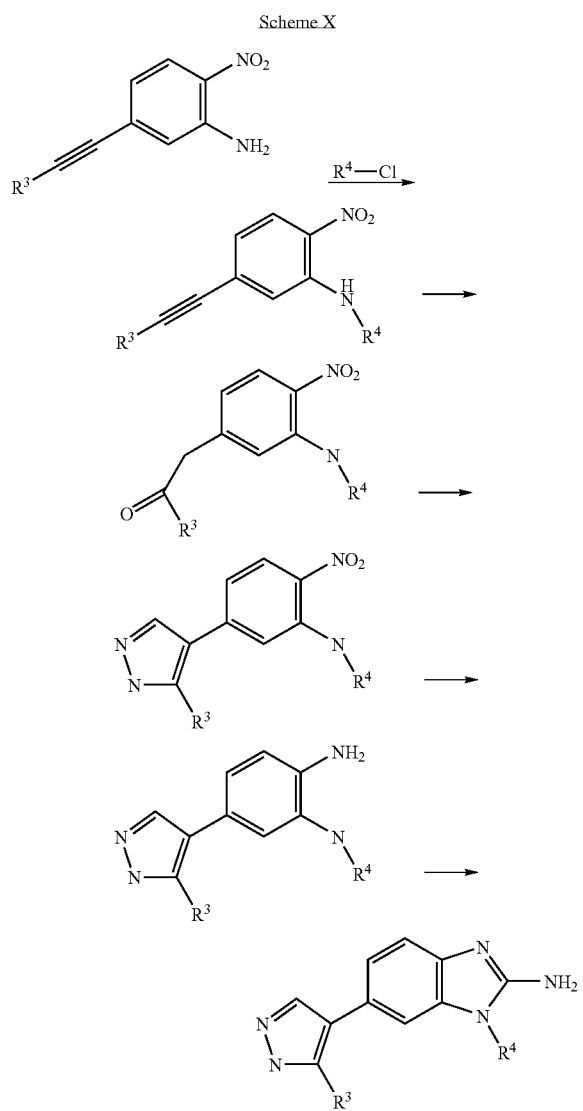

An appropriate alkynyl is coupled with a suitable chloride compound and then oxidized to form the ketone. The ketone is reacted with anhydrous hydrazine and an appropriate aldehyde in an appropriate solvent to form the pyrazole. The nitro group is reduced and ring closure is effected to arrive at the appropriate pyrazolyl benzamidazole.

Compounds of Formula I where W is the pyrazolone (vi) may be prepared as illustrated in the following scheme where R⁵ is —NH₂ and all other variables are as previously defined.

Scheme XI

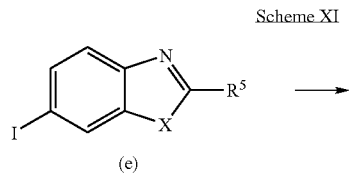

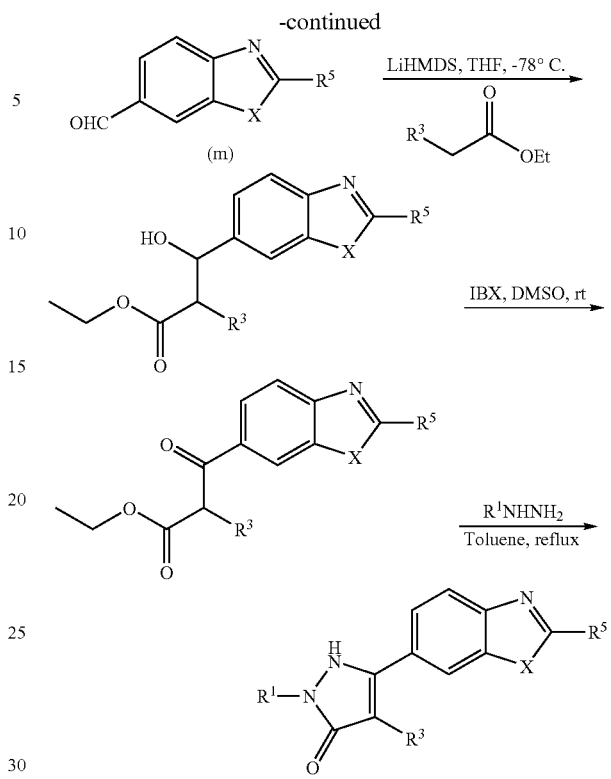

The dianion of 6-iodobenzimidazole (e) is prepared by sequential treatment with phenyllithium followed by tert-butyllithium at low temperature. The dianion is quenched with dimethylformamide and the corresponding aldehyde (m) is isolated under standard conditions. This aldehyde is then reacted with an appropriate ethyl acetate followed by oxadation to obtain the diketobenzamidazole. The diketobenzimidazole is reacted with the appropriate hydrazine compound and refluxed in the presence of toluene to obtain the desired pyrazolone benzimidazole.

Compounds of Formula I where W is an imidazole (viii) and X=N(R⁴) may be prepared as illustrated in the following scheme where all variables are as previously defined. Please note that that the 2-phenyl attached to the imidazole is shown unsubstituted, but may in fact be substituted.

Scheme XII

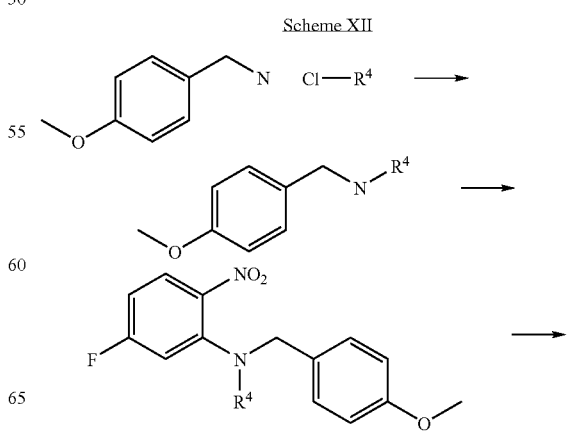

-continued

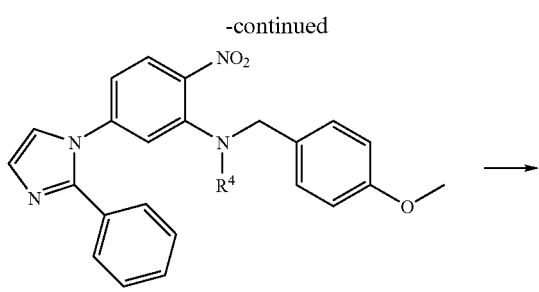

Parametoxy-benzylmethylamine is coupled with an appropriate sulfonyl chloride, The amine is then protected and the resulting compound coupled with 2-phenyl imidazol-3-yl. The amine is deprotected and benzimidazole constructed as in Scheme III.

Compounds of Formula I where W is a triazole (ix) may be prepared as illustrated in the following scheme where $R^5$ is $-NH_2$ and ll variables are as previously defined.

Scheme XIII

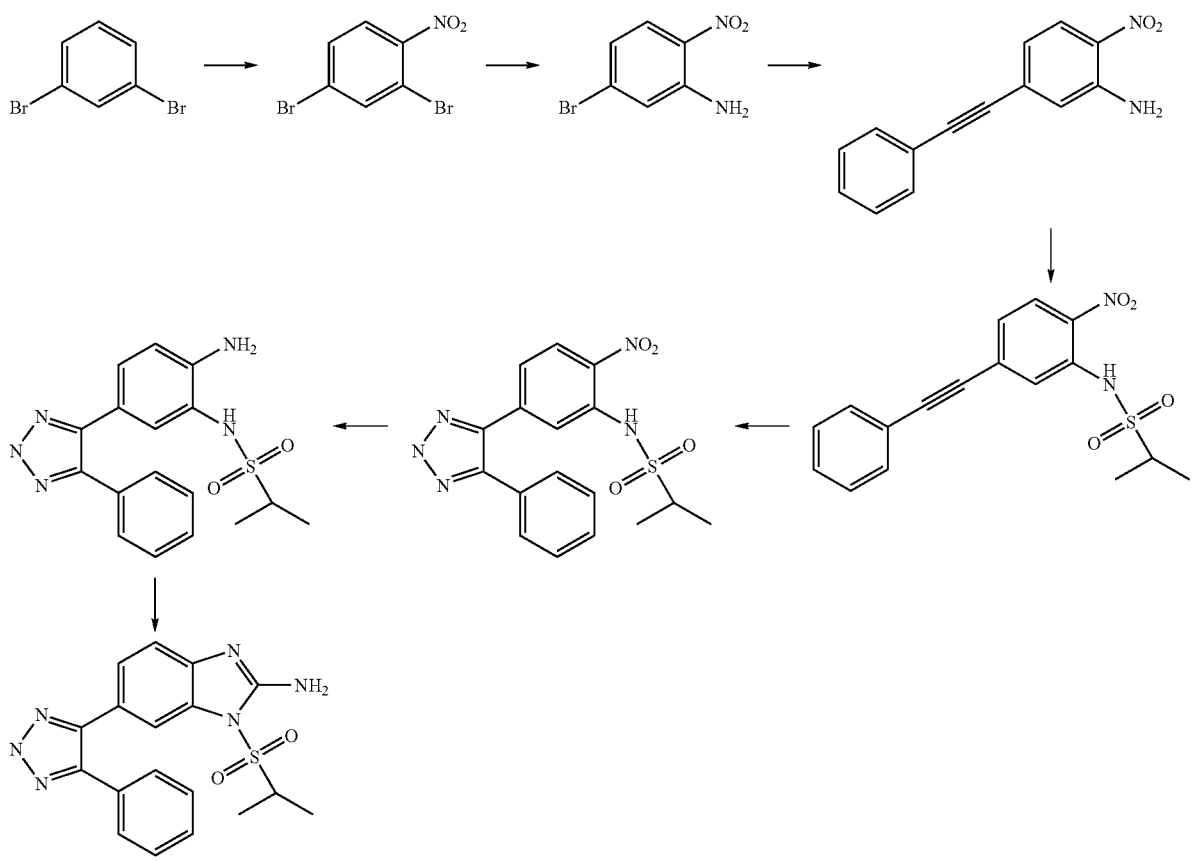

-continued

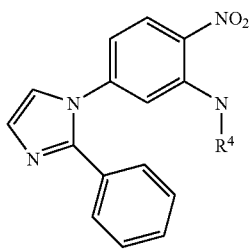

The dibromobenzene is nitrated followed by amination. The resulting nitroaniline is then coupled with an appropriate phenylacetylene to provide the corresponding diphenylacetylene The sulfonamide is formed by addition of an appropriate sulfonyl halide and the triazole is formed by addition of a source of azide, typically sodium azide. The benzimidazole is then prepared as previously described.

Many of the compounds of the present invention are not only inhibitors of p38 kinase, but are also useful intermediates for the preparation of additional compounds of the present invention. For example, primary and secondary amines may be acylated, alkylated or coupled with carboxylic acids or amino acids under standard peptide coupling conditions. Furthermore, ester moieties may be reduced to the corresponding alcohols or converted to amides under standard conditions. Alcohols may be activated and displaced by a number of nucleophiles to provide other compounds of the invention. Such leaving groups include but are not limited to halides, oxonium ions, alkyl perchlorates, ammonioalkanesulfonate esters, alkyl fluorosulfonates, nonaflates, tresylates, triflates, and sulfonic esters, preferably the methane sulfonate or tosylate. Techniques for the introduction of these groups are also well known to the skilled artisan; see, for example, March, *Advanced Organic Chemistry*, 5th Ed., John Wiley and Sons, New York, pg. 445-449 (2001). Additionally, the 2-amino moiety of the benzimidazole nucleus may be diazotized and displaced to provide the corresponding halo deriviatives under standard conditions. These compounds may then be reacted with a variety of amines under standard conditions to provide additional compounds of Formula I. Furthermore, the diazoammonium compounds may be reduced to provide the corresponding unsubstituted compounds.

The skilled artisan will also appreciate that not all of the substituents in the compounds of Formula I will tolerate certain reaction conditions employed to synthesize the compounds. These moieties may be introduced at a convenient point in the synthesis, or may be protected and then deprotected as necessary or desired. The skilled artisan will appreciate that the protecting groups may be removed at any convenient point in the synthesis of the compounds of the present invention. Methods for introducing and removing nitrogen and oxygen protecting groups are well known in the art; see, for example, Greene and Wuts, *Protective Groups in Organic Synthesis*, 3rd Ed., John Wiley and Sons, New York, Chapter 7 (1999). Furthermore, the skilled artisan will appreciate that in many circumstances, the order in which moieties are introduced is not critical. The particular order of steps required to produce the compounds of Formula I is dependent upon the particular compound being synthesized, the starting compound, and the relative lability of the substituted moieties.

Preparation 1

1-isopropylsulfonyl-2-amino-6-formylbenzimidazole

Add phenyllithium (750 mL, 1.8 M in cyclohexane/ether, 70/30) over 1 hour to a solution of 1-isopropylsulfonyl-2-amino-6-iodobenzimidazole (150 g, 0.41 mol) in tetra-hydrofuran (5.6 L) at −76° C. Stir for 15 minutes and then add tert-butyllithium (750 ml, 1.7 M in pentane). After 1 hour add dimethylformamide (250 mL) slowly over one hour and then warm to 0° C. Quench by pouring the reaction mixture into a mixture of cold saturated aqueous ammonium chloride (500 g, 5 L) and concentrated hydrochloric acid (300 mL). Separate the layers, wash the organic phase with water and then concentrate under reduced pressure. Slurry the residue in methanol (500 mL), filter the yellow precipitate, and dry to provide 85 g (76%) of the title compound.

$^1$H-NMR (DMSO-$d_6$): § 9.89 (s, 1H), 7.97 (s, 1H), 7.76 (d, 1), 7.43 (s, 2H ), 7.37(d, 1H), 3.98 (m, 1H), 1.35 (m, 6H).

Preparation 2

α-(p-toluenesulfonyl)benzylisocyanide

Step A. N-[formyl] α-(p-toluenesulfonyl)benzylamine

Method A.

Add concentrated hydrochloric acid (3 mL) dropwise to a solution of p-toluene-sulfinic acid sodium salt in water (20 mL) and tert-butyl methyl ether (10 mL). Stir for 10 minutes and then separate the layers. Wash the organic layer with saturated aqueous sodium chloride, dry over sodium sulfate and concentrate under reduced pressure to provide 5 g of p-toluenesulfinic acid. Combine this acid with benzaldehyde (4.75 g, 44.8 mmol), formamide (4.9 g, 0.11 mol), and camphorsulfonic acid (0.86 g, 3.7 mmol) and heat to 60° C. for 18 hours. Remove the reaction from the heat and slurry the white solid in 3:1 hexanes:methanol. Filter the slurry to provide 7.6 g (82%) of the desired product as a white solid. $^1$H-NMR (DMSO-$d_6$): § 9.75 (d, 1H), 7.98 (s, 1H), 7.69 (d, 2H), 7.53 (d 2H), 7.39 (m, 5H), 6.36 (d, 1H), 2.38 (s, 1H).

Method B.

Treat a solution of p-toluenesulfinic acid sodium salt, (6.0 g, 33.7 mmol) in $H_2O$ (20 mL) and tert-butyl methyl ether (10 mL) dropwise with concentrated HCl (3 mL) and stir for 10 minutes. Separate the solution in a separatory funnel and wash the organic layer with saturated aqueous sodium chloride. Dry the organic over $Na_2SO_4$, filter, and remove the solvent to afford 5.2 g (quantitative) of p-toluenesulfinic acid. Combine the acid with benzaldehyde (2.4 g, 22.5 mmol), formamide (3.8 g, 84.2 mmol), and trimethylsilylchloride (TMSCl) (4.0 g, 37.0 mmol) in 30 mL of a 1:1 solution of toluene/acetonitrile. Heat the reaction to 50° C. and stir for 5 hours. Cool the reaction and dilute in $H_2O$ (100 mL) and tert-butyl-methylether (TBME) (30 mL). Cool the solution in an ice bath, then filter to afford 4.5 g (70%) of desired product. Dry the solid under vacuum overnight to remove any residual water. $^1$H-NMR (DMSO): 9.75 (d, 1H), 7.98 (s, 1H), 7.69 (d, 21), 7.53 (d, 2H), 7.39 (m, 5H), 6.36 (d, 1H), 2.38 (s, 1H)

Step B. Dehydration

Cool a solution of N-[formyl] α-(p-toluenesulfonyl)benzylamine (7.0 g, 0.024 mol) in dimethoxyethane (200 mL) to −10° C. Add phosphorus oxychloride (5.6 mL, 0.06 mol) followed by the dropwise addition of triethylamine (16.8 mL, 0.12 mol) in dimethoxyethane (10 mL) maintaining a reaction temperature below −5° C. Warm the reaction mixture gradually over 1 hour, add water and extract with ethyl acetate. Separate the layers, wash the organic phase with saturated aqueous sodium bicarbonate, dry over sodium sulfate, and concentrate under reduced pressure to provide 6.5 g of the title compound. MS(ES[31]): m/z=270.1 (M−H)$^-$ The compounds of Preparations 3-4 are prepared essentially as described in Preparation 2 using method A in the first step.

| Prep. | Compound | MS(ES⁻): m/z = |
|---|---|---|
| 3 | α-(p-toluenesulfonyl)-4-fluorobenzylisocyanide | 288.1 (M − H)⁻ |
| 4 | α-(p-toluenesulfonyl)-α-(thien-3-yl)methylisocyanide | 276.0 (M − H)⁻ |

The compounds of Preparations 5-8 are prepared essentially as described in Preparation 2 using method B in the first step.

| Prep. | Compound | MS (ES⁻): m/z = |
|---|---|---|
| 5 | α-(p-toluenesulfonyl)-3-fluorobenzylisocyanide | 288.2 (M − H)⁻ |
| 6 | α-(p-toluenesulfonyl)-2-fluorobenzylisocyanide | 288.2 (M − H)⁻ |
| 7 | α-(p-toluenesulfonyl)-2,4-difluorobenzylisocyanide | 306.3 (M − H)⁻ |
| 8 | α-(p-toluenesulfonyl)-2,3-difluorobenzylisocyanide | 306.3 (M − H)⁻ |

Preparation 9

N-[1-(ethoxycarbonyl)piperidin-4-yl] ((1-isopropyl-sulfonyl-2-amino-6-formyl)-benzimidazole)-imine Combine 1-isopropylsulfonyl-2-amino-6-formylbenzimidazole (1.0 g, 3.7 mmol) and 1-(ethoxycarbonyl)-4-aminopiperidine (0.64 g, 3.7 mmol) in dimethylformamide (5 mL) and stir at room temperature over night. Dilute the reaction mixture with ethyl acetate (50 mL) and wash sequentially with water (2×10 mL) and saturated aqueous sodium chloride (2×10 mL). Dry the remaining organic phase over sodium sulfate and concentrate under reduced pressure to provide 1.5 g (95%) of the title compound. MS(ES⁻): m/z=422.2 (M−H)⁻.

The compounds of Preparations 10-41 are prepared essentially as described in Preparation 9. In some examples, addition of one equivalent of triethylamine is needed to get complete conversion to the imine derivative.

| Prep. | Compound | MS(ES⁺): m/z = |
|---|---|---|
| 10 | N-[1-(benzyl)piperidin-4-yl] ((1-isopropylsulfonyl-2-amino-6-formyl)-benzimidazole)-imine | 439.9 (M + H)⁺ |
| 11 | N-[2-(morpholin-4-yl)eth-1-yl] ((1-isopropylsulfonyl-2-amino-6-formyl)-benzimidazole)-imine | 379.9 (M + H)⁺ |
| 12 | N-[3-(morpholin-4-yl)prop-1-yl] ((1-isopropylsulfonyl-2-amino-6-formyl)-benzimidazole)-imine | 393.9 (M + H)⁺ |
| 13 | N-[1,4-dioxaspiro[4.5]dec-8-yl] ((1-isopropylsulfonyl-2-amino-6-formyl)-benzimidazole)imine | 406.9 (M + H)⁺ |
| 14 | N-[4-hydroxycyclohex-1-yl] ((1-isopropylsulfonyl-2-amino-6-formyl)-benzimidazole)-imine | 364.9 (M + H)⁺ |
| 15 | N-[cyclohexyl] ((1-isopropylsulfonyl-2-amino-6-formyl)-benzimidazole)-imine | 348.9 (M + H)⁺ |
| 16 | N-[methyl] ((1-isopropylsulfonyl-2-amino-6-formyl)-benzimidazole)-imine | 280.9 (M + H)⁺ |
| 17 | N-[3-(phenyl)prop-1-yl] (1-isopropylsulfonyl-2-amino-6-formylbenzimidazole)-imine | 384.9 (M + H)⁺ |
| 18 | N-[2-(methoxy)eth-1-yl] ((1-isopropylsulfonyl-2-amino-6-formylbenzimidazole)-imine | 324.9 (M + H)⁺ |
| 19 | N-[2-((tert-butoxycarbonyl)amino)eth-1-yl] ((1-isopropylsulfonyl-2-amino-6-formyl)-benzimidazole)-imine | 409.9 (M + H)⁺ |
| 20 | N-[tetrahydropyran-4-yl] ((1-isopropylsulfonyl-2-amino-6-formyl)-benzimidazole)-imine | 350.9 (M + H)⁺ |
| 21 | N-[4-((tert-butoxycarbonyl)amino)cyclohex-1-yl] ((1-isopropylsulfonyl-2-amino-6-formyl)-benzimidazole)-imine | 463.9 (M + H)⁺ |
| 22 | N-[2-hydroxyeth-1-yl] ((1-isopropylsulfonyl-2-amino-6-formyl)-benzimidazole)-imine | 311.0 (M + H)⁺ |
| 23 | N-[(pyridin-4-yl)methyl] ((1-isopropylsulfonyl-2-amino-6-formyl)-benzimidazole)-imine | 357.9 (M + H)⁺ |
| 24 | N-[2,4-difluorobenzyl] ((1-isopropylsulfonyl-2-amino-6-formyl)-benzimidazole)-imine | 392.9 (M + H)⁺ |
| 25 | N-[4-fluorobenzyl] ((1-isopropylsulfonyl-2-amino-6-formyl)-benzimidazole)-imine | 374.9 (M + H)⁺ |
| 26 | N-[2,2,6,6-tetramethylpiperidin-4-yl] ((1-isopropylsulfonyl-2-amino-6-formyl)-benzimidazole)-imine | 406.0 (M + H)⁺ |
| 27 | N-[(pyridin-3-yl)methyl] ((1-isopropylsulfonyl-2-amino-6-formyl)-benzimidazole)-imine | 357.9 (M + H)⁺ |
| 28 | N-[(pyridin-2-yl)methyl] ((1-isopropylsulfonyl-2-amino-6-formyl)-benzimidazole)-imine | 357.9 (M + H)⁺ |
| 29 | N-[(cyclopropyl)methyl] ((1-isopropylsulfonyl-2-amino-6-formyl)-benzimidazole)-imine | 321.0 (M + H)⁺ |
| 30 | N-[3-fluorobenzyl] ((1-isopropylsulfonyl-2-amino-6-formyl)-benzimidazole-)-imine | 375.0 (M + H)⁺ |

-continued

| Prep. | Compound | MS(ES+): m/z = |
|---|---|---|
| 31 | N-[2-fluorobenzyl] ((1-isopropylsulfonyl-2-amino-6-formyl)-benzimidazole)-imine | 375.0 (M + H)+ |
| 32 | N-[[(R)-phenyl]-2-hydroxyeth-1-yl] ((1-isopropylsulfonyl-2-amino-6-formylbenzimidazole)-imine | 386.9 (M + H)+ |
| 33 | N-[(trans-4-hydroxy)cyclohexyl] ((1-isopropylsulfonyl-2-amino-6-formyl)-benzimidazole)-imine | 365.0 (M + H)+ |
| 34 | N-[(cis-2-hydroxymethyl)cyclohexyl] ((1-isopropylsulfonyl-2-amino-6-formyl)-benzimidazole)-imine | 379.0 (M + H)+ |
| 35 | N-[4-tert-butylcyclohexyl] ((1-isopropylsulfonyl-2-amino-6-formyl)-benzimidazole)-imine | 405.0 (M + H)+ |
| 36 | N-[[(S)-phenyl]-2-hydroxyeth-1-yl]((1-isopropylsulfonyl-2-amino-6-formyl)-benzimidazole)-imine | 387.0 (M + H)+ |
| 37 | N-[(S)-(1-hydroxy-3-cyclohexyl)prop-2-yl] ((1-isopropylsulfonyl-2-amino-6-formyl)-benzimidazole)-imine | 407.1 (M + H)+ |
| 38 | N-[ethyl] ((1-isopropylsulfonyl-2-amino-6-formyl)-benzimidazole)-imine | 295.2 (M + H)+ |
| 39 | N-[cyclopropyl] ((1-(isopropylsulfonyl-2-amino-6-formyl)-benzimidazole)-imine | 307.2 (M + H)+ |
| 40 | N-[cyclopentyl] ((1-(isopropylsulfonyl-2-amino-6-formyl)-benzimidazole)-imine | 335.3 (M + H)+ |
| 41 | N-[tert-butyl] ((1-isopropylsulfonyl-2-amino-6-formyl)-benzimidazole)-imine | 323.3 (M + H)+ |

Preparation 42

N-[methyl] N-[methoxy] 1-(isopropylsulfonyl)-2-aminobenzimidazole-6-carboxamide

A. N-[methyl]-N-methoxyl 3,4-dinitrobenzamide

Cool a mixture of 3,4-dinitrobenzoic acid (195 g, 0.92 moles), 1.3 L of dry dichloromethane, and 2 mL dimethylformamide to −12° C. under a nitrogen atmosphere. Add oxalyl chloride (134 ml, 1.54 moles) dropwise via addition funnel over 35 minutes and stir the reaction mixture at room temperature under a nitrogen atmosphere overnight. Remove excess oxalyl chloride from the reaction mixture by repetitive cycles of concentrating a dichloromethane solution of the reaction mixture under reduced pressure. Cool a mixture of the residue in 1 L dichloromethane to −5° C. under a nitrogen atmosphere and add N,O-dimethylhydroxylamine hydrochloride (98.7 g, 1.01 moles) followed by the careful addition of 209 mL (2.62 moles) of dry pyridine in portions. Stir the mixture at room temperature for 4 hours and then concentrate under reduced pressure. Suspend the residue in 500 mL dichloromethane and concentrate under reduced pressure twice. Suspend the residue in 500 mL dichloromethane and filter. Store the filtrate at −13° C. for 3 days, filter the solid and rinse with cold dichloromethane. Dilute the filtrate with water (40 mL) and stored at −13° C. again to provide a second crop. Dry the combined crops under reduced pressure to provide 182 g (77%) of the desired compound.

B. N-[methyl] N-[methoxyl] 3,4-diaminobenzamide

Add 18.0 g of 10% weight Pd/C catalyst to a solution of N-[methyl] N-[methoxy] 3,4-dinitrobenzamide (182 g, 0.712 moles) in 900 mL tetrahydrofuran and 900 mL ethanol under a nitrogen atmosphere. Hydrogenate at room temperature for 6 hours under 60 p.s.i. Filter the mixture through Celite® and concentrate the filtrate under reduced pressure. Suspend the residue in 500 mL dichloromethane, concentrate under reduced pressure and dry the residue under reduced pressure to provide 135 g (97%) of the desired compound.

C. N-[methyl] N-[methoxy] 3-(isopropylsulfonyl)amino-4-aminobenzamide

Add dry pyridine (234 mL, 2.94 moles) to a cold (0° C.) solution of N-[methyl] N-[methoxy] 3,4-diaminobenzamide (135 g, 0.69 moles) in 1 liter of dry dichloromethane under a nitrogen atomosphere. Add isopropylsulfonyl chloride (85.4 mL, 0.76 moles) at 0° C. over 30 minutes, stir the mixture 0° C. for another 30 minutes, and then at room temperature overnight. Concentrate the reaction mixture under reduced pressure and partition the residue with diethyl ether (1 L) and 5 N hydrochloric acid (1 L). Separate the layers, discard the diethyl ether layer, add ethyl acetate (1.5 L) to the aqueous layer and stir while adding solid sodium carbonate until pH=6.5. Extract the aqueous layer using ethyl acetate, wash the combined organic layers, dry over magnesium sulfate and concentrate under reduced pressure. Subject the residue to silica gel chromatography eluting with a gradient 65:3 ethyl acetate:hexane to 100% ethyl acetate to provide a 40% yield of the desired compound.

D. Imidazole Ring Formation

Add 5 N sodium hydroxide (55 mL) over 1 hour to a suspension of N-[methyl] N-[methoxy] 3-(isopropylsulfonyl)amino-4-aminobenzamide (83 g, 0.28 moles) in 550 mL of isopropyl alcohol and 28 mL of water. Stir the reaction mixture for an additional hour and then cool to 3° C. Add cyanogen bromide (29.0 g, 0.27 moles) in portions and stir at room temperature over night, at reflux for 5 hours, and then at room temperature overnight. Add ethyl acetate (1.5 L), stir vigorously and then filter the resulting suspension. Wash the filtrate with saturated aqueous sodium chloride, dry over magnesium sulfate and then concentrate to about ¼ volume. Filter the suspension and wash the solid with cold ethyl acetate. Concentrate the filtrate under reduced pressure and crystallize the residue from ethyl acetate to provide a second crop. The combined crops provide a 60% yield of the title compound. MS(FD$^+$): m/z=326 (M+H)$^+$

Preparation 43

N-[methyl] N-[methoxy] 2-(tert-butyldimethylsilyl)oxy-2-(4-fluorophenyl)acetamide A. Methyl p-fluoromandelate Add potassium carbonate (12 g, 87 mmol) followed by iodomethane (7.37 mL, 118 mmol) to a 0° C. solution of p-fluoromandelic acid (79 mmol, 13.4 g) in 160 mL dry dimethylformamide under a nitrogen atmosphere. Stir the resulting mixture at 0° C. for 1 hour and at room temperature over night. Pour the reaction mixture over ice, dilute with water and ethyl acetate, and extract the aqueous layer three times with ethyl acetate. Wash the combined organic layers with cold water and saturated aqueous sodium chloride, dry over sodium sulfate and concentrate under reduced pressure to provide 12.7 g (87%) of the desired compound as a light yellow oil.

B. N-[methyl] N-[methoxyl] 2-hydroxy-2-(4-fluorophenyl)acetamide

Cool a mixture of N-methyl-O-methyl hydroxylamine hydrochloride (118 mmol) and toluene (125 mL) to -5° C. Slowly add trimethylaluminum (2 M in heptane, 59.2 mL, 118 mmol) to the mixture over 20 minutes, maintaining the reaction temperature from -1 to 8° C. After about 5 minutes slowly warm the mixture to room temperature and stir for 1.5 hours. Add a solution of methyl p-fluoromandelate (11.1 g, 60 mmol) in 75 mL of toluene over 30 min without external cooling. Cool the reaction to 0° C. and quench with 10% hydrochloric acid. Extract with ethyl acetate (4×250 mL). Wash the combined ethyl acetate layers sequentially with water and saturated aqueous sodium chloride, dry over sodium sulfate and concentrate under reduced pressure to provide 12.1 g (82%) of the desired compound.

C. O-Silylation

Add triethylamine (17.2 mL, 123 mmol) followed by ten-butyldimethylsilyl triflate (20.8 mL, 90 mmol) to a 0° C. solution of N-[methyl] N-[methoxy] 2-hydroxy-2-(4-fluorophenyl)acetamide (12.1 g, 62 mmol) in 180 mL of dichloromethane under a nitrogen atmosphere. Stir the reaction mixture at 0° C. for 1 hour and at room temperature for 4 hours. Add a saturated aqueous solution of ammonium chloride and dilute with diethyl ether. Wash the organic layer sequentially with water and saturated aqueous sodium chloride, dry over sodium sulfate, and concentrate under reduced pressure. Purify the residue by silica gel chromatography, eluting with 9:1 hexane:ethyl acetate to provide the title compound as a yellow oil in 55% yield.

Preparation 44

N-[methyl] N-[methoxy] 2-(tert-butyldimethylsilyl)oxy-2-(4-(trifluoromethyl)phenyl)acetamide Beginning with p-(trifluoromethyl)mandelic acid, prepare the title compound essentially as described in Preparation 43.

Preparation 45

1-isopropylsulfonyl-2-amino-6-(α-((tert-butyldimethylsilyl)oxy)-α-(phenyl)acetyl)-benzimidazole Add isopropylmagnesium chloride (2.0 M in THF, 235 mL, 470 mmol) over 15 minutes to a solution of 1-isopropylsulfonyl-2-amino-6-iodobenzimidazole (42.9 g, 118 mmol) in tetrahydrofuran (850 mL) at -70° C. under a nitrogen atmosphere. Stir for 1 hour at 0° C. and then add a solution of N-[methyl] N-[methoxy] 2-(tert-butyldimethylsilyl)oxy-2-(phenyl)acetamide (90.0 g, 294 mmol) (Tius, et al., *Tetrahedron*, 56, 3339-3351-(2000)) in tetrahydrofuran (150 mL) via cannula. Stir the resulting slurry at 0-5° C. for 1 hour and then at room temperature for 1.5 hours. Cool the mixture to 10° C. and then add saturated aqueous ammonium chloride. Stir the mixture 15 minutes and separate the layers. Extract the aqueous layer with ethyl acetate (400 mL), dry the combined organic layers over sodium sulfate, and concentrate under reduced pressure. Purify the residue by silica gel chromatography, eluting with 1-10% acetonitrile in dichloromethane containing 0.5% triethylamine to provide a 50% yield of the title compound as a white solid. MS(ES$^+$): m/z=488.1 (M+H)$^+$ The compounds of Preparations 46-47 are prepared essentially as described in Preparation 45.

| Prep. | Compound | MS(ES$^+$): m/z = |
|---|---|---|
| 46 | 1-isopropylsulfonyl-2-amino-6-(α-((tert-butyldimethylsilyl)-oxy)-α-((4-fluorophenyl)acetyl))benzimidaole | 506.2 (M + H)$^+$ |
| 47 | 1-isopropylsulfonyl-2-amino-6-(α-((tert-butyldimethylsilyl)-oxy)-α-((4-trifluoromethyl)phenyl)acetyl)benzimidazole | 566.2 (M + H)$^+$ |

Preparation 48

Alternate Synthesis of 1-isopropylsulfonyl-2-amino-6-(α-((tert-butyldimethylsilyl)oxy)-α-(phenyl)acetyl)benzimidazole Add tert-butyllithium (1.5 M solution, 5.8 mL, 8.65 mmol) slowly to a solution of O-(tert-butyldimethyl)silyl benzyl alcohol (1.9 g, 8.54 mmol) in 40 mL of anhydrous tetrahydrofuran at -78° C. under a nitrogen atmosphere. Stir the solution for 3.5 hours, allowing the reaction to warm to -25° C. Cool to -35° C. and add a solution of N-[methyl] N-[methoxy] 1-isopropylsulfonyl-2-aminobenzimidazole-6-carboxamide (0.7 g, 2.13 mmol) in 24 mL of anhydrous tetrahydrofuran. Stir the reaction for 1 hour while slowly warming to 0° C. Add saturated aqueous ammonium chloride and dilute with ethyl acetate. Extract the aqueous layer with ethyl acetate, wash the combined organic layers sequentially with water and saturated aqueous sodium chloride, dry over sodium sulfate and concentrate under reduced pressure. Purify the residue by silica gel chromatography, eluting with 5:1 dichloromethane:acetonitrile to provide 730 mg (70%) of the title compound. MS(ES$^+$): m/z=488.1 (M+H)$^+$

Preparation 49

1-isopropylsulfonyl-2-amino-6-(α-((tert-butyldimethylsilyl)oxy)-α-(3-(trifluoromethyl)phenyl)acetyl)-benzimidazole Beginning with O-(tert-butyldimethyl)silyl-3-(trifluoromethyl)benzyl alcohol, prepare the title compound essentially as described in Preparation 48 (83% yield). MS(ES$^+$): m/z=556.2 (M+H)$^+$

Preparation 50

1-isopropylsulfonyl-2-amino-6-(α-hydroxy)-α-(4-fluorophenyl)acetyl)-benzimidazole Add hydrofluoric acid (48% aq, 14.6 mL) to a suspension of 1-isopropylsulfonyl-2-amino-6-(α-((tert-butyldimethylsilyl)oxy)-α-(4-phenyl)acetyl)-benzimidazole (7.3 g, 14.4 mmol) in acetonitrile (60 mL) at room temperature. The clear solution is stirred for 2.5 hours at room temperature. Collect the resulting white solid by filtration, and wash it with additional acetonitrile (25 mL). Dry the white solid under vacuum to provide 5.49 g (97%) of the title compound. MS(ES$^+$): m/z=392 (M+H)$^+$

Preparation 51

1-isopropylsulfonyl-2-amino-6-(2-(4-fluorophenyl)-ethane-1,2-dione)-benzimidazole Add 1-hydroxy-1,2-benzoiodooxol-3 (1H)-one-1-oxide (IBX) (2.83 g, 10.11 mmol) to a solution of 1-isopropylsulfonyl-2-amino-6-(α-hydroxy)-α-(4-fluorophenyl)acetyl)-benzimidazole (3.16 g, 8.08 mmol) in anhydrous dimethylsulfoxide (25 mL). After 2 hours, add sodium thiosulfate (saturated aqueous solution, 50 mL) and stir at room temperature for 5 minutes. Add water and extract with ethyl acetate. Wash the organic layer with aqueous saturated sodium chloride and dry (MgSO$_4$). After solvent evaporation, purify the crude by column chromatography to provide 2.08 g (74% yield) of the title compound as a pale yellow solid. MS(ES$^+$): m/z=390 (M+H)$^+$

Preparation 52

1-isopropylsulfonyl-2-amino-6-(phenylethynyl)-benzimidazole

Under a nitrogen atmosphere, combine 1-isopropylsulfonyl-2-amino-6-iodo benzimidazole (400 g, 1.095 moles), bis(triphenylphosphine) palladium(II)acetate (32.8 g, 0.044 moles), and CuI (41.7 g, 0.219 moles), followed by DMSO (8.4 L) and triethylamine (317 g, 3.133 moles). Stir the resulting mixture at 20 to 25° C. for 15 minutes, followed by the addition of phenylacetylene (168 g, 1.645 moles) over 30 minutes giving a temperature rise to 34° C. Cool the reaction slowly to 20 to 25° C., and after 15 hours, quench an aliquot of the reaction into water and dilute with CH$_3$CN for HPLC analysis. The HPLC chromatogram (Column:Zorbax SB-C8, 4.6×250 mm, 5 micron UV=218 nm, gradients acetonitrile/buffer) indicates complete consumption of the iodide with the production of two new less polar products (desired product and phenylacetylene dimer). Add water (4 L) to the reaction over 1 hour giving a temperature rise to 40° C., and a dark precipitate (mainly catalyst). Filter the reaction through a thin layer of Celite® (24 cm diameter) with no washing of the catalyst waste cake. Return the filtrate to the reactor and add an additional 4 L of water over 1 hour to give an ending temperature of 45° C., and a yellow slurry. Leave the mixture to cool overnight to 20 to 25° C. with stirring. Collect the solids by vacuum filtration, and wash with water (4 L). Dry the solids at 60° C. under vacuum to constant weight. Yield=319 g (86%) of light yellow granular solid. MS(ES$^+$): m/z=340.2 (M+H)$^+$

Preparation 53

1-cyclopentylsulfonyl-2-amino-6-(phenylethynyl)benzimidazole

Beginning with 1-cyclopentylsulfonyl-2-amino-6-iodo benzimidazole, prepare the title compound essentially as described in Preparation 52 (44% yield). MS (APC$^+$): m/z=366.2 (M+H)$^+$

Preparation 54

1-isopropylsulfonyl-2-amino-6-(2-phenyl-ethane-1,2-dione)-benzimidazole

Combine water (4 L), NaHCO$_3$ (30 g, 0.357 moles), and MgSO$_4$ (145 g, 1.205 moles) at 20 to 25° C., and stir until homogenous (exotherm to 30.5° C.). Add acetone (4 L) to the reaction to give a cloudy mixture, followed by 1-isopropylsulfonyl-2-amino-6-(phenylethynyl)-benzimidazole (200 g, 0.590 moles). Treat the resulting slurry with KMnO$_4$ (360 g, 2.278 moles) to give a gradual exotherm to 40° C. over 1 hour. After an additional 1 hour (35° C.), dilute an aliquot of reaction mixture with CH$_3$CN for HPLC analysis. The HPLC chromatogram indicates complete consumption of the starting material with clean production of a slightly more polar product. Add Na$_2$SO$_3$ (400 g) to the reaction mixture, followed by EtOAc (3 L). Add 20% H$_2$SO$_4$ in water (300 mL) to the reaction mixture over 25 minutes (temperature range 30 to 40° C., large amount of solid MnO$_2$ produced). Allow the phases to separate, and collect an aliquot of the top organic phase for HPLC analysis (HPLC chromatogram indicated clean product). Separate the organic phase and clarify by filtration through Celite®. Back extract the aqueous phase (black and thick) with EtOAc (2 L) and clarify the resulting organic phase by filtration through Celite®. Use EtOAc (1 L) to rinse the Celite®. Combine the organic phases and concentrate (remove 7 L) at 40° C. under vacuum causing two phases to form. Add EtOAc (2 L to the mixture, followed by water (0.5 L) and NaCl (30 g). Separate the layers, and back extract the aqueous phase with EtOAc (0.5 L). Combine the organic phases, dry with MgSO$_4$, and use EtOAc (2 L) to wash the MgSO$_4$. Remove the solvent under vacuum at 40° C. to give 189 g of yellow solids. Dry the solids under vacuum at 60° C. to constant weight to give a final weight of 182 g (83%). Prepare analytically pure final product via recrystallization from EtOAc. MS(ES$^+$): m/z=372.2(M+H)$^+$

Preparation 55

1-cyclopentylsulfonyl-2-amino-6-(2-phenyl-ethane-1,2-dione)-benzimidazole

Beginning with 1-cyclopentylsulfonyl-2-amino-6-(phenylethynyl)-benzimidazole, prepare the title compound essentially as described in the Preparation 54 as a yellow solid 1.29 g (99% yield). MS(APC$^+$): m/z=398.8 (M+H)$^+$

Preparation 56

1-isopropylsulfonyl-2-amino-benzimidazole-6-boronic acid

Charge a 5 L round bottom flask equipped with dry ice/acetone bath, nitrogen atmosphere, mechanical stirrer, thermocouple, and addition funnel with septum with 1-isopropylsulfonyl-2-amino-6-iodo benzimidazole (125 g, 342 mmol) and THF (1.2 L) and cool to −77° C. (results in a slurry). To this slurry add PhLi (1.8 M in c-hexane/ether, 599 mL, 1078 mmol) over 25 minutes keeping the temperature below −67° C. After stirring the resulting green slurry for 20 minutes while cooling to −77° C., add t-BuLi (1.7 M in pentane, 503 mL, 856 mmol) over 25 minutes keeping the temperature of the reaction below −67° C. Stir the mixture at −75° C. for 40 minutes then add triisopropyl borate (276 mL, 1198 mmol) over 15 minutes keeping the temperature below −65° C. Warm the resulting slurry slowly to 0° C. over 2 hours, then add a mixture of concentrated HCl(aq) and water (400 mL) until pH 2 is reached. Stir the mixture for 1 hour then adjust to pH>12 with 5 N NaOH while keeping the temperature <10° C. Add water (1 L), and separate the layers. Wash the aqueous layer with EtOAc (300 mL) then adjust to pH 6 with concentrated HCl(aq). Extract the mixture with EtOAc (2×700 mL), and dry the combined extracts (Na$_2$SO$_4$), filter, and concentrate in vacuo to an orange paste (116 g). Dissolve the paste in warm (~60° C.) 2-propanol (360 mL) then add water (1.4 L). Cool the solution to 0° C. for 3 hours. Collect the resulting solid by filtration, wash with water then air-dry to constant weight to afford the title compound (34.9 g, 36% yield) as light tan crystals. Obtain a second crop from the filtrate (4.95 g, 41% yield overall). MS(ES$^+$): m/z=284 (M+H)$^+$

Preparation 57

2,4-(dibromo)-5-(phenyl)-imidazole

Add to a suspension of 4-phenylimidazole (51.0 g, 354 mol) in AcOH (450 mL) dropwise bromine (39.9 mL, 778 mmol) at room temperature under nitrogen at a rate so as to keep the internal temperature <30° C. using an ice-bath for cooling. Stir the mixture at room temperature for 22 hours (at which time analysis by LC-MS indicates monobromo intermediate is still present). Add additional bromine (12 mL), and stir the reaction for 24 hours then dilute with water (1600 mL). Extract the mixture with ether (800 then 400 mL), and wash the combined organic layers with NaHSO$_3$ (5%, 1000 mL), water (2×1000 mL) then NaHCO3 (500 mL). Dry the organic layer (Na$_2$SO$_4$), filter and partially concentrate in vacuo. Add hexanes (500 mL), and concentrate the mixture again partially in vacuo to ca. 600-700 mL. Collect the solid by filtration and air-dry to afford the title compounds (70.9 g, 66% yield) as a pale yellow powder. MS(ES$^+$): m/z=301 (M+H)$^+$

Preparation 58

1-(trimethylsilylethoxymethyl)-2,5-(dibromo)-4-(phenyl)-imidazole

To a solution of 2,4-(dibromo)-5-(phenyl)-imidazole (73.86 g, 244.6 mmol) in dry THF (800 mL) cooled to 1° C. under nitrogen add portionwise NaH (60% unwashed in mineral oil, 11.25 g, 281 mmol) keeping the reaction temperature <10° C. Cool the mixture to −7° C. then add silylethoxymethyl chloride (SEMCl) (42.0 g, 252 mmol) dropwise (2° C.). Stir the mixture for 2.5 hours (10° C.) then dilute with water (1400 mL) and extract with ether (2×600 mL). Dry the combined organic layers (Na$_2$SO$_4$), filter and concentrate in vacuo. Filter the crude material through a plug of silica gel (700 g) eluted with hexanes (3 L), then 10% (3 L) and 20% (3 L) EtOAc/hexanes to provide material which is recrystallized from hot isopropyl alcohol (500 mL) that is cooled to room temperature over 2 hours then to 5° C. for 30 minutes. Collect the solid by filtration washing with cold isopropyl alcohol then air-dry to afford 54.2 g (51% yield) as white crystals. MS(ES$^+$): m/z=431 (M+H)$^+$

Preparation 59

1-(trimethylsilylethoxymethyl)-2-(formyl)-5-(bromo)-4(phenyl)-imidazole

To a solution of 1-(trimethylsilylethoxy)-2,5-(dibromo)-4(phenyl)-imidazole (60.3 g, 140 mmol) in dry THF (600 mL) cooled to −11° C. under nitrogen add dropwise a solution of isopropylmagnesium chloride (2M THF, 87.2 mL, 174 mmol) causing an exotherm to 1° C. Stir the mixture at this temperature for 30 minutes then add dry DMF (32.4 mL, 419 mmol) (8° C.), and stir for 45 minutes. Add saturated aqueous solution of NH$_4$Cl (500 mL) and water (100 mL), separate the layers, and extract the aqueous layer with ethyl acetate (300 mL). Dry the combined organic layers (Na$_2$SO$_4$), filter and concentrate in vacuo, and purify the residue by chromatography (Biotage 75 long; eluted with 5% EtOAc/hexanes) to provide 33.6 g (63% yield) as a yellow oil. MS(ES$^+$): m/z=323 (M+H)$^+$

Preparation 60

1-isopropylsulfonyl-2-amino-6-(1-(trimethylsilylethoxymethyl)-2-(formyl)-4-(phenyl)-imidazol-5-yl)-benzimidazole To a solution of 1-(trimethylsilylethoxymethyl)-2-(formyl)-5-(bromo)-4-(phenyl)-imidazole (532 mg, 1.39 mmol) in dry toluene (9 mL) previously bubbled with a stream of nitrogen, add PdCl$_2$(PPh$_3$)$_2$ (49 mg, 0.0697 mmol) in one portion. After 5 minutes, add a suspension of 1-isopropylsulfonyl-2-amino-6-boronic acid-benzimidazole (472 mg, 1.67 mmol) in ethanol (6 mL) previously bubbled with a stream of nitrogen, followed by sodium carbonate (2 M in water, 3.4 ml, 6.95 mmol). Stir the mixture for 2.5 hours at 90° C., cool to room temperature and dilute with water (20 mL). Extract the mixture with EtOAc (3×30 mL) and wash the combined organic layers with saturated aqueous sodium chloride (30 mL), dry (MgSO$_4$) and concentrate in vacuo. Purify the residue by flash chromatography (SiO$_2$; eluent: hexane/EtOAc 1:1 to 1:3) to obtain a brown solid, 384 mg, 51% yield. MS(ES$^+$): m/z=540.2 (M+H)$^+$ Preparation 61

1-benzyl-2,4,5-tribromo-imidazole

Combine 2,4,5-tribromoimidazole (15.29 g, 0.050 mol), cesium carbonate (18.0 g, 0.055 mol), benzyl bromide (6.3 mL, 0.053 mol) and dimethylformamide (100 mL) and stir at 20° C. for 18 hours. Filter solids and concentrate under reduced pressure. Suspend in dichloromethane, filter through 2 cm pad silica gel and wash with dichloromethane (1 L). Concentrate filtrates under reduced pressure. Redissolve in dichloromethane (15 mL), add 4 M HCl in dioxane (12.5 mL, 0.050 mol), cool to −20° C. and filter solids. Concentrate filtrate, dissolve in ethyl ether, add 1 M HCl/ether (20 mL) and hexane (40 mL), cool −20° C. and filter. Combine solids and dry under reduced pressure to give 19.6 g (90%, 0.045 mol) of the title compound. MS(ES$^+$): m/z=393.0 (M+H)$^+$ Preparation 62

1-benzyl-4,5-dibromo-2-(2,4-difluoro-phenyl)-imidazole

Reflux a mixture of 1-benzyl-2,4,5-tribromoimidazole (1.043 g, 2.42 mmol), 2,4-difluorophenyl boronic acid (0.682 g, 4.32 mmol), palladium acetate (0.027 g, 0.12 mmol), R(+)-2,2'-bis(di-p-tolyl-phosphino)1,1'-binaphthyl (0.098 g, 0.14 mmol), 2 M sodium carbonate (3.6 mL, 4.83 mmol), methanol (3.6 mL) and toluene (36 mL) for 18 hours. Cool to ambient temperature and dilute with ethyl acetate. Wash with saturated sodium carbonate, saturated sodium chloride, dry with magnesium sulfate and purify the residue on silica gel eluting with hexane/ethyl acetate mixtures to provide 1-benzyl-4,5-dibromo-2-(2,4-difluoro-phenyl)-1H-imidazole (0.39 g). MS(ES$^+$): m/z=461.1 (M+H)$^+$ Preparation 63

1-benzyl-4-bromo-5-(3,5-difluoro-phenyl)-2-(2,4-difluoro-phenyl)-imidazole

Reflux a mixture of 1-benzyl-4,5-dibromo-2-(2,4-difluoro-phenyl)-imidazole (0.386 g, 0.90 mmol), 3,5-difluorophenyl boronic acid (0.15 g, 0.945 mmol), trans-dichlorobis(triphenylphosphine) palladium (II) (0.065 g, 0.09 mmol), 2 M sodium carbonate (0.90 mL), methanol (1.5 mL) and toluene (10 mL) for 18 hours, then cool to ambient temperature. Dilute with ethyl acetate and wash with saturated sodium bicarbonate, saturated sodium chloride, dry with magnesium sulfate, filter and remove solvents under reduced pressure. Purify the residue on silica gel eluting with hexane/ethyl acetate mixtures to provide 1-benzyl-4-bromo-5-(3,5-difluoro-phenyl)-2-(2,4-difluoro-phenyl)-1H-imidazole (0.19 g). MS(ES$^+$): m/z=461.0 (M+H)$^+$ Preparation 64

1-isopropylsulfonyl-2-amino-6-(1-(benzyl)-5-(3,5-difluorophenyl)-2-(2,4-difluorophenyl)-imidazol-4-yl)-benzimidazole Reflux a mixture of 1-benzyl-4-bromo-5-(3,5-difluorophenyl)-2-(2,4-difluoro-phenyl)-imidazole (0.061 g, 0.13 mmol), 1-isopropylsulfonyl-2-amino-benzimidazole-6-boronic acid (0.113 g, 0.40 mmol) (described in preparation 56), trans-dichlorobis(triphenylphosphine) palladium (II) (0.009 g, 0.013 mmol), 2 M sodium carbonate (0.20 mL) and 1,2-dimethoxyethane (5 mL) for 18 hours. Cool to ambient temperature, dilute with ethyl acetate and wash with saturated sodium bicarbonate, saturated sodium chloride, dry with magnesium sulfate, filter and remove solvents under reduced pressure. Purify on silica gel with dichloromethane/methanol mixtures to provide the title compound (0.084 g). MS(ES$^+$): m/z=620.1 (M+H)$^+$ Preparation 65

1-benzyl-4,5-dibromo-2-methyl-imidazole

To a solution of 4,5-dibromo-2-methylimidazole (3.0 g, 12.5 mmol) in 25 mL DMF add sodium carbonate (2.0 g, 18.8 mmol) and benzyl bromide (1.64 mL, 13.8 mmol). Stir the solution at room temperature for 72 hours. Pour the reaction into water and extract with EtOAc. Wash the organic layer with water, saturated aqueous sodium chloride, and dry over sodium sulfate. Filter the mixture and concentrate to 3.8 g crude oil. Purify the oil by radial chromatography eluting with 40% EtOAc in hexanes. Concentrate the appropriate fractions to 3.1 g (75%) of the title compound as a colorless oil. MS(ES$^+$): m/z=331.0 (M+H)$^+$ Preparation 66

1-benzyl-4-bromo-5-(2,4-difluorophenyl)-2-methyl-imidazole

To a solution of 1-(benzyl)-4,5-(dibromo)-2-(methyl)-imidazole (1.71 g, 5.18 mmol) in 8 mL DME, add 2,4-difluorophenyl boronic acid (0.90 g, 5.70 mmol). Add sodium carbonate (1.65 g, 15.5 mmol) dissolved in 1 mL of water and trans-dichlorobis(triphenylphosphine) palladium (II) (1.09 g, 1.55 mmol). Heat the mixture to 100° C. with stirring under nitrogen. After 3 hours the solution is cooled and filtered over a pad of Celite® and sodium sulfate. The crude product is purified by radial chromatography eluting with 35% EtOAc, 1% CH$_2$Cl$_2$ in hexanes to yield 1.12 g (60%) of the title compound as a yellow oil. This compound is used directly without further purification. MS(ES$^+$): m/z=364.0 (M+H)$^+$

Preparation 67

1-isopropylsulfonyl-2-amino-6-(1-(benzyl)-5-(2,4-difluorophenyl)-2-(methyl)-imidazol-4-yl)-benzimidazole To a solution of 1-(benzyl)-4-(bromo)-5-(2,4-difluorophenyl)-2-(methyl)-imidazole (1.12 g, 3.08 mmol) in 8 mL DME add 1-isopropylsulfonyl-2-amino-benzimidazole-6-boronic acid (2.62 g, 9.25 mmol) (described in preparation 58). Add sodium carbonate (0.98 g, 9.25 mmol) dissolved in water (1 mL) and trans-dichlorobis(triphenylphosphine) palladium (II) (0.65 g, 0.93 mmol). Heat the mixture to 100° C. with stirring under nitrogen. After 3 hours cool the solution and filter over a pad of Celite and sodium sulfate. Purify the residue by radial chromatography eluting with 3% methanol in $CH_2Cl_2$ with a gradient to 10% methanol. Perform a second purification by radial chromatography eluting with 4% methanol in $CH_2Cl_2$ with a gradient to 6% methanol to yield 390 mg (24%) of the title compound as a yellow solid. MS(ES$^+$): m/z=522.0 (M+H)$^+$

Preparation 68

5-bromo-3-methyl-1-phenyl-pyrazole

To a solution of 3-methyl-1-phenyl-2-pyrazol-5-one (2.0 g, 11.5 mmol) in 5 mL anhydrous acetonitrile add phosphorus oxybromide (9.9 g, 34.5 mmol). Heat the mixture to reflux for 3 hours under nitrogen. Cool the reaction to 0° C. and dilute with ethyl acetate and water. Dry the organic layer over magnesium sulfate, filter, and concentrate to a crude yellow oil which contains a 1:1 mixture of mono to dibrominated products. Purify the residue by radial chromatography eluting with methylene chloride to yield 677 mg (25%) as a colorless oil. 925 mg of the less polar dibrominated product is isolated as a white solid. MS(ES$^+$): nz/z=238.0 (M+H)$^+$

Preparation 69

5-bromo-3-tert-butyl-1-phenyl-pyrazole

To a solution of 3-tert-butyl-1-phenyl-2-pyrazol-5-one (1.0 g, 4.6 mmol) in 6 mL anhydrous acetonitrile add phosphorus oxybromide (2.0 g, 6.9 mmol). Heat the mixture to reflux for 3 hours under nitrogen. Cool the reaction to 0° C. and dilute with ethyl acetate and water. Dry the organic layer over magnesium sulfate, filter, and concentrate to a crude colorless oil. Purify the title compound by radial chromatography eluting with 70:30 methylene chloride:hexanes to yield 1.1 g (86%) as a colorless oil. MS(ES$^+$): m/z=280.0 (+H)$^+$

Preparation 70

2-phenylimidazo[1,2-a]pyridine

Stir a solution of 2-bromoacetophenone (1 g, 5.024 mmol) and 2-aminopyridine (591 mg, 6.280 mmol) in ethanol (4 mL) containing $NaHCO_3$ (658 mg, 7.837 mmol) at room temperature for 6 hours. Dilute the mixture with water (15 mL) and extract with ether (3×20 mL). Wash the combined organic layers with saturated aqueous sodium chloride (25 mL), dry (MgSO$_4$) and concentrate in vacuo. Purify the residue by flash chromatography (SiO$_2$; eluent:hexane/EtOAc 4:1) to give a white solid, 79% yield. MS(ES$^+$): m/z=195.1 (M+H)$^+$

Preparation 71

8-methyl-2-phenylimidazo[1,2-a]pyridine

Beginning with 2-amino-3-methylpyridine, prepare the title compound essentially as described in Preparation 70, 73% yield. MS(ES$^+$): m/z=195.1 (M+H)$^+$

Preparation 72

3-iodo-2-phenylimidazo[1,2-a]pyridine

Treat a solution of 2-phenylimidazo[1,2-a]pyridine (50 mg, 0.257 mmol) in acetonitrile (1.25 mL) with N-iodosuccinimide (NIS) (69 mg, 0.309 mmol) at room temperature for 5 hours. Dilute the mixture with ether (10 mL), wash with a saturated aqueous solution of NaHCO$_3$ (15 mL) and NaHSO$_3$ (40%, 15 mL), dry (Na$_2$SO$_4$) and concentrate in vacuo. A yellow solid is obtained, 80 mg, 97% yield. MS(ES$^+$): m/z=321.0 (M+H)$^+$

Preparation 73

3-iodo-8-methyl-2-phenylimidazo[1,2-a]pyridine

Beginning with 8-methyl-2-phenylimidazo[1,2-a]pyridine, prepare the title compound essentially as described in Preparation 72, 65% yield. MS(ES$^+$): m/z=335.0 (M+H)$^+$

Preparation 74

2-phenyl-6,7-dihydro-5H-pyrrolo[1,2-a]imidazole

Prepare 2-iminopyrrolidine hydrochloride (6.98 g, 57.8 mmol) according to Callahan, et al., J. Med. Chem. 2002, 45, 999-1001) and combine 2-bromoacetophenone (3.8 g, 19.3 mmol) with Na$_2$CO$_3$ (8.2 g, 77.2 mmol) in dry DMF (25 mL) and heat at 80° C. for 18 hours. Then, cool the mixture to room temperature, add water (60 mL), and extract with EtOAc (3×100 mL). Concentrate the combined organic layers in vacuo, dilute the residue with ether (100 mL), and wash with cooled water (3×80 mL). Concentrate the organic layer in vacuo to give a white solid, 3.2 g, 89% yield. MS(ES$^+$): m/z=185.1 (M+H)$^+$

Preparation 75

2-(4-fluorophenyl)-6,7-dihydro-5H-pyrrolo[1,2-a]imidazole

Beginning with 2-iminopyrrolidine hydrochloride and 2-fluoroacetophenone, prepare the title compound essentially as described in Preparation 74, 99% yield.

Preparation 76

3-bromo-2-phenyl-6,7-dihydro-5H-pyrrolo[1,2-a]imidazole

To a solution of 2-phenyl-6,7-dihydro-5H-pyrrolo[1,2-a]imidazole (3.38 g, 18.3 mmol) in dry $CH_2Cl_2$ (113 mL) slowly add bromine (1.0 mL, 20.2 mmol) and stir the mixture at room temperature for 1.5 hours. Add a saturated aqueous solution of $NaHCO_3$ (100 mL) and extract with $CH_2Cl_2$ (3×100 mL). Wash the combined organic layers with $NaHSO_3$ (40%, 30 mL), dry ($MgSO_4$) and concentrate in vacuo. Purify the residue by flash chromatography ($SiO_2$, eluent: $CH_2Cl_2$ to $CH_2Cl_2$/MeOH 20:1) to yield a red solid, 3.54 g, 73% yield. $MS(ES^+)$: m/z=263.0 $(M+H)^+$

Preparation 77

3-bromo-2-(4-fluorophenyl)-6,7-dihydro-5H-pyrrolo[1,2-a]imidazole

Beginning with 2-(4-fluorophenyl)-6,7-dihydro-5H-pyrrolo[1,2-a]imidazole, prepare the title compound essentially as described in Preparation 76, 95% yield.

Preparation 78

2-phenyl-5,6,7,8-tetrahydro-imidazo[1,2-a]pyridine

Combine 2-iminopiperidine hydrochloride (4.9 g, 36.4 mmol, 3 equiv) and 2-bromoacetophenone (2.4 g, 12.1 mmol) with $Na_2CO_3$ (5.1 g, 48.4 mmol) in dry DMF (15 mL) and heat the mixture at 80° C. for 16 hours. Then, cool the mixture to room temperature, add water (200 mL), and extract with ether (3×100 mL). Wash the combined organic layers with water (2×50 mL), and re-extract the aqueous layer with ether (2×50 mL). Wash the combined organic layers with saturated aqueous sodium chloride (100 mL), dry ($MgSO_4$), and concentrate in vacuo. Purify the residue by flash chromatography ($SiO_2$; eluent: $CH_2Cl_2$ to $CH_2Cl_2$:MeOH 50:1) to obtain a brown solid, 1.7 g, 71% yield. $MS(ES^+)$: m/z=199.1 $(M+H)^+$

Preparation 79

3-bromo-2-phenyl-5,6,7,8-tetrahydro-imidazo[1,2-a]pyridine

To a solution of 2-phenyl-5,6,7,8-tetrahydro-imidazo[1,2-a]pyridine (1.7 g, 8.9 mmol) in dry $CH_2Cl_2$ (55 mL) slowly add bromine (0.5 mL, 9.8 mmol) and stir at room temperature for 3 hours. Then, add a saturated aqueous solution of $NaHCO_3$ (100 mL) and extract with $CH_2Cl_2$ (3×100 mL). Wash the combined organic layers with $NaHSO_3$ (40%, 30 mL) followed by saturated aqueous sodium chloride (50 mL), dry ($MgSO_4$), and concentrate in vacuo. Purify the residue by flash chromatography ($SiO_2$, eluent:$CH_2Cl_2$ to $CH_2Cl_2$/MeOH 20:1) to obtain a brown solid, 2.0 g, 82% yield. $MS((ES^+)$: m/z=277.0, $(M+H)^+$

Preparation 80

3-ethoxycarbonyl-2-phenyl-5,6-dihydro-4H-pyrrolo[1,2-b]pyrazole

To a solution of 1-amino-pyrrolidine-2-one hydrochloride (3.8 g, 27.8 mmol) (WO 02/094833) add ethylbenzoylacetate (4.3 mL, 25 mmol) followed by pyridine (10 mL) at room temperature under nitrogen. Stir the mixture at room temperature for 20 hours and then, dilute with water (50 mL) and extract with toluene (2×50 mL). Dry the combined organic layers ($MgSO_4$) and concentrate in vacuo to give a brown oil, 6.23 g, 82% yield, and treat with NaOEt (freshly prepared, 3.1 g, 45.4 mmol, 2 equiv) in toluene at 120° C. for 8 hours. Cool the mixture to room temperature and add water (100 mL) and concentrated HCl until a pH of 4 is reached. Extract the mixture with EtOAc (3×200 mL) and dry ($MgSO_4$) the combined organic layers and concentrate in vacuo. Purify the residue in a biotage system (eluent: $CH_2Cl_2$/MeOH 40:1) to obtain a yellow solid, 1.8 g, 36% yield. $MS(ES^+)$: m/z=257.1 $(M+H)^+$

Preparation 81

3-bromo-2-phenyl-5,6-dihydro-4H-pyrrolo[1,2-b]pyrazole

A. 3-carboxy-2-phenyl-5,6-dihydro-4H-pyrrolo[1,2-b]pyrazole

To a solution of 3-ethoxycarbonyl-2-phenyl-5,6-dihydro-4H-pyrrolo[1,2-b]pyrazole (2.1 g, 8.2 mmol) in MeOH (20 mL) add a solution of NaOH (15%, 40 mL) followed by acetonitrile (5 mL) and stirr at 50° C. for 3 hours. Cool the mixture to room temperature and add HCl (10%) until a pH of 3 is reached. Extract the mixture with EtOAc (3×100 mL) and wash with saturated aqueous sodium chloride (100 mL), dry ($MgSO_4$), and concentrate in vacuo to give a yellow solid, 1.82 g, 97% yield, $MS(ES^+)$: m/z=229.1 $(M+H)^+$ B. 3-bromo-2-phenyl-5,6-dihydro-4H-pyrrolo[1,2-b]pyrazole To a solution of 3-carboxy-2-phenyl-5,6-dihydro-4H-pyrrolo[1,2-b]pyrazole (820 mg, 3.59 mmol) in dry DMA (15 mL) previously degassed add N-bromosuccinimide (NBS) (702.8 mg, 3.95 mmol) and stir at room temperature for 18 hours. Then, dilute with EtOAc (80 mL) and wash with cooled water (5×10 mL). Dry the organic phase ($MgSO_4$), and concentrate in vacuo to obtain a yellow solid, 1.0 g. $MS(ES^+)$: m/z=263.0 $(M+H)^+$

Preparation 82

1-(4-methoxybenzyl)-4-phenylimidazole

To a solution of 4-phenylimidazole (7.49 g, 51.9 mmol) in DMF (30 mL) cooled to 0° C. under nitrogen add portionwise NaH (95%, 2.56 g, 101 mmol). After 10 minutes, add p-methoxybenzyl chloride (PMBCl) (7.50 mL, 55.3 mmol) dropwise. Stir for 5 hours, quench with MeOH (5 mL), dilute with water (100 mL), and extract with $CH_2Cl_2$ (2×100 mL). Dry the combined organic layers ($Na_2SO_4$) and concentrate in vacuo to a volume of 80 mL, affording 12.2 g (89% yield) after crystallization. $MS(ES^+)$: m/z=265 $(M+H)^+$

Preparation 83

1-(4-methoxybenzyl)-2-formyl-4-phenylimidazole

To a solution of 1-(4-methoxybenzyl)-4-phenylimidazole (2.00 g, 7.56 mmol) in THF (20 mL) cooled to −78° C. under nitrogen add dropwise a solution of n-butyl lithium (1.6 M hexane, 5.60 mL, 8.96 mmol). Stir the mixture at this temperature for 10 minutes then add DMF (1.43 mL, 18.5 mmol) dropwise, and continue stirring for 30 minutes. Add a saturated aqueous solution of NH$_4$Cl (50 mL), raise the temperature to room temperature, and extract the aqueous layer with CH$_2$Cl$_2$ (150 mL), dry (Na$_2$SO$_4$), and concentrate in vacuo. Purify the residue by flash chromatography (SiO$_2$, hexane/EtOAc 9:1) to provide 1.75 g (79% yield). MS(ES$^+$): m/z=293 (M+H)$^+$

Preparation 84

1-(4-methoxybenzyl)-2-hydroxymethyl-4-phenylimidazole

Treat a solution of 1-(4-methoxybenzyl)-2-formyl-4-phenylimidazole (1.75 g, 5.99 mmol) in CH$_2$Cl$_2$/MeOH (1:1, 60 mL) with NaBH$_4$ (480 mg, 12.7 mmol) at room temperature for 15 minutes. Quench with H$_2$O (50 mL), extract with CH$_2$Cl$_2$ (2×100 mL), dry (Na$_2$SO$_4$), and concentrate in vacuo. Purify the residue by flash chromatography (SiO$_2$, CH$_2$Cl$_2$/MeOH 20:1→7:1) to provide 1.69 g (96% yield). MS(ES$^+$): m/z=295 (M+H)$^+$

Preparation 85

1-(4-methoxybenzyl)-2-tert-butyldimethylsilyloxymethyl-4-phenylimidazole

Treat a solution of 1-(4-methoxybenzyl)-2-hydroxymethyl-4-phenylimidazole (1.68 g, 5.71 mmol) in CH$_2$Cl$_2$ (35 mL) with N,N-diisopropylethylamine (3.2 mL, 18.4 mmol) and tert-butyldimethylsilyl chloride (TBSCl) (1.46 g, 9.69 mmol) at room temperature for 60 hours. Quench with H$_2$O (40 mL), extract with CH$_2$Cl$_2$ (100 mL), dry (Na$_2$SO$_4$), and concentrate in vacuo. Purify the residue by flash chromatography (SiO$_2$, hexane/EtOAc 20:1→9:1) to provide 2.09 g (90% yield). MS (ES$^+$): m/z=409 (M+H)$^+$

Preparation 86

1-(4-methoxybenzyl)-2-tert-butyldimethylsilyloxymethyl-4-phenyl-5-iodoimidazole Treat a solution of 1-(4-methoxybenzyl)-2-tert-butyldimethylsilyloxymethyl-4-phenylimidazole (2.08 g, 5.09 mmol) in MeCN (25 mL) with N-iodosuccinimide (NIS) (1.35 g, 6.00 mmol) at room temperature for 24 hours. Dilute the mixture with Et$_2$O (100 mL), wash with saturated NaHCO$_3$ (25 mL), dry (Na$_2$SO$_4$), and concentrate in vacuo. Purify the residue by flash chromatography (SiO$_2$, hexane/EtOAc 20:1→9:1) to provide 2.30 g (85% yield). MS (ES$^+$): m/z 535 (M+H)$^+$

Preparation 87

1-(benzyloxycarbonyl)-4-formylpiperidine

Add diisobutyl aluminum hydride (1 M in toluene, 30 mL, 30 mmol) over 5 minutes to a solution of 1-(benzyloxycarbonyl)-4-(ethoxycarbonyl)piperidine (7 g, 24 mmol) in anhydrous dichloromethane (150 mL) at −78° C. under a nitrogen atmosphere. Stir the reaction mixture at this temperature for 30 minutes and then add 10% aqueous sodium tartarate (100 mL) followed by dichloromethane. Stir the reaction mixture at room temperature overnight. Separate the phases and extract the aqueous phase with dichloromethane. Wash the combined organic phases sequentially with 10% aqueous sodium tartarate, water, and saturated aqueous sodium chloride. Dry over sodium sulfate and concentrate under reduced pressure. Subject the residue to silica gel chromatography, eluting with 3:1 hexanes:ethyl acetate to provide 3.15 g (53%) of the title compound.

Preparation 88

1-(tert-butoxycarbonyl)-4-formylpiperidine

Beginning with 1-(tert-butoxycarbonyl)-4-(ethoxycarbonyl)piperidine, prepare the title compound essentially as described in Preparation 51.

Preparation 89

4-formyl tetrahydropyran

Beginning with 4-(methoxycarbonyl)tetrahydropyran, prepare the title compound essentially as described in Preparation 87.

Preparation 90

4-(N-tert-butoxycarbonyl-N-ethyl-amino)-benzaldehyde

A. N-BOC Protection

To a solution of 4-amino-benzoic acid methyl ester (4 g, 26.4 mmol), (Boc)$_2$O (8.67 g, 39.6 mmol), and DMAP (0.322 mg, 2.64 mmol) in 50 mL of acetonitrile add triethylamine (7.345 mL, 52.8 mL) dropwise and stir overnight at room temperature. Dissolve the precipitate in ethyl acetate and treat with 3% HCl, extract with ethyl acetate and wash the organic layers with saturated solution of sodium bicarbonate and saturated aqueous sodium chloride, dry over sodium sulphate, and concentrate to obtain 5.3 g of product. Yield 80%.

$^1$H-NMR (CDCl$_3$, 300 MHz): 8.07 (d, 2H, J=8.8), 7.53 (d, 2H, J=8.8), 6.78 (s, 1H) 4.00 (s, 3H), 1.64 (s, 9H)

B. N-alkylation.

To a suspension of sodium hydride 60% (595 mg, 1.1 eq) in dry DMF and under argon atmosphere, slowly add 4-tert-butoxycarbonylamino-benzoic acid methyl ester (3.24 g, 12.9 mmol) and ethyl iodide (1.206 mL, 1.1 mmol) via syringe and stir overnight. Add ethyl acetate, and wash the resulting solution with saturated ammonium chloride and saturated aqueous sodium chloride, dry over sodium sulphate and concentrate. Purify the residue by chromatography eluting with hexane/16% ethyl acetate to obtain 2.85 g of pure product. Yield 79%

$^1$H-NMR (CDCl$_3$, 300 MHz): 8.11 (dd, J=8.5, 2.0 Hz, 2H); 7.40 (dd, J=8.5, 2.0 Hz, 2H); 4.02 (s, 3H); 3.84 (q, J=6.9 Hz, 2H); 1.56 (s, 9H); 1.28 (t, J=6.9 Hz, 3H).

C. Ester Reduction

To a solution of 4-(N-tert-butoxycarbonyl-N-ethyl-amino)-benzoic acid methyl ester (2.85 g, 10.2 mmol) in 65 mL of dry toluene, under argon atmosphere and at −78° C., add dropwise disiobutyl aluminum hydride (DIBAL-H) 1 M in toluene (12.77 mL, 12.77 mmol). Stir the mixture for 1 hour. Add sodium tartrate, remove the bath and stir the mixture overnight. Extract the organic layer with ethyl acetate and wash the organic layers with saturated aqueous sodium chloride, dry over sodium sulphate and concentrate. Purify the residue by chromatography eluting with hexane/acetate(16%) to obtain 1.24 g of pure alcohol. Yield 54%.
$^1$H-NMR (CDCl$_3$, 300 MHz): 7.45 (d, J=8.5 Hz, 2H); 7.30 (d, J=8.5 Hz, 2H); 4.80 (d, J=6.1 Hz, 2H); 3.78 (q, J=7.3 Hz, 2H); 1.78 (t, J=6.1 Hz, 1H); 1.55 (s, 9H); 1.25 (t, J=7.3 Hz, 3H).

D. Alcohol Oxidation

Dissolve 4-(N-tert-butoxycarbonyl-N-ethyl-amino)-benzyl alcohol (1.24 g, 5.52 mmol) in 50 mL acetonitrile. Add to this solution manganese dioxide and stir the mixture for two days at room temperature. Filter the residue through Celite® and concentrate the solvent to give 632 mg of 4-(N-tert-butoxycarbonyl-N-ethyl-amino) benzaldehyde. Yield 52%. $^1$H-NMR (CDCl$_3$, 300 MHz): 9.95 (s, 1H); 7.83 (d, J=8.7 Hz, 2H); 7.39 (d, J=8.7 Hz, 2H); 3.74 (q, J=7.0 Hz, 2H); 1.45 (s, 9H); 1.18 (t, J=7.0 Hz, 3H).

Preparation 91

2,6-difluoro-4-(pyrrolidin-1-yl-ethoxy)-benzaldehyde

A. 1-(3,5 difluoro-phenoxymethyl)-pyrrolidine

Add pyrrolidin-1-yl-ethanol hydrochloride (1.5 g) to a mixture of 3,5-difluorophenol (1.0 g), cesium carbonate (8.78 g), sodium iodide (1.15 g) in dry dimethylformamide (20 mL). Stir at room temperature overnight. Concentrate under reduced pressure and the residue is purified by chromatography eluting with ethyl acetate:hexane (1:1) to provide (0.8 g, 50%) of an oil.

B. 2,6-difluoro-4-(pyrrolidin-1-yl ethoxy)-benzaldehyde

Cool a mixture of 1-(3,5-difluoro-phenoxymethyl)-pyrrolidine (0.1 g) and dry tetrahydrofuran (5 mL) to −78° C. under a nitrogen atmosphere. Add butyllithium (0.29 mL, 1.6 M in tetrahydrofuran) and N,N,N',N'-tetramethylethylenediamine (0.5 mL) and stir for 30 minutes. Then, add dimethylformamide (0.07 mL) and stir at room temperature for 60 minutes. Quench by pouring the reaction mixture into a mixture of cold saturated aqueous ammonium chloride and ethyl acetate. Separate the layers, wash the organic phase with water and then concentrate under reduced pressure to provide (0.10 g, 94%) of the title compound as an oil.

Preparation 92

2-fluoro-4-nitro-benzaldehyde

Add borane-tetrahydrofuran complex (16.21 mL, 1 M) to a mixture of 2-fluoro-4-nitro-benzoic acid (1.2 g) and tetrahydrofuran (10 mL) at 0° C. Heat at 80° C. for 3 hours. Cool at room temperature and add 1 N aqueous hydrochloric acid (20 mL) and extract with ethyl acetate. Wash with saturated aqueous sodium bicarbonate and dry the remaining organic phase over sodium sulfate and concentrate under reduced pressure to provide (0.91 g, 83%) of an oil. Add (2-fluoro-4-nitro-phenyl)-methanol (0.91 g) to a mixture of dioxide manganese (1.1 g) in 20 ml of dichloromethane. Stir at room temperature overnight and filter over Celite®. Concentrate under reduced pressure to provide (0.27 g, 30%) of the title compound as an oil.

Preparation 93

4-formyl-N-methyl-benzenesulfonamide

A. 4-hydroxymethyl-N-methyl-benzenesulfonamide

Add methyl amine (4.5 mL, 2 M in dichloromethane) to a mixture of 4-chlorosulfonyl benzoic acid (0.5 g) and dichloromethane (20 mL). Stir at room temperature overnight. Quench by pouring the reaction mixture into a mixture of saturated aqueous ammonium chloride and ethyl acetate. Separate the layers, wash the organic phase with water, dry the remaining organic phase over sodium sulfate and then concentrate under reduced pressure to provide (0.40 g, 82%) of an oil. Add borane-tetrahydrofuran complex (7.44 mL, 1 M) to a mixture of 4-methylsulfamoyl-benzoic acid (0.4 g) and tetrahydrofuran (10 mL) at 0° C. Heat at 80° C. for 3 hours. Cool at room temperature and add 1 N aqueous hydrochloric acid (20 mL) and extract with ethyl acetate. Wash with saturated aqueous sodium bicarbonate and dry the remaining organic phase over sodium sulfate and concentrate under reduced pressure to provide (0.28 g, 75%) of an oil.

B. 4-formyl-N-methyl-benzenesulfonamide

Add 4-hydroxymethyl-N-methyl-benzenesulfonamide (0.28 g) to a mixture of manganese dioxide (2.8 g) in 20 mL of dichloromethane. Stir at room temperature overnight and filter over Celite®. Concentrate under reduced pressure to provide (0.11 g, 40%) of the title compound as oil.

Preparation 94

2-fluoro-4-methylamino-benzaldehyde

Add diazomethane (22.3 mL, 2 M in ether) to a mixture of 2-fluoro-4-nitro benzoic acid (4.14 g) and ether (50 mL). Stir at room temperature overnight. Concentrate under reduced pressure to provide (4.08 g, 92%) of an oil.

Reflux the mixture of 2-fluoro-4-nitro-benzoic acid methyl ester (0.85 g), ammonium formate (1.1 g) and Pd/C (10%, 0.32 g) in ethanol (20 mL) at 95° C. for 6 hours. Filter over Celite® and concentrate under reduced pressure to provide (0.64 g, 89%) a gray solid.

Add formaldehyde (0.15 g) to a mixture of 2-fluoro-4-amino benzoic acid methyl ester (0.62 g), acetic acid (2.1 mL) and 1,2 dichloroethane (20 mL). Stir at room temperature overnight. Add sodium triacetoxyborohydride (1.15 g) and stir at room temperature for 2 hours. Quench by pouring the reaction mixture into a mixture of saturated aqueous sodium bicarbonate and ethyl acetate. Separate the layers, wash the organic phase with water, dry the remaining organic phase over sodium sulfate and then concentrate under reduced pressure. The residue is purified by chromatography eluting with ethyl acetate:hexane (1:4) to provide 2-fluoro-4-methylamino benzoic acid methyl ester (0.10 g, 15%) as an oil.

Add diisobutyl aluminium hydride (1.0 mL, 1 M in toluene) dropwise to a mixture of 2-fluoromethylamino benzoic acid methyl ester (0.09 g) and dry toluene (7 mL) to −78° C. under a nitrogen atmosphere. Stir the mixture for 2 hours at room temperature. Quench by pouring the reaction mixture into a mixture of saturated aqueous sodium tartrate (20 mL) and ethyl acetate (20 mL). Separate the layers, wash the organic phase with water, dry the remaining organic phase over sodium sulfate and then concentrate under reduced pressure to provide (0.07 g, 88%) of an oil.

Add tetrapropylammonium perruthenate (0.35 g) to a mixture of (2-fluoro-4-methylamino-phenyl)-methanol (0.18 g), 4-methylmorpholine N-oxide (0.38 g) and freshly activated powdered molecular sieves (0.30 g) in dry dichloromethane (10 mL) at room temperature under a nitrogen atmosphere. Stir for 30 minutes and add more dichloromethane and filter through a florisil-Celite® pad. Concentrate under reduced pressure to provide (0.25 g, 76%) of the title compound as an oil.

Preparation 95

1-isopropylsulfonyl-2-chloro-6-iodobenzimidazole

Add 1-isopropylsulfonyl-2-amino-6-iodobenzimidazole (0.20 g, 0.55 mmol) in three portions over 5 minutes to a suspension of copper(II) chloride (0.089 mg, 0.66 mmol) and tert-butylnitrite (0.085 g, 0.1 mL, 0.82 mmol) in 2 mL acetonitrile at 65° C. After 30 minutes pour the resulting green solution into water and extract the aqueous layer with ethyl acetate (3×25 mL). Wash the combined organic phases sequentially with water (2×15 mL) and saturated aqueous sodium chloride (15 mL), dry over sodium sulfate, filter and concentrate under reduced pressure to provide the title compound (0.18 g, 85%).

Preparation 96

2-(tert-butyl-dimethyl-silyloxy)-1-[2-chloro-3-(isopropylsulfonyl)-3H-benzimidazol-5-yl]-2-phenyl-ethanone Under a nitrogen atmosphere, add tert-butyl nitrite (2.44 mL, 18.45 mmol, 1.5 equiv) dropwise to a stirred suspension of $CuCl_2$ (2.20 g, 14.76 mmol) in 43 mL of $CH_3CN$. Heat the resulting mixture at 65° C. and slowly add 1-[2-amino-3-(propane-2-sulfonyl)-3H-benzoimidazol-5-yl]-2-(tert-butyl-dimethyl-silyloxy)-2-phenyl-ethanone (6 g, 12.3 mmol, 1 equiv) in portions over a total period of 10 minutes. Stir the mixture for 30 minutes, cool down to room temperature, pour over 200 mL of water, and dilute with 200 mL of EtOAc. Separate the phases and back extract the organic one with more EtOAc (three times). Dry the combined organic phases over $MgSO_4$, filter, and concentrate in vacuo to afford crude product which is purified by chromatography using $CH_2Cl_2$ as eluent. 42% yield. MS(ES+): m/z=507.1 (M+H)+

Preparation 97

1-[2-benzylamino-3-(propane-2-sulfonyl)-3H-benzimidazol-5-yl]-2-(tert-butyl-dimethyl-silyloxy)-2-phenyl-ethanone To a stirred solution of starting 2-(tert-butyl-dimethyl-silyloxy)-1-[2-chloro-3-(propane-2-sulfonyl)-3H-benzimidazol-5-yl]-2-phenyl-ethanone (588 mg, 1.16 mmol, 1 equiv) in 2 mL of dry THF, add benzyl amine (0.4 mL, 3.48 mmol, 3 equiv) dropwise. Heat the resulting yellow solution at 40° C. for 30 minutes, cool down to room temperature, and add water and $CH_2Cl_2$. Separate the phases and back extract the organic one with more $CH_2Cl_2$ (three times). Dry the combined organic phases over $MgSO_4$, filter, and concentrate in vacuo to afford crude product. Purify by chromatography using $CH_2Cl_2$:hexanes (3:1) to provide the title compound (80% yield). MS(ES+): m/z=578.2 (M+H)+

Preparation 98

2-(tert-butyl-dimethyl-silyloxy)-1-[2-ethylamino-3-(propane-2-sulfonyl)-3H-benzoimidazol-5-yl]-2-phenyl-ethanone Prepare essentially as described in the previous preparation (Preparation 97) starting from 2-(tert-butyldimethyl-silyloxy)-1-[2-chloro-3-(propane-2-sulfonyl)-3H-benzimidazol-5-yl]-2-phenyl-ethanone (760 mg, 1.50 mmol), ethyl amine (0.25 mL, 4.50 mmol, 3 equiv) in 2 mL of THF. Yield: 84%. MS(ES+): m(z=516.3 (M+H)+

Preparation 99

1-isopropylsulfonyl-2-amino-6-(2-ethoxycarbonyl)-1-hydroxy-2-phenylethyl)-benzimidazole To a stirred solution of ethyl phenylacetate (18.5 mmol, 5 equiv.) in dry THF (20 mL) add lithium hexamethyldisilazane (LHMDS) (0.5 M in THF, 22.2 mmol, 6 equiv) at −78° C. Stir the mixture under nitrogen for 30 minutes and then add to a solution of 1-isopropylsulfonyl-2-amino-6-formyl-benzimidazole (Preparation 1, 1 g, 3.7 mmol) in THF (60 mL). Stir the reaction at −78° C. and follow by TLC. Then, add saturated $NH_4Cl$ (20 mL) and ethyl acetate (100 mL). Separate the phases and extract the aqueous layer with ethyl acetate (3×50 mL). Dry the combined organic phases ($Na_2SO_4$) and concentrate in vacuo. Wash the crude product with hexane and wash the remaining solid by dichloromethane to afford the corresponding compound (0.75 g, 62% yield).

Preparation 100

1-isopropylsulfonyl-2-amino-6-(α-((1-hydroxy)-α-(phenyl)acetyl)-benzimidazole To a stirred solution of IBX (3.48 mmol) in DMSO (5 mL) add 1-isopropylsulfonyl-2-amino-6-(2-ethoxycarbonyl)-1-hydroxy-2-phenylethyl)-benzimidazole (2.32 mmol, 1.5 equiv.) at room temperature and stir the mixture overnight (16 hours). Then, add a saturated solution of NaCl (50 mL followed by ethyl acetate (100 mL). Separate the phases and the extract the aqueous layer with ethyl acetate (3×50 mL). Wash the organic phase with $Na_2S_2O_3$ (25 mL) and dry the combined organic phases ($Na_2SO_4$). Chromatograph using hexane:ethyl acetate 1:4 to afford the corresponding compound (90% yield).

Preparation 101

N-[isopropylsulfonyl]-4-methoxy-benzylamine

Add 4-methoxy-benzylamine (11.7 m, 89.5 mmol) to a solution of isopropyl sulfonyl chloride (5.0 mL, 44.74 mmol) in dichloromethane (100 mL) and stir for 18 hours at ambient temperature. Wash solution with 1 N hydrochloric acid (3×100 mL), dry with magnesium sulfate and concentrate. Purify on silica gel with hexane/ethyl acetate mixtures to give 4.73 g (43%) of the title compound as a white solid. $MS(ES^-)$: m/z=242.1 $(M-H)^-$

Preparation 102

N-[isopropylsulfonyl]-N-[5-fluoro-2-nitrophenyl]-4-methoxybenzylamine

Suspend sodium hydride (60% in mineral oil, 0.85 g, 21.2 mmol) in tetrahydrofuran (100 mL). Add 1 N-[isopropylsulfonyl]-4-methoxy-benzylamine (4.73 g, 19.45 mmol) in tetrahydrofuran (400 mL) and heat to 70° C. Stir 10 minutes, then add 2,4-difluoronitrobenzene (3.2 mL, 29.2 mmol) in one portion and stir 18 hours at 70° C. Cool to ambient temperature and remove solvents under reduced pressure. Dissolve in ethyl acetate and wash twice with 1 N HCl aq., three times with saturated sodium hydrogen carbonate, saturated sodium carbonate, 1 N HCl aq., dry magnesium sulfate, filter and remove solvents under reduced pressure. Purify on silica gel with dichloromethane/hexane mixtures to give 5.395 g (72%) of the title compound.

Preparation 103

N-[isopropylsulfonyl]-N-[5-(2-phenylimidazol-1-yl)-2-nitrophenyl]-4-methoxybenzyl amine Dissolve N-[isopropylsulfonyl]-N-[5-fluoro-2-nitrophenyl-4-methoxybenzylamine (0.36 g, 0.94 mmol) and 2-phenyl-imidazole (0.20 g, 1.41 mmol) in N,N-dimethyl formamide (4 mL). Add sodium hydride (60% in mineral oil, 0.056 g, 1.41 mmol) and heat to 90° C. for 30 minutes. Cool to ambient temperature and remove solvents under reduced pressure. Purify on silica gel with dichloromethane/ethyl acetate mixtures to give 0.31 g (65%) of the title compound.

Preparation 104

N-[isopropylsulfonyl]-N-[5-(2-phenyl-imidazol-1-yl)-2-nitrophenyl]-amine

Cool a flask containing N-[isopropylsulfonyl]-N-[5-(2-phenylimidazol-1-yl)-2-nitrophenyl]-4-methoxybenzyl amine (0.30 g, 0.58 mmol) in an ice bath and add ice cold trifluoroacetic acid (5 mL), then warm to ambient temperature and stir for 18 hours. Remove solvent under reduced pressure. Dissolve in dichloromethane and wash with saturated sodium hydrogen carbonate, dry with magnesium sulfate, filter and purify on silica gel with dichloromethane/ethyl acetate mixtures to provide 0.21 g (92%) of 1-isopropylsulfonyl-[2-nitro-5-(2-phenyl-imidazol-1-yl)-phenyl]-amide. $MS(ES^+)$: m/z=387.1 $(M+M)^+$

Preparation 105

N-[isopropylsulfonyl]-N-[2-amino-5-(2-phenyl-imidazol-1-yl)-phenyl]-amide

Add N-[isopropylsulfonyl]-N-[5-(2-phenyl-imidazol-1-yl)-2-nitrophenyl]-amine (0.20 g, 0.52 mmol), 10% palladium on carbon (0.02 g), methanol (10 mL) and hydrogenate under a balloon of hydrogen gas for 2 hours. Filter and remove solvents under reduced pressure. Purify on silica gel with dichloromethane/ethyl acetate mixtures to give 0.12 g (63%) of the title compound. $MS(ES^+)$: m/z=357.1 $(M+H)^+$

Preparation 106

2-amino-benzothiazole-6-carboxaldehyde

Under nitrogen atmosphere, slowly add phenyl lithium (5 mL, 9.16 mmol, 2.1 equiv from a solution 1.8 M in cyclohexane/ether, 70/30) to a cold (−78° C.) solution of commercially available 2-bromo benzothiazole in 30 mL of dry THF. After the addition is complete stir the mixture for 5 minutes and add t-butyl lithium (5.6 mL, 9.16 mmol, 2.1 equiv from a solution 1.7 M in pentane). The mixture will turn from a creamy white color to green over 1 hour. At this point, rapidly add formyl piperidine (2.4 mL, 21.8 mmol, 5 equiv) dropwise and warm the mixture slowly to (>1 hour) 0° C. Quench the reaction into a mixture of cold saturated $NH_4Cl$ and extract with EtOAc. Separate the phases and back extract the organic one with more EtOAc (three times). Dry the combined organic phases over $MgSO_4$, filter and concentrate in vacuo to afford the ldehyde (50% yield).

Preparation 107

2,4-dibromonitrobenzene

Add 1,3 dibromobenzene (25 g) over sulfuric fumante acid (20 mL). Stir for 5 hours at room temperature and then pour into ice-water, extract with ethyl acetate, wash with saturated aqueous sodium chloride, dry over magnesium sulfate and concentrate under reduced pressure. Crystallize the residue with methanol to provide (26.8 g, 90%) of the desired product a light yellow solid. $MS(ES^+)$: m/z=281.90 $(M+H)^+$

Preparation 108

(5-bromo-2-nitro-phenyl)amine

In a sealed reaction tube, add cautiously 6 mL of an aqueous solution of ammonia (32%) to a solution of 2,4-dibromonitrobenzene (1,6 g) in 2 mL of DMSO. Stir for 18 hours at 100° C. and cool to room temperature. Pour the heterogeneous mixture into water and filter the title compound (1.1 g, 92%) as a yellow solid.

Preparation 109

3-amino-4-nitro-1-phenylethynyl-phenyl

Add Pd(OAc)$_2$ (31 mg), CuI (43 mg) and PPh$_3$ (48 mg) to a mixture of 5-bromo-2-nitro-phenyl amine (0.5 g) in 6 mL of Et$_3$N. Bubble nitrogen for 5 minutes and add phenylacetylene (0.37 mL). Stir the mixture at 90° C. for 1 hour and cool to room temperature. Remove triethylamine in vacuo and partition the residue between saturated aqueous sodium chloride and EtOAc. Separate the phases, dry the organic one over MgSO$_4$, filter and evaporate. Purify the residue by chromatography eluting with a 8:1 mixture of hexane:EtOAc to give the title compound (0.49 g, 90%) as a yellow solid.

Preparation 110

3-isopropylsulfonamidyl-4-nitro-1-phenylethynyl phenyl

Add isopropyl sulphonyl chloride (0.93 mL) and 1,8-diazabicyclo(5,4,0)undec-7-ene (DBU) (2.48 mL) to a solution of 3-amino-4-nitro-1-phenylethynyl-phenyl (1 g) in 40 mL of CH$_2$Cl$_2$. Stir at 45° C. for 17 hours and cool to room temperature. Dilute with more CH$_2$Cl$_2$ and wash with 10% HCl aqueous solution and water. Dry the organic phase over magnesium sulfate, and concentrate under reduced pressure. Purify the residue by silica gel chromatography, eluting with 1:1 hexane:CH$_2$Cl$_2$ to provide the title compound (0.76 g, 53%) as a yellow solid.

Preparation 111

3-isopropylsulfonamidyl-4-nitro-1-(phenyl-ethanone)-phenyl

Add 30 mL from an aqueous solution of HgO (624 mg) in 100 mL of 4% H$_2$SO$_4$ to a solution of 3-isopropylsulfonamidyl-4-nitro-1-phenylethynyl phenyl (1.48 g) in 40 mL of methanol. Stir at 100° C. for 17 hours and cool to room temperature. Neutralize the mixture with a saturated aqueous solution of NaHCO$_3$ and extract with CH$_2$Cl$_2$ (two times). Separate the phases, dry the organic phase over magnesium sulfate and concentrate under reduced pressure. Purify the residue by silica gel chromatography, eluting with 1:2 hexane:CH$_2$Cl$_2$ to provide the title compound (1.2 g, 79%) as a yellow solid. MS(ES$^-$): m/z=361.3 (M–H)$^-$.

Preparation 112

3-isopropylsulfonamidyl-4-nitro-1-(5-phenyl)-pyrazol-4-yl

Add dimethylformamide (DMF)-dimethylacetal (0.9 mL) to a stirred solution of 3-isopropylsulfonamidyl-4-nitro-1-(phenyl-ethanone)-phenyl (0.5 g) in 1.5 mL of dry DMF. Heat the mixture at 80° C. for 1 h and 45 min, cool down to room temperature and remove the solvents in vacuo. Dissolve the residue in 8 mL of EtOH and add 0.5 mL of anhydrous hydrazine. Stir for 17 hours and concentrate under reduced pressure. Purify the residue by silica gel chromatography eluting with 5% CH$_2$Cl$_2$:MeOH to provide the title compound (0.5 g, 86%) as a red solid. MS(ES$^+$) m/z=387.4 (M+H)$^+$

Preparation 113

3-isopropylsulfonamidyl-4-amino-1-(5-phenyl)-pyrazol-4-yl-phenyl

Add 10% weight Pd/C catalyst (250 mg) to a stirred suspension of nitroaniline (0.5 g) in 10 mL of EtOH. Purge the suspension with hydrogen for 5 minutes and stir the mixture under hydrogen atmosphere (1 atm) for 3 hours. Concentrate under reduced pressure and subject the residue to silica gel chromatography, eluting with 5% CH$_2$Cl$_2$: MeOH to provide the title compound (0.3 g, 70%) as a solid. MS(ES$^+$): m/z=357.1 (M+H)$^+$

Preparation 114

3-isopropylsulfonamidyl-4-nitro-1-(5-phenyl)-1,2,3-triazol-4-yl

Add sodium azide (0.033 g) to a solution of 3-isopropylsulfonamidyl-4-nitro-1-phenylethynyl (0.173 g) in 5 mL of dimethoxyethane. Heat to reflux (80° C.) for 2 hours, then cool to room temperature. Add 10 mL of 1 N hydrochloric acid and extract with ethyl acetate (20 mL) and wash with saturated aqueous sodium chloride (2×10 mL). Dry the remaining organic phase over sodium sulfate and concentrate under reduced pressure. The residue is purified by chromatography eluting with ethyl acetate:hexane (1:1) to provide (0.10 g, 50%) of the title compound as yellow solid. MS(ES$^+$): m/z=388.42 (M+H)$^+$

Preparation 115

3-isopropylsulfonamidyl-4-amino-1-(5-phenyl)-1,2,3-triazol-4-yl

Add tin(II) chloride dihydrate (0.350 g) to a mixture of 3-isopropylsulfonamidyl-4-nitro-1-(5-phenyl)-1,2,3-triazol-4-yl (0.10 g), ethanol (5 mL) and ethyl acetate (10 mL). Heat the mixture at 70° C. for 3 hours. Pour the mixture onto ice-water. Add saturated aqueous sodium bicarbonate and extract with ethyl acetate. Separate the layers, dry over sodium sulfate and concentrate under reduced pressure. Subject the residue to silica gel chromatography eluting with 1:1 ethyl acetate:hexane to provide (0.084 g, 92%) of the title compound as white solid. MS(ES$^+$): m/z=358.4 (M+H)$^+$

Preparation 116

1-dimethylaminosulfonyl-2-amino-benzimidazole

To a solution of sodium hydroxide (1.8 g) in water (9 mL) add acetonitrile (44 mL). To this solution, add 2-aminobenzimidazole (3.0 g, 22.5 mmol) and dimethylsulfamoyl chloride (2.4 mL, 22.5 mmol). Stir the reaction mixture at room temperature, overnight. Then, cool the mixture at 0° C. and the product crystallized from solution. Filter the product and dry it in vacuum to provide 5.0 g (90% yield) of the title compound as a white solid. MS(ES$^+$): m/z=241.1 (M+H)$^+$

Preparation 117

1-diethylaminosulfonyl-2-amino-6-iodobenzimidazole

Add 1-dimethylaminosulfonyl-2-amino-benzimidazole (1.0 g, 4.2 mmol) to acetic acid (10 mL) to form a solution. To this solution, add N-iodosuccinimide (0.945 g, 4.2 mmol) and heat the reaction mixture at 55° C. overnight. Cool the mixture at 0° C. and add water. The product crystallized from solution. Filter the solid and dry it in vacuum to provide 1.5 g (99%) of title compound. MS(ES$^+$): m/z=366.9 (M+H)$^+$

Preparation 118

1-dimethylaminosulfonyl-2-amino-6-(phenylethynyl)benzimidazole

Beginning with 1-dimethylaminosulfonyl-2-amino-6-iodobenzimidazole, prepare the title compound essentially as described in Preparation 52. (88% yield). MS(ES$^+$): m/z=341.0 (M+H)$^+$

Preparation 119

1-dimethylaminosulfonyl-2-amino-6-(2-phenyl-ethane-1,2-dionel)benzimidazole

Beginning with 1-dimethylaminosulfonyl-2-amino-6-(phenylethynyl)benzimidazole, prepare the title compound essentially as described in Preparation 54. (72% yield). MS(ES$^+$): m/z=373.0 (M+H)$^+$

EXAMPLE 1

1-isopropylsulfonyl-2-amino-6-(2-(thien-2-yl)-5-(phenyl)-imidazol-4-yl)-benzimidazole methanesulfonate Add thiophene-2-carboxaldehyde (3.16 mL, 33.8 mmol) to a stirring mixture of 1-isopropylsulfonyl-2-amino-6-(α-((tert-butyldimethylsilyl)oxy)-α-(phenyl)acetyl)-benzimidazole (15.0 g, 30.8 mmol), copper(II) acetate (11.2 g, 61.5 mmol), and ammonium acetate (23.7 g, 308 mmol) in acetic acid (300 mL). Heat the mixture at 95-100° C. and stir vigorously for 2 hours. Cool the mixture to 15° C., pour into a mixture of 750 mL saturated aqueous ammonium chloride and 250 mL concentrated ammonium hydroxide. Adjust the mixture to pH 10 with ammonium hydroxide precooled to 5° C. and then add 4 L 4:1 ethyl acetate:methanol. Separate the layers and wash the organic layer with saturated aqueous ammonium chloride (500 mL), dry over magnesium sulfate and concentrate under reduced pressure. Subject the residue to silica gel chromatography eluting with dichloromethane containing from 15-50% acetonitrile and 0.5% triethylamine. Suspend the recovered material in ethanol (75 mL), warm to 55-60° C. for 30 minutes, cool to −10° C. for 30 minutes, filter, wash sequentially with cold ethanol followed by diethyl ether. Dry under reduced pressure to provide the title compound in 40% yield as a dark yellow powder. MS(ES$^+$): m/z=464.1 (M+H)$^+$ To a homogeneous solution of 1-isopropylsulfonyl-2-amino-6-(2-(thien-2-yl)-5-(phenyl)-imidazol-4-yl)-benzimidazole (0.4 g, 0.86 mmol) in 10% methanol/dichloromethane (10 mL) add 1 N solution of methane sulfonic acid in the same reaction mixture (10% methanol/dichloromethane) (0.86 mL, 1 equivalent). Stir the mixture at room temperature for 2 hours, remove the solvents under reduced pressure, triturate the residue and stir with diethyl ether (80 mL) for 3 hours. Filter the solid and dry under vacuum to yield a pale cream solid. 97% Yield. MS (ES$^+$): m/z=464.1 (M+H)$^+$.

The compounds of Examples 2-62 may be prepared essentially as described in Example 1 as either the free base or the methanesulfonate salt. The dimethanesulfonate salt can also be prepared using essentially the same procedure described in Example 1 with 2.0 equivalents of methanesulfonic acid.

| Example | Compound | MS(ES$^+$): m/z |
| --- | --- | --- |
| 2 | 1-isopropylsulfonyl-2-amino-6-(2-(thien-2-yl)-5-(4-fluorophenyl)-imidazol-4-yl)-benzimidazole | 480.1 (M + H)$^+$ |
| 3 | 1-isopropylsulfonyl-2-amino-6-(2-(thien-2-yl)-5-(3-trifluorophenyl)-imidazol-4-yl)-benzimidazole | 532.0 (M + H)$^+$ |
| 4 | 1-isopropylsulfonyl-2-amino-6-(2-(thien-2-yl)-5-(4-trifluorophenyl)-imidazol-4-yl)-benzimidazole | 532.1 (M + H)$^+$ |
| 5 | 1-isopropylsulfonyl-2-amino-6-(2-(5-nitrothien-2-yl)-5-(phenyl)-imidazol-4-yl)-benzimidazole | 507.1 (M + H)$^+$ |
| 6 | 1-isopropylsulfonyl-2-amino-6-(5-(phenyl)-imidazol-4-yl)-benzimidiazole | 382.2 (M + H)$^+$ |
| 7 | 1-isopropylsulfonyl-2-amino-6-(5-(4-fluorophenyl)-imidazol-4-yl)-benzimidazole dimethanesulfonate | 400.1 (M + H)$^+$ |
| 8 | 1-isopropylsulfonyl-2-amino-6-(5-(3-trifluoromethyl)-imidazol-4-yl)-benzimidazole | 450.2 (M + H)$^+$ |

-continued

| Example | Compound | MS(ES+): m/z |
|---|---|---|
| 9 | 1-isopropylsulfonyl-2-amino-6-(2,5-(diphenyl)-imidazol-4-yl)-benzimidazole | 458.5 (M + H)+ |
| 10 | 1-isopropylsulfonyl-2-amino-6-(2-(2-chlorophenyl)-5-(phenyl)-imidazol-4-yl)-benzimidazole | 492.0 (M + H)+ |
| 11 | 1-isopropylsulfonyl-2-amino-6-(2-(3-chlorophenyl)-5-(phenyl)-imidazol-4-yl)-benzimidazole | 492.0 (M + H)+ |
| 12 | 1-isopropylsulfonyl-2-amino-6-(2-(4-chlorophenyl)-5-(phenyl)-imidazol-4-yl)-benzimidazole | 492.0 (M + H)+ |
| 13 | 1-isopropylsulfonyl-2-amino-6-(2-(4-methoxyphenyl)-5-(phenyl)-imidazol-4-yl)-benzimidazole | 487.8 (M + H)+ |
| 14 | 1-isopropylsulfonyl-2-amino-6-(2-(4-nitrophenyl)-5-(phenyl)-imidazol-4-yl)-benzimidazole | 502.8 (M + H)+ |
| 15 | 1-isopropylsulfonyl-2-amino-6-(2-(4-dimethylaminophenyl)-5-(phenyl)-imidazol-4-yl)-benzimidazole | 501.5 (M + H)+ |
| 16 | 1-isopropylsulfonyl-2-amino-6-(2-(pyridin-4-yl)-5-(phenyl)-imidazol-4-yl)-benzimidazole | 459.1 (M + H)+ |
| 17 | 1-isopropylsulfonyl-2-amino-6-(2-(thiazol-2-yl)-5-(phenyl)-imidazol-4-yl)-benzimidazole | 464.9 (M + H)+ |
| 18 | 1-isopropylsulfonyl-2-amino-6-(2-(1-(ethoxycarbonyl)ethen-2-yl)-5-(phenyl)-imidazol-4-yl)-benzimidazole | 480.4 (M + H)+ |
| 19 | 1-isopropylsulfonyl-2-amino-6-(2-(1-(tert-butoxycarbonyl)piperidin-4-yl)-5-(phenyl)-imidazol-4-yl)-benzimidazole | 565.3 (M + H)+ |
| 20 | 1-isopropylsulfonyl-2-amino-6-(2-(1-(tert-butoxycarbonyl)piperidin-4-yl)-5-(4-fluorophenyl)-imidazol-4-yl)-benzimidazole | 583.2 (M + H)+ |
| 21 | 1-isopropylsulfonyl-2-amino-6-(2-(1-(benzyloxycarbonyl)piperidin-4-yl)-5-(phenyl)-imidazol-4-yl)-benzimidazole | 599.2 (M + H)+ |
| 22 | 1-isopropylsulfonyl-2-amino-6-(2-(benzo(1,3)-dioxolan-5-yl)-5-(phenyl)-imidazol-4-yl)-benzimidazole methanesulfonate | 502.2 (M + H)+ |
| 23 | 1-isopropylsulfonyl-2-amino-6-(2-(5-ethylthiophen-2-yl)-5-(4-fluorophenyl)-imidazol-4-yl)-benzimidazole methanesulfonate | 510.1 (M + H)+ |
| 24 | 1-isopropylsulfonyl-2-amino-6-(2-(2,6-dichlorophenyl)-5-(4-fluorophenyl)-imidazol-4-yl)-benzimidazole methanesulfonate | 544.1 (M + H)+ |
| 25 | 1-isopropylsulfonyl-2-amino-6-(2-(4-(pyrrolidin-1-yl)-1-phenyl)-5-(phenyl)-imidazol-4-yl)-benzimidazole | 527.2 (M + H)+ |
| 26 | 1-isopropylsulfonyl-2-amino-6-(2-(2-(morpholin-4-yl)-phenyl)-5-(phenyl)-imidazol-4-yl)-benzimidazole | 543.3 (M + H)+ |
| 27 | 1-isopropylsulfonyl-2-amino-6-(2-(4-methylpiperazin-1-yl)-phenyl)-5-(phenyl)-imidazol-4-yl)-benzimidazole | 556.3 (M + H)+ |
| 28 | 1-isopropylsulfonyl-2-amino-6-(2-(2,6-difluorophenyl)-5-(4-fluorophenyl)-imidazol-4-yl)-benzimidazole | 512.1 (M + H)+ |
| 29 | 1-isopropylsulfonyl-2-amino-6-(2-(2,4-difluorophenyl)-5-(phenyl)-imidazol-4-yl)-benzimidazole | 494.2 (M + H)+ |
| 30 | 1-isopropylsulfonyl-2-amino-6-(2-(cyclohexyl)-5-(phenyl)-imidazol-4-yl)-benzimidazole | 464.2 (M + H)+ |
| 31 | 1-isopropylsulfonyl-2-amino-6-(2-(cyclohexyl)-5-(4-fluorophenyl)-imidazol-4-yl)-benzimidazole | 482.2 (M + H)+ |
| 32 | 1-isopropylsulfonyl-2-amino-6-(2-(tert-butyl)-5-(phenyl)-imidazol-4-yl)-benzimidazole | 438.2 (M + H)+ |
| 33 | 1-isopropylsulfonyl-2-amino-6-(2-(tetrahydropyran-4-yl)-5-(phenyl)-imidazol-4-yl)-benzimidazole | 466.2 (M + H)+ |
| 34 | 1-isopropylsulfonyl-2-amino-6-(2-(tetrahydropyran-4-yl)-5-(4-fluorophenyl)-imidazol-4-yl)-benzimidazole | 484.2 (M + H)+ |
| 35 | 1-isopropylsulfonyl-2-amino-6-(2-(3,5-difluorophenyl)-5-(phenyl)-imidazol-4-yl)-benzimidazole | 494.2 (M + H)+ |
| 36 | 1-isopropylsulfonyl-2-amino-6-(2-(4-trifluoromethylphenyl)-5-(phenyl)-imidazol-4-yl)-benzimidazole | 526.2 (M + H)+ |
| 37 | 1-isopropylsulfonyl-2-amino-6-(2-(2-trifluoromethoxyphenyl)-5-(phenyl)-imidazol-4-yl)-benzimidazole | 542.2 (M + H)+ |
| 38 | 1-isopropylsulfonyl-2-amino-6-(2-(2,3-difluorophenyl)-5-(phenyl)-imidazol-4-yl)-benzimidazole | 494.2 (M + H)+ |
| 39 | 1-isopropylsulfonyl-2-amino-6-(2-(2-trifluoromethylphenyl)-5-(phenyl)-imidazol-4-yl)-benzimidazole | 526.2 (M + H)+ |
| 40 | 1-isopropylsulfonyl-2-amino-6-(2-(4-tolylphenyl)-5-(phenyl)-imidazol-4-yl)-benzimidazole dimethanesulfonate | 472.2 (M + H)+ |

-continued

| Example | Compound | MS(ES+): m/z |
|---------|----------|--------------|
| 41 | 1-isopropylsulfonyl-2-amino-6-(2-(4-acetylaminophenyl)-5-(phenyl)-imidazol-4-yl)-benzimidazole methanesulfonate | 515.2 (M + H)+ |
| 42 | 1-isopropylsulfonyl-2-amino-6-(2-(fluorophenyl)-5-(phenyl)-imidazol-4-yl)-benzimidazole dimethanesulfonate | 476.2 (M + H)+ |
| 43 | 1-isopropylsulfonyl-2-amino-6-(2-(tert-butyl)-5-(4-fluorophenyl)-imidazol-4-yl)-benzimidazole | 456.3 (M + H)+ |
| 44 | 1-isopropylsulfonyl-2-amino-6-(2-(benzyloxymethyl)-5-(phenyl)-imidazol-4-yl)-benzimidazole | 502.2 (M + H)+ |
| 45 | 1-isopropylsulfonyl-2-amino-6-(2-(thien-3-yl)-5-(4-fluorophenyl)-imidazol-4-yl)-benzimidazole dimethanesulfonate | 464.58 (M + H)+ |
| 46 | 1-isopropylsulfonyl-2-amino-6-(2-(5-chloro-thien-2-yl)-5-(phenyl)-imidazol-4-yl)-benzimidazole methanesulfonate | 499.03 (M + H)+ |
| 47 | 1-isopropylsulfonyl-2-amino-6-(2-(5-chloro-thien-2-yl)-5-(4-fluorophenyl)-imidazol-4-yl)-benzimidazole methanesulfonate | 517.02 (M + H)+ |
| 48 | 1-isopropylsulfonyl-2-amino-6-(2-(pyridin-3-yl)-5-(phenyl)-imidazol-4-yl)-benzimidazole dimethanesulfonate | 459.55 (M + H)+ |
| 49 | 1-isopropylsulfonyl-2-amino-6-(2-(imidazol-2-yl)-5-(phenyl)-imidazol-4-yl)-benzimidazole | 448.52 (M + H)+ |
| 50 | 1-isopropylsulfonyl-2-amino-6-(2-(2-chloro-6-fluorophenyl)-5-(phenyl)-imidazol-4-yl)-benzimidazole dimethanesulfonate | 510.1 (M + H)+ |
| 51 | 1-isopropylsulfonyl-2-amino-6-(2-(2-chloro-6-fluorophenyl)-5-(4-fluorophenyl))-imidazol-4-yl)-benzimidazole methanesulfonate | 528.1 (M + H)+ |
| 52 | 1-isopropylsulfonyl-2-amino-6-(2-(2-fluoro-6-trifluoromethylphenyl)-5-(phenyl)-imidazol-4-yl)-benzimidazole methanesulfonate | 544.2 (M + H)+ |
| 53 | 1-isopropylsulfonyl-2-amino-6-(2-(2-fluoro-4-nitrophenyl)-5-(phenyl)-imidazol-4-yl)-benzimidazole methanesulfonate | 521.55 (M + H)+ |
| 54 | 1-isopropylsulfonyl-2-amino-6-(2-(2,5-difluorophenyl)-5-(phenyl)-imidazol-4-yl)-benzimidazole dimethanesulfonate | 494.54 (M + H)+ |
| 55 | 1-isopropylsulfonyl-2-amino-6-(2-(4-chloro-2-fluorophenyl)-5-(phenyl)-imidazol-4-yl)-benzimidazole methanesulfonate | 510.1 (M + H)+ |
| 56 | 1-isopropylsulfonyl-2-amino-6-(2-(2-chlorophenyl)-5-(phenyl)-imidazol-4-yl)-benzimidazole methanesulfonate | 493.00 (M + H)+ |
| 57 | 1-isopropylsulfonyl-2-amino-6-(2-(4-trifluoromethoxyphenyl)-5-(phenyl)-imidazol-4-yl)-benzimidazole dimethanesulfonate | 542.56 (M + H)+ |
| 58 | 1-isopropylsulfonyl-2-amino-6-(2-(2-methylphenyl)-5-(phenyl)-imidazol-4-yl)-benzimidazole methanesulfonate | 472.59 (M + H)+ |
| 59 | 1-isopropylsulfonyl-2-amino-6-(2-(4-methylsulfonamidophenyl)-5-(phenyl)-imidazol-4-yl)-benzimidazole methanesulfonate | 551.66 (M + H)+ |
| 60 | 1-isopropylsulfonyl-2-amino-6-(2-(4-methylsulfonylphenyl)-5-(phenyl)-imidazol-4-yl)-benzimidazole dimethanesulfonate | 554.64 (M + H)+ |

| Example | Compound | MS(ES+): m/z |
|---|---|---|
| 61 | 1-isopropylsulfonyl-2-amino-6-(2-(2-fluoro-4-methylaminophenyl)-5-(phenyl)-imidazol-4-yl)-benzimidazole | 505.59 (M + H)+ |
| 62 | 1-isopropylsulfonyl-2-amino-6-(2-(2,6-difluoro-4-(pyrrolidin-1-yl-ethoxy)-phenyl)-5-(phenyl)-imidazol-4-yl)-benzimidazole dimethanesulfonate | 607.70 (M + H)+ |

EXAMPLE 63

1-isopropylsulfonyl-2-amino-6-(2-(2-fluoro-4-aminophenyl)-5-(phenyl)-imidazol-4-yl)-benzimidazole Reflux a mixture of 1-isopropylsulfonyl-2-amino-6-(2-(2-fluoro-4-nitrophenyl)-5-(phenyl)-imidazol-4-yl)-benzimidazole (0.59 g), ammonium formate (0.29 g) and Pd/C (10%, 0.12 g) in ethanol (20 mL) at 95° C. for 6 hours. Filter over Celite® and concentrate filtrate under reduced pressure to provide the title compound (0.41 g, 75%). MS(ES+): m/z=491.2 (M+H)+

EXAMPLE 64

1-isopropylsulfonyl-2-amino-6-(2-((4-ethylamino)phenyl)-5-(phenyl)-imidazol-4-yl)-benzimidazole To a solution of 1-isopropylsulfonyl-2-amino-6-(α-((tert-butyldimethylsilyl)oxy)-α-(phenyl)acetyl)benzimidazole (1.16 g, 2.37 mmol) in 20 mL of glacial acetic acid add copper II acetate (861 mg, 4.74 mmol), ammonium acetate (2.92 g, 28.44 mmol) and 4-(N-tert-butoxycarbonyl-N-ethyl-amino) benzaldehyde (630 mg, 2.84 mmol). Stir the reaction mixture at 80° C. for 3 hours. Concentrate the solvent and dissolve the residue in ethyl acetate/methanol (20%), pour in 3:1 saturated aqueous ammonium chloride solution/ammonia 30%, and extract with ethyl acetate; wash the organic layers with saturated ammonium chloride, saturated aqueous sodium chloride, dry over sodium sulphate and concentrate. Dissolve 1.43 g of residue in 40 mL of dichloromethane and add 1.82 mL of trifluoroacetic acid (TFA). Stir the mixture at room temperature under argon atmosphere for 3 hours. Then, concentrate the solvent, dissolve the residue in ethyl acetate/methanol (20%), and wash with saturated sodium bicarbonate and saturated aqueous sodium chloride, dry over sodium sulphate and concentrate. Purify the obtained solid by chromatography eluting with dichloromethane/methanol (2%) to obtain 273 mg of title compound. Yield 27%. MS(ES+): m/z=501.2 (M+H)+

EXAMPLE 65

1-isopropylsulfonyl-2-amino-6-(2-(4-(2-(piperidin-1-yl)-ethoxy)phenyl)-5-(phenyl)-imidazol-4-yl)-benzimidazole trifluoroacetate To a solution of 4-(2-piperidin-1-yl)-ethoxybenzaldehyde (0.42 g, 1.8 mmol) in acetic acid (18 mL) (Kaliappa G., *Tetrahedron Letter*, 34(35), 5631-4, (1993)) add 1-(isopropylsulfonyl)-2-amino-6-(α-((tert-butyldimethylsilyl)oxy)-α-(phenyl)acetyl)benzimidazole (0.88 g, 1.8 mmol), ammonium acetate (1.39 g, 18 mmol), copper (II) acetate (0.65 g, 3.6 mmol) under nitrogen. Heat the resulting reaction mixture to 100° C. and stir for 2 hours. Cool to room temperature, and then concentrate the acetic acid. Dissolve the residue in methanol, pass the methanol solution through a SCX column, wash with methanol, then 2 N ammonia in methanol. Concentrate the solvent. Purify the residue by HPLC to give title compound as the trifluoroacetic acid salt (0.17 g, 23%). MS(ES+) m/z=585.3 (M+H)+

The compounds of Examples 66-75 may be prepared essentially as described in Example 65.

| EXAMPLE | Compound | MS(ES+): m/z |
|---|---|---|
| 66 | 1-isopropylsulfonyl-2-amino-6-(2-(4-(2-(dimethylamino)-ethoxy)phenyl)-5-(phenyl)-imidazol-4-yl)-benzimidazole trifluoroacetate | 545.4 (M + H)+ |
| 67 | 1-isopropylsulfonyl-2-amino-6-(2-(3-(2-(morpholino-4-yl)-ethoxy)phenyl)-5-(phenyl)-imidazol-4-yl)-benzimidazole trifluoroacetate | 587.4 (M + H)+ |
| 68 | 1-isopropylsulfonyl-2-amino-6-(2-(3-(2-(azepin-4-yl)-ethoxy)phenyl)-5-(phenyl)-imidazol-4-yl)-benzimidazole trifluoroacetate | 599.4 (M + H)+ |
| 69 | 1-isopropylsulfonyl-2-amino-6-(2-(3-(2-(pyrrolidin-1-yl)-ethoxy)phenyl)-5-(phenyl)-imidazol-4-yl)-benzimidazole trifluoroacetate | 571.4 (M + H)+ |
| 70 | 1-isopropylsulfonyl-2-amino-6-(2-(3-(2-dimethylamino)-ethoxy)phenyl)-5-(phenyl)-imidazol-4-yl)-benzimidazole trifluoroacetate | 545.4 (M + H)+ |
| 71 | 1-isopropylsulfonyl-2-amino 6-(2-(3-(2-(diethylamino)-ethoxy)phenyl)-5-(phenyl)-imidazol-5-yl)-benzimidazole trifluoroacetate | 573.4 (M + H)+ |

-continued

| EXAMPLE | Compound | MS(ES+): m/z |
|---|---|---|
| 72 | 1-isopropylsulfonyl-2-amino-6-(2-(3-(2-(piperidin-1-yl)-ethoxy)phenyl)-5-(phenyl)-imidazol-4-yl)-benzimidazole trifluoroacetate | 585.4 (M + H)+ |
| 73 | 1-isopropylsulfonyl-2-amino-6-(2-(4-(3-(dimethylamino)-propoxy)-3-fluorophenyl)-5-(phenyl)-imidazol-4-yl)-benzimidazole trifluoroacetate | 577.4 (M + H)+ |
| 74 | 1-isopropylsulfonyl-2-amino-6-(2-(3-fluoro-4-(2-(morpholino-4-yl)-ethoxy)phenyl)-5-(phenyl)-imidazol-4-yl)-benzimidazole trifluoroacetate | 605.4 (M + H)+ |
| 75 | 1-isopropylsulfonyl-2-amino-6-(2-(3-fluoro-4-(2-(pyrrolidin-1-yl)-ethoxy)phenyl)-5-(phenyl)-imidazol-4-yl)-benzimidazole trifluoroacetate | 589.4 (M + H)+ |

EXAMPLE 76

1-isopropylsulfonyl-2-amino-6-(2-(2,6-difluorophenyl)-5-(phenyl)-oxazol-4-yl)-benzimidazole To a solution of 1-isopropylsulfonyl-2-amino-6-(α-((tert-butyldimethylsilyl)oxy)-α-(phenyl)acetyl)-benzimidazole (5.84 g, 12.0 mmol) in acetic acid (glacial, 100 mL) add ammonium acetate (9.26 g, 120 mmol) and copper (I) acetate (4.31 g, 23.7 mmol), followed by 2,6-difluorobenzaldehyde (1.41 mL, 13.1 mmol), and stir the mixture at 100° C. for 4 hours. Cool the mixture to 0° C. and slowly pour over a mixture of $NH_4Cl/NH_4OH$ 3:1, pH=9. Dilute the mixture with $H_2O$ (200 mL), extract with EtOAc (3×200 mL), wash with saturated aqueous NaCl (150 mL), dry ($Na_2SO_4$), and concentrate in vacuo. Purify the residue in a biotage system (eluent:$CH_2Cl_2$/MeCN 5:1), and then by HPLC, to afford a yellow solid, 675 mg, 11% yield. MS(ES+): m/z=495.0 (M+H)+

EXAMPLE 77

1-isopropylsulfonyl-2-amino-6-(2-(2,6-difluorophenyl)-5-(phenyl)-imidazol-4-yl)-benzimidazole and 1-isopropylsulfonyl-2-amino-6-(2-(2,6-difluorophenyl)-5-(phenyl)-imidazol-4-yl)-benzimidazole ethanolate Under a nitrogen atmosphere, combine 1-isopropylsulfonyl-2-amino-6-(diketo-(2-phenyl)ethyl)-benzimidazole (225 g, 0.606 moles), $NH_4OAc$ (700.4 g, 9.08 moles), butanol (4.5 L), and 2,6-diflurorobenzaldehyde (172.2 g, 1.212 moles). Heat the resulting mixture to 55° C. to give a yellow slurry. Cool the reaction mixture to 15° C. and add water (2.5 L). After mixing for 15 minutes, separate the layers and back extract the organic phase with water (2.5 L). Separate the organic phase and concentrate under vacuum at 55° C. to give 513 grams of black oil. Dissolve the oil in MeOH (505 mL) at 5° C., and add methyl tert-butyl ether (MTBE) (2.25 L) to the mixture over 1.5 hours. Cool the the resulting slurry slowly to 22° C. and stir overnight. Filter the light brown solids and wash with MTBE (750 mL). Pull house vacuum on the solids for 1.5 hours to give 239 g of solid. Dissolve the solids in EtOAc (3.85 L) at 50° C., and add silica gel (250 g) to the mixture. After 0.5 hour, cool the mixture to cool to 35° C., vacuum filter over silica gel (250 g wet with EtOAc), and rinse through with EtOAc (6 L). Concentrate the resulting mixture under vacuum at 50° C. to give a light brown solid (233.6 g, 78%; HPLC >99 area %; ¹H NMR indicates EtOAc included in the solid; DSC onset 106.65° C., maximum 116.79° C., 18.67 J/g).

Prepare the ethanolate compound as follows: Dissolve 395 g of compound in EtOH (2 L) at 53° C. and vacuum distill to dryness (this procedure may be repeated to remove residual EtOAc from the compound; and may be confirmed by ¹HNMR). Slurry the resulting solids in EtOH (1.185 L) at 50° C. for a few minutes and slowly cool to 22° C. overnight. Cool the resulting slurry to −3 to 0° C. and hold for 1 hour. Filter the resulting crystals, wash with EtOH (395 mL, 0° C.), and dry under vacuum at 50° C. to constant weight. Isolate the ethanol solvate (324 g, 84%) as a light pinkish solid. HPLC indicates the product to be 99.5 area % pure. MS(ES+) m/z=492.3 (M+H)+

EXAMPLE 78

1-isopropylsulfonyl-2-amino-6-(2-(2,6-difluorophenyl)-5-(phenyl)-imidazol-4-yl)-benzimidazole 1,5 napthalene disulfonate Weigh out 247 mg of the free base and suspend in 4 mL 95% EtOH. Separately dissolve 181 mg of 1,5 naphthalenedisulfonic acid tetrahydrate in 2 mL of 95% EtOH. Add the acid solution to the suspension in 0.2 mL increments over a 5 minute interval with mixing in between additions. Seed the solution with crystals obtained from a recently run salt selection screen and within a few minutes precipitation occurs. Allow the vial to stand for 2 hours with occasional shaking. Filter the precipitate and air-dry to obtain 325 mg of off-white crystals.

Seeds for the napadisylate are made in the following manner:

A salt screen matrix of 24 counterions and 4 solvents is setup using Library Design™ software developed by Symyx Technologies, Inc. The free base solution and counterion solutions are added using a Cavro™ liquid handler. Liquids are then removed using a Genvac™ vacuum centrifuge. The solids are then run on Symyx automated crystallization equipment which: 1) adds solvents to the wells, 2) heats, 3) filters and; 4) adds filtrate to separate crystallization stations (evaporation, precipitation, and cooling). From these separate processing stations it was found that small amounts (<2 mg) of crystalline material for the napadisylate salt were present on the glass plates. Solvent systems, which gave crystalline material, were 95% ethanol and ethyl acetate.

EXAMPLE 79

1-cyclopentylsulfonyl-2-amino-6-(2-(2,6-difluorophenyl)-5-(phenyl)-imidazolyl-4-yl)-benzimidazole Beginning with 1-cyclopentylsulfonyl-2-amino-6-(diketo-(2-phenylethyl))-benzimidazole (1.29 g) prepare essentially as described in Example 77 to obtain 0.46 g (28% yield) as a yellow solid. MS(APC$^+$), m/z=520.2 (M+H)$^+$. Prepare the dimethanesulfonate starting from 0.23 g of the free base to yield 0.25 g (78% yield) as a white solid. MS (ion trap/ES$^+$): m/z=520.1 (M+H)$^+$ The compounds of Examples 80-84 may be prepared essentially as described in Example 77 as the free base. The methanesulfonate or dimethanesulfonate salt can also be prepared at will using essentially the same procedure of Example 1 and 1.0 or 2.0 equivalents of methanesulfonic acid.

| Example | Compound | MS(ES$^+$): m/z |
|---|---|---|
| 80 | 1-isopropylsulfonyl-2-amino-6-(2-(5-ethylthien-2-yl)-5-(phenyl)-imidazol-4-yl)-benzimidazole methanesulfonate | 492.0 (M + H)$^+$ |
| 81 | 1-isopropylsulfonyl-2-amino-6-(2-(2,6-dichlorophenyl)-5-(phenyl)-imidazol-4-yl)-benzimidazole methanesulfonate | 526.1 (M + H)$^+$ |
| 82 | 1-isopropylsulfonyl-2-amino-6-(2-(3-trifluoromethylphenyl)-5-(phenyl)-imidazol-4-yl)-benzimidazole | 526.2 (M + H)$^+$ |
| 83 | 1-isopropylsulfonyl-2-amino-6-(2-(2-trifluoromethylsulfanylphenyl)-5-(phenyl)-imidazol-4-yl)-benzimidazole dimethanesulfonate | 558.1 (M + H)$^+$ |
| 84 | 1-isopropylsulfonyl-2-amino-6-(2-(3-methylthien-2-yl)-5-(phenyl)-imidazol-4-yl)-benzimidazole methanesulfonate | 478.2 (M + H)$^+$ |

EXAMPLE 85

1-isopropylsulfonyl-2-amino-6-(2-(isopropyl)-5-(4-fluorophenyl)-imidazolyl-4-yl)-benzimidazole methanesulfonate Add isobutyraldehyde (0.25 mL, 3.3 mmol) to a stirring mixture of 1-(6-(1-isopropylsulfonyl)-2-amino benzimidazole)-2-(4-fluoro)phenyl-ethane-1,2-dione (0.5 g, 1.28 mmol) and ammonium acetate (1.48 g, 19.2 mmol) in n-BuOH (10 mL). Heat the mixture at 80-90° C. and stir vigorously for 2 hours in a sealed tube. Cool the mixture to room temperature and concentrate under reduced pressure. Add ethyl acetate and wash with water. Separate the layers and wash the organic layer with saturated aqueous sodium chloride (50 mL), dry over magnesium sulfate and concentrate under reduced pressure. Subject the residue to silica gel chromatography (biotage) eluting with 40:1 to 20:1 dichloromethane:methanol to provide 1-isopropylsulfonyl-2-amino-6-(2-(isopropyl)-5-(4-fluorophenyl)-imidazol-4-yl)-benzimidazole MS(ES$^+$): m/z=442.1 (M+H)$^+$ Suspend the recovered 1-isopropylsulfonyl-2-amino-6-(2-(isopropyl)-5-(4-fluorophenyl)-imidazol-4-yl)-benzimidazole in diethyl ether, filter, wash with cold diethyl ether. Dry under reduced pressure to provide the title compound in 59% as a white powder. MS(ES$^+$): m/z=442.1 (M+H)$^+$ Add methanesulfonic acid (0.68 mL, 1 M in dichloromethane:methanol 95:5 freshly prepared) at once to a solution of 1-isopropylsulfonyl-2-amino-6-(2-(isopropyl)-5-(4-fluorophenyl)-imidazol-4-yl)-benzimidazole (0.299 g, 0.68 mmol) in dichloromethane:methanol 10 mL, 95:5). After 5 minutes, remove the solvent by nitrogen steam and finish dry it under vacuum. Triturate the crude material with diethyl ether (20 mL) overnight. Collect the salt by filtration and wash it with additional diethyl ether to provide 0.353 mg (97% yield) of the title compound. MS(ES$^+$): m/z=442.1 (M+H)$^+$

EXAMPLE 86

1-isopropylsulfonyl-2-amino-6-(2-(isopropyl)-5-(phenyl)-imidazol-4-yl)-benzimidizole methanesulfonate Add isobutyraldehyde (0.73 mL, 8.1 mmol) to a stirring mixture of 1-isopropylsulfonyl-2-amino-6-(diketo-(2-phenyl)ethyl)) benzimidazole (1.5 g, 4.04 mmol), and ammonium acetate (3 g, 40.4 mmol) in acetic acid (20 mL). Heat the mixture at 80-90° C. and stir vigorously for 2 hours in a sealed tube. Cool the mixture to room temperature and concentrate under reduced pressure. Add ice and stir the mixture 15 minutes vigorously. Add a pre-cooled (ice-bath) mixture 4/1 (v/v) of saturated aqueous ammonium chloride/concentrated ammonium hydroxide (50 mL). Add 125 mL 4:1 ethyl acetate:methanol. Separate the layers and wash the organic layer with saturated aqueous ammonium chloride (50 mL), dry over magnesium sulfate, and concentrate under reduced pressure. Subject the residue to silica gel chromatography eluting with 25:1 dichloromethane:methanol to provide 1-isopropylsulfonyl-2-amino-6-(2-(isopropyl)-5-(phenyl)-imidazol-4-yl)-benzimidizole. MS(ES$^+$): m/z=424.1 (M+H)$^+$ Suspend the recovered 1-isopropylsulfonyl-2-amino-6-(2-(isopropyl)-5-(phenyl)-imidazol-4-yl)-benzimidizole in diethyl ether, filter, wash with cold diethyl ether. Dry under reduced pressure to provide the free base in 28% as a white powder. MS(ES$^+$): m/z=424.1 (M+H)$^+$ Add methanesulfonic acid (0.2 mL, 1 M in $CH_2Cl_2$: MeOH 95:5 recently prepared) at once to a solution of 1-isopropylsulfonyl-2-amino-6-(2-(isopropyl)-5-(phenyl)-imidazol-4-yl)-benzimidizole (90 mg, 0.2 mmol) in $CH_2Cl_2$:MeOH 8:10 mL, 95:5). After 5 minutes, remove the solvent by nitrogen steam and finish drying it under vacuum. Triturate the crude material with diethyl ether (20 mL) overnight. Collect the salt by filtration and wash it with additional diethyl ether to provide 88 mg (81% yield) of the title compound.

The compounds of Examples 87-93 may be prepared essentially as described in Examples 85 and 86.

| Example | Compound | MS (ES+): m/z |
|---|---|---|
| 87 | 1-isopropylsulfonyl-2-amino-6-(2-(2,2-dimethylpropyl)-5-(4-fluorophenyl)-imidazol-4-yl)-benzimidazole methanesulfonate | 470.1 (M + H)+ |
| 88 | 1-isopropylsulfonyl-2-amino-6-(2-(methyl)-5-(phenyl)-imidazol-4-yl)-benzimidazole dimethanesulfonate | 396.1 (M + H)+ |
| 89 | 1-isopropylsulfonyl-2-amino-6-(2-(methyl)-5-(4-fluorophenyl)-imidazol4-yl)-benzimidazole methanesulfonate | 414.1 (M + H)+ |
| 90 | 1-isopropylsulfonyl-2-amino-6-(2-(trifluoromethyl)-5-(phenyl)-imidazol-4-yl)-benzimidazole methanesulfonate | 450.1 (M + H)+ |
| 91 | 1-isopropylsulfonyl-2-amino-6-(2-(ethyl)-5-(4-fluorophenyl)-imidazol-4-yl)-benzimidazole methanesulfonate | 428.1 (M + H)+ |
| 92 | 1-isopropylsulfonyl-2-amino-6-(2-(cyclopropyl)-5-(4-fluorophenyl)-imidazol-4-yl)-benzimidazole methanesulfonate | 440.1 (M + H)+ |
| 93 | 1-dimethyLaminosulfonyl-2-amino-6-(2-(2,6-difluorophenyl)-5-(phenyl)-imidazol-4-yl)-benzimidazole methanesulfonate | 495.1 (M + H)+ |

EXAMPLE 94

1-isopropylsulfonyl-2-amino-6-(2-(formyl)-5-(phenyl)-imidazol-4-yl)-benzimidazole Add to a solution of 1-isopropylsulfonyl-2-amino-6-(1-(trimethylsilylethoxymethyl)-2-(formyl)-5-(phenyl)-imidazolyl)-benzimidazole (100 mg, 0.185 mmol) in ethanol (4 mL) HCl (37%, 4 mL) and stir at room temperature for 4 hours. Dilute the mixture with water (20 mL) and wash with EtOAc (3×10 mL). Add to the aqueous phase NaOH (15%) until pH=6-7 and extract the mixture with EtOAc (3×20 mL). Dry (MgSO$_4$) the combined organic layers and concentrate in vacuo. Purify the residue in solid phase extraction (SPE) cartridge (Oasis™) and then by HPLC to obtain a white solid, 8 mg, 10% yield. MS(ES+): m/z=410 (M+H)+

EXAMPLE 95

1-isopropylsulfonyl-2-amino-6-(2-(2-(piperidin-1-yl) methyl)-5-(phenyl)-imidazol-4-yl) -benzimidazole A. Reductive Amination To a solution of 1-isopropylsulfonyl-2-amino-6-(1-(trimethylsilylethoxymethyl)-2-(formyl)-5-(phenyl)-imidazol-4-yl)-benzimidazole (200 mg, 0.37 mmol) and piperidine (0.037 mL, 0.37 mmol) in 1,2-dichloroethane (5 mL) add sodium triacetoxyborohydride (110 mg, 0.52 mmol) in one portion and stir at room temperature for 5 hours. Then, add water (50 mL) and extract with EtOAc (3×50 mL). Wash the combined organic layers with saturated aqueous sodium chloride (50 mL), dry (MgSO$_4$), and concentrate in vacuo to obtain a yellow solid, 1-isopropylsulfonyl-2-amino-6-(1-(trimethylsilylethoxymethyl)-2-((2-piperidin-1-yl)methyl)-5-(phenyl)-imidazole-4-yl)-benzimidazole, 251 mg. MS(ES+): m/z=609.2 (M+H)+

B. Deprotection

To a solution of 1-isopropylsulfonyl-2-amino-6-(1-trimethylsilylethoxymethyl-2-((2-piperidin-1-yl)methyl)-5-(phenyl)-imidazole-4-yl)-benzimidazole (0.37 mmol) in acetonitrile (0.1 M) add hydrofluoric acid (HF) (48%, 53.7 mmol) and stir at 50° C. for 3 hours. Then, cool the mixture to room temperature and add a saturated aqueous solution of NaHCO$_3$ until pH=8. Extract the mixture with EtOAc (3×20 mL) and dry (MgSO$_4$) the combined organic layers and concentrate in vacuo. Purify the residue by SCX column and then by HPLC to obtain a yellow solid, 46 mg, 28% yield. MS(ES+): m/z=479.2 (M+H)+.

Prepare the methanesulfonate salt of the title compound as previously described (89% yield). MS(ES+): m/z=479.2 (M+H)+

The compounds of Examples 96-98 may be prepared essentially as described in Example 95.

| Example | Compound | MS (ES+): m/z |
|---|---|---|
| 96 | 1-isopropylsulfonyl-2-amino-6-(2-(N,N',N'-[trimethyl]- 2-(aminoethylamino)methyl)-5-(phenyl)-imidazol-4-yl)-benzimidazole | 496.3 (M + H)+ |
| 97 | 1-isopropylsulfonyl-2-amino-6-(2-((morpholin-4-yl)methyl)-5-(phenyl)-imidazol-4-yl)-benzimidazole | 481.0 (M + H)+ |
| 98 | 1-isopropylsulfonyl-2-amino-6-(2-(dimethylaminomethyl)-5-(phenyl)-imidazol-4-yl)-benzimidazole | 439.0 (M + H)+ |

EXAMPLE 99

1-isopropylsulfonyl-2-amino-6-(2-(N-[2-(piperidin-1-yl)eth-1-yl]-aminomethyl)-5-(phenyl)-imidazol-4-yl)-benzimidazole A. Reductive Amination.

To a solution of 1-isopropylsulfonyl-2-amino-6-(1-(trimethylsilylethoxymethyl)-2-(formyl)-5-(phenyl)-imidazol-4-yl)-benzimidazole (200 mg, 0.37 mmol) in methanol (8 mL) add 4 Å molecular sieves and 2-(N-piperidinyl)-ethylamine (0.37 mmol, 1 equiv), and stir overnight. Then, add sodium borohydride (70 mg, 1.85 mmol, 5 equiv) in two portions and stir at room temperature for 1 hour. Dilute the mixture with methanol (20 mL) and filter through a pad of Celite® and SiO$_2$. Concentrate the filtrates in vacuo and purify the residue by SCX column to obtain a yellow solid in 97% yield. MS(ES+): m/z=652.3 (M+H)+

B. Deprotection

Carry out following the procedure for Example 95. MS(ES+): m/z=522 (M+H)+.

The compound in Example 100 may be prepared essentially as described in Example 99.

| Example | Compound | MS (ES+): m/z |
|---|---|---|
| 100 | 1-isopropylsulfonyl-2-amino-6-(2-(N',N'-dimethyl-2-(aminoethylamino)methyl)-5-(phenyl)-imidazol-4-yl)-benzimidazole | 482.0 (M + H)+ |

EXAMPLES 101 AND 102

1-isopropylsulfonyl-2-amino-6-(2-(1-(ethoxycarbonyl)ethen-2-yl)-5-(phenyl)-imidazol-4-yl)-benzimidazole and 1-isopropylsulfonyl-6-(2-(2-carboxyethyl)-5-(phenyl)-imidazol-4-yl)-benzimidazole

A. Horner-Emmonds Condensation.

To a solution of triethylphosphonoacetate (0.081 mL, 0.407 mmol) in dry THF (0.8 mL) add dropwise a solution of potassium bis(trimethylsilyl)amide (KHMDS) (0.5 M in toluene, 0.85 mL) at −78° C. under nitrogen. Stir the mixture for 30 minutes and remove the bath. After 5 minutes, cool the mixture to −78° C. during the addition of a solution of 1-isopropylsulfonyl-2-amino-6-(1-(trimethylsilylethoxymethyl)-2-(formyl)-5-(phenyl)-imidazol-4-yl)-benzimidazole (100 mg, 0.185 mmol) in dry THF (1 mL) and slowly warm at 0° C. for 2 hours. Then, add a saturated aqueous solution of $NH_4Cl$ (10 mL) and extract the mixture with EtOAc (3×15 mL). Dry ($MgSO_4$) the combined organic layers and concentrate in vacuo. Purify the residue by flash chromatography ($SiO_2$; eluent: hexane/EtOAc 1:2) to obtain a yellow solid, 97 mg, 86% yield. MS(ES$^+$): m/z=610 (M+H)$^+$

B. Reduction

To a solution of 1-isopropylsulfonyl-2-amino-6-(1-(trimethylsilylethoxymethyl)-2-(2-(ethoxycarbonyl)ethen-2-yl)-5-(phenyl)-imidazol-4-yl)-benzimidazole (97 mg, 0.159 mmol) in MeOH (5 mL) add Pd/C (20% w, 19.4 mg). Bubble hydrogen at room temperature for 5 minutes. Stir at room temperature for 20 hours under hydrogen and filter through a pad of Celite®. Concentrate the filtrates in vacuo to give a yellow solid, 91 mg, 93% yield. MS(ES$^+$): m/z=612 (M+H)$^+$

C. Deprotection

To a solution of 1-isopropylsulfonyl-2-amino-6-(1-(trimethylsilylethoxymethyl)-2-(1-(ethoxycarbonyl)ethyl)-5-(phenyl)-imidazol-4-yl)-benzimidazole (91 mg, 0.14 mmol) in ethanol (3 mL) add HCl (37%, 3 mL) and stir at room temperature for 24 hours. Then, dilute the mixture with water (10 mL) and add a solution of NaOH (15%) until pH=6-7. Extract the mixture with EtOAc (3×30 mL) and dry ($MgSO_4$) the combined organic layers and concentrate int vacuo. Purify the residue by HPLC to give 1-isopropylsulfonyl-2-amino-6-(1-(trimethylsilylethoxymethyl)-2-(ethoxycarbonylethyl)-5-(phenyl)-imidazol-4-yl)-benzimidazole as a white solid, 11 mg, 16% yield. FIA MS(ES$^+$): m/z=482 (M+H)$^+$. 1-Isopropylsulfonyl-6-(2-(2-carboxyethyl)-5-(phenyl)-imidazol-4-yl)-benzimidazole as a white solid is also obtained, 3 mg, 5% yield. MS (ES$^+$): m/z=454 (M+H)$^+$ The compounds in Example 103-108 may be prepared essentially as described in Example 102.

| Example | Compound | MS(ES$^+$): m/z |
|---|---|---|
| 103 | 1-isopropylsulfonyl-2-amino-6-(2-(phenyl)-imidazo[466.2]pyridin-3-yl) benzimidazole dimethanesulfonate | 440.2 (M + H)$^+$ |
| 104 | 1-isopropylsulfonyl-2-amino-6-(8-(methyl)-2-(phenyl)-imidazo[1,2-a]pyridin-3-yl)-benzimidazole dimethansulfonate | 446.2 (M + H)$^+$ |
| 105 | 1-isopropylsulfonyl-2-amino-6-(2-(phenyl)-6,7-dihydro-5H-pyrrolo[1,2-a]imidazol-3-yl)-benzimidazole dimethanesulfonate | 422.2 (M + H)$^+$ |
| 106 | 1-isopropylsulfonyl-2-amino-6-(2-(4-fluorophenyl)-6,7-dihydro-5H-pyrrolo[1,2-a]imidazol-3-yl)-benzimidazole methanesulfonate | 440.2 (M + H)$^+$ |
| 107 | 1-isopropylsulfonyl-2-amino-6-(2-(phenyl)-5,6,7,8-tetrahydro-imidazo[1,2-a]pyridin-3-yl)-benzimidazole | 436 (M + H)$^+$ |
| 108 | 1-isopropylsulfonyl-2-amino-6-(2-(phenyl)-5,6-dihydro-4H-pyrrolo[1,2-b]pyrazol-3-yl)-benzimidazole methanesulfonate | 422.2 (M + H)$^+$ |

EXAMPLE 109

1-isopropylsulfonyl-2-amino-6-(1-(4-methoxybenzyl)-2-(hydroxymethyl)-4-(phenyl)-imidazol-5-yl)-benzimidazole To a solution of 1-(4-methoxybenzyl)-2-tert-butyldimethylsilyloxymethyl-4-(phenyl)-5-iodoimidazole (50 mg, 0.0935 mmol) in dry toluene (0.8 mL) previously bubbled with a stream of nitrogen, add $PdCl_2(PPh_3)_2$ (4.5 mg, 0.00641 mmol) in one portion. After 5 minutes, add a suspension of 1-isopropylsulfonyl-2-amino-benzimidazole-6-boronic acid (40 mg, 0.141 mmol) in ethanol (0.8 mL) previously bubbled with a stream of nitrogen, followed by sodium carbonate (2M in water, 0.32 mL, 0.640 mmol). Stir the mixture for 2.5 hours at 100° C., cool to room temperature, dilute with 10% HCl (5 mL), extract with EtOAc (15 mL), dry ($Na_2SO_4$), and concentrate in vacuo. Purify the residue by flash chromatography ($SiO_2$, $CH_2Cl_2$/MeOH 19:1→5:1), dissolve the material obtained in MeCN (0.5 mL), and treat with HF (48% in $H_2O$, 0.12 mL, 3.31 mmol) at room temperature for 4 hours. Dilute the mixture with EtOAc (15 nm), wash with saturated $NaHCO_3$ (5 mL), dry ($Na_2SO_4$), and concentrate in vacuo. Purify the residue by flash chromatography (SiO$_2$, CH$_2$Cl$_2$/MeCN/MeOH 85:15:5) to provide 18 mg (36% yield). MS (MS$^+$): m/z=532 (M+H)$^+$

EXAMPLE 110

1-isopropylsulfonyl-2-amino-6-(1-(1-(tert-butoxycarbonyl)piperidin-4-yl)-4-(phenyl)-imidazol-5-yl)-benzimidazole Add tert-butylamine (0.125 g, 1.7 mmol) to a solution of N-[1-(ethoxycarbonyl)-piperidin-4-yl] (1-isopropylsulfonyl-2-amino-6-formylbenzimidazole)-imine (0.36 g, 0.86 mmol) and α-(p-toluenesulfonyl)benzylisocyanide (0.463 g, 1.7 mmol) in methanol (10 mL). Heat the reaction mixture to reflux and stir over night. Cool to room temperature, concentrate under reduced pressure, and partition the residue between dichloromethane (50 mL) and water (50 mL). Separate the layers, wash the organic layer with saturated aqueous sodium chloride (2×15 mL), dry over sodium sulfate, and concentrate under reduced pressure. Subject the residue to silica gel chromatography, eluting with 9:1 ethyl acetate:hexanes to provide 0.130 g (28%) of the title compound. MS(ES$^+$): m/z=537.2 (M+H)$^+$ The compounds of Examples 111-171 may be prepared essentially as described in Example 110.

| EXAMPLE | Compound | MS(ESI$^+$): m/z |
|---|---|---|
| 111 | 1-isopropylsulfonyl-2-amino-6-(1-(1-(tert-butoxycarbonyl)piperidin-4-yl)-4-(4-fluorophenyl)-imidazol-5-yl)-benzimidazole | 555.1 (M + H)$^+$ |
| 112 | 1-isopropylsulfonyl-2-amino-6-(1-(1-(benzyl)piperidin-4-yl)-4-(phenyl)-imidazol-5-yl)-benzimidazole | 554.9 (M + H)$^+$ |
| 113 | 1-isopropylsulfonyl-2-amino-6-(1-(1-(benzyl)piperidin-4-yl)-4-(4-fluorophenyl)-imidazol-5-yl)-benzimidazole | 572.8 (M + H)$^+$ |
| 114 | 1-isopropylsulfonyl-2-amino-6-(1-(methyl)-4-(phenyl)-imidazol-5-yl)-benzimidazole | 396.0 (M + H)$^+$ |
| 115 | 1-isopropylsulfonyl-2-amino-6-(1-(2-(hydroxy)eth-1-yl)-4-(phenyl)-imidazol-5-yl)-benzimidazole | 425.9 (M + H)$^+$ |
| 116 | 1-isopropylsulfonyl-2-amino-6-(1-(2-(methoxy)eth-1-yl)-4-(phenyl)-imidazol-5-yl)-benzimidazole | 440.6 (M + H)$^+$ |
| 117 | 1-isopropylsulfonyl-2-amino-6-(1-(2-(N-(tert-butoxycarbonyl)amino)eth-1-yl)-4-(phenyl)-imidazol-5-yl)-benzimidazole | 524.9 (M + H)$^+$ |
| 118 | 1-isopropylsulfonyl-2-amino-6-(1-(cyclopropylmethyl)-4-(phenyl)-imidazol-5-yl)-benzimidazole | 436.1 (M + H)$^+$ |
| 119 | 1-isopropylsulfonyl-2-amino-6-(1-(cyclopropylmethyl)-4-(4-fluorophenyl)-imidazol-5-yl)-benzimidazole | 455.1 (M + H)$^+$ |
| 120 | 1-isopropylsulfonyl-2-amino-6-(1-(4-fluorobenzyl)-4-(phenyl)-imidazol-5-yl)-benzimidazole | 489.9 (M + H)$^+$ |
| 121 | 1-isopropylsulfonyl-2-amino-6-(1-(2,4-difluorobenzyl)-4-(phenyl)-imidazol-5-yl)-benzimidazole | 507.9 (M + H)$^+$ |
| 122 | 1-isopropylsulfonyl-2-amino-6-(1-((pyridin-2-yl)methyl)-4-(phenyl)-imidazol-5-yl)-benzimidazole | 472.9 (M + H)$^+$ |
| 123 | 1-isopropylsulfonyl-2-amino-6-(1-((pyridin-3-yl)methyl)-4-(phenyl)-imidazol-5-yl)-benzimidazole | 472.9 (M + H)$^+$ |
| 124 | 1-isopropylsulfonyl-2-amino-6-(1-((pyridin-4-yl)methyl)-4-(phenyl)-imidazol-5-yl)-benzimidazole | 473.0 (M + H)$^+$ |
| 125 | 1-isopropylsulfonyl-2-amino-6-(1-(3-(phenyl)prop-1-yl)-4-(phenyl)-imidazol-5-yl)-benzimidazole | 499.2 (M + H)$^+$ |
| 126 | 1-isopropylsulfonyl-2-amino-6-((1-(2-(morpholin-4-yl)eth-1-yl)-4-(phenyl)-imidazol-5-yl)-benzimidazole | 494.8 (M + H)$^+$ |
| 127 | 1-isopropylsulfonyl-2-amino-6-(1-(2-(morpholin-4-yl)eth-1-yl)-4-(4-fluorophenyl)-imidazol-5-yl)-benzimidazole | 513.0 (M + H)$^+$ |
| 128 | 1-isopropylsulfonyl-2-amino-6-(1-(3-(morpholin-4-yl)prop-1-yl)-4-(phenyl)-imidazol-5-yl)benzimidazole | 509.1 (M + H)$^+$ |
| 129 | 1-isopropylsulfonyl-2-amino-6-(1-(cyclohexyl)-4-(phenyl)-imidazol-5-yl)-benzimidazole | 464.0 (M + H)$^+$ |
| 130 | 1-isopropylsulfonyl-2-amino-6-(1-(trans-4-hydroxycyclohex-1-yl)-4-(phenyl)-imidazol-5-yl)-benzimidazole | 479.9 (M + H)$^+$ |
| 131 | 1-isopropylsulfonyl-2-amino-6-(1-(trans-4-hydroxycyclohex-1-yl)-4-(4-fluorophenyl)-imidazol-5-yl)-benzimidazole | 498.0 (M + H)$^+$ |
| 132 | 1-isopropylsulfonyl-2-amino-6-(1-(trans-4-hydroxycyclohex-1-yl)-4-(thien-3-yl)-imidazol-5-yl)-benzimidazole | 486.0 (M + H)$^+$ |
| 133 | 1-isopropylsulfonyl-2-amino-6-(1-(4-(N-(tert-butoxycarbonyl)amino)cyclohex-1-yl)-4-(phenyl)-imidazol-5-yl)-benzimidazole | 578.9 (M + H)$^+$ |
| 134 | 1-isopropylsulfonyl-2-amino-6-(1-(1,4-dioxaspiro[4.5]dec-8-yl)-4-(phenyl)-imidazol-5-yl)-benzimidazole | 522.2 (M + H)$^+$ |
| 135 | 1-isopropylsulfonyl-2-amino-6-(1-(tetrahydropyran-4-yl)-4-(phenyl)-imidazol-5-yl)-benzimidazole | 465.9 (M + H)$^+$ |

-continued

| EXAMPLE | Compound | MS(ESI+): m/z |
|---|---|---|
| 136 | 1-isopropylsulfonyl-2-amino-6-(1-(2,2,6,6-tetramethylpiperidin-4-yl)-4-(phenyl)-imidazol-5-yl)-benzimidazole | 521.0 (M + H)+ |
| 137 | 1-isopropylsulfonyl-2-amino-6-(1-(R-3-hydroxyprop-2-yl)-4-(phenyl)-imidazol-5-yl)-benzimidazole | 440.0 (M + H)+ |
| 138 | 1-isopropylsulfonyl-2-amino-6-(1-(S-3-hydroxyprop-2-yl)-4-(phenyl)-imidazol-5-yl)-benzimidazole | 440.0 (M + H)+ |
| 139 | 1-isopropylsulfonyl-2-amino-6-(1-(S-3-hydroxyprop-2-yl)-4-(4-fluorophenyl)-imidazol-5-yl)-benzimidazole | 458.4 (M + H)+ |
| 140 | 1-isopropylsulfonyl-2-amino-6-(1-(isopropyl)-4-(phenyl)-imidazol-5-yl)-benzimidazole | 424.4 (M + H)+ |
| 141 | 1-isopropylsulfonyl-2-amino-6-(1-(isopropyl)-4-(4-fluorophenyl)-imidazol-5-yl)-benzimidazole | 442.4 (M + H)+ |
| 142 | 1-isopropylsulfonyl-2-amino-6-(1-(2-(methoxycarbonyl)eth-1-yl)-4-(phenyl)-imidazol-5-yl)-benzimidazole | 468.0 (M + H)+ |
| 143 | 1-isopropylsulfonyl-2-amino-6-(1-(R-1-phenyl)-2-(hydroxyeth-1-yl)-4-(phenyl)-imidazol-5-yl)-benzimidazole | 502.0 (M + H)+ |
| 144 | 1-isopropylsulfonyl-2-amino-6-(1-(trans-2-hydroxycyclohex-1-yl)-4-(phenyl)-imidazol-5-yl)-benzimidazole | 480.0 (M + H)+ |
| 145 | 1-isopropylsulfonyl-2-amino-6-(1-(trans-2-hydroxymethylcyclohex-1-yl)-4-(phenyl)-imidazol-5-yl)-benzimidazole | 494.1 (M + H)+ |
| 146 | 1-isopropylsulfonyl-2-amino-6-(1-(3-fluorobenzyl)-4-(phenyl)-imidazol-5-yl)-benzimidazole | 490.1 (M + H)+ |
| 147 | 1-isopropylsulfonyl-2-amino-6-(1-(2-fluorobenzyl)-4-(phenyl)-imidazol-5-yl)-benzimidazole | 490.1 (M + H)+ |
| 148 | 1-isopropylsulfonyl-2-amino-6-(1-(4-methoxybenzyl)-4-(phenyl)-imidazol-5-yl)-benzimidazole | 502.5 (M + H)+ |
| 149 | 1-isopropylsulfonyl-2-amino-6-(1-(S-1-cyclohexyl-3-hydroxyprop-2-yl)-4-(phenyl)-imidazol-5-yl)-benzimidazole | 522.1 (M + H)+ |
| 150 | 1-isopropylsulfonyl-2-amino-(1-(trans-4-hydroxycyclohex-1-yl)-4-(3-fluorophenyl)-imidazol-5-yl)-benzimidazole | 498.3 (M + H)+ |
| 151 | 1-isopropylsulfonyl-2-amino-(1-(trans-4-hydroxycyclohex-1-yl)-4-(2-fluorophenyl)-imidazol-5-yl)-benzimidazole | 498.3 (M + H)+ |
| 152 | 1-isopropylsulfonyl-2-amino-6-(1-(methyl)-4-(4-fluorophenyl)-imidazol-5-yl)-benzimidazole | 414.2 (M + H)+ |
| 153 | 1-isopropylsulfonyl-2-amino-6-(1-(ethyl)-4-(phenyl)-imidazol-5-yl)-benzimidazole | 410.3 (M + H)+ |
| 154 | 1-isopropylsulfonyl-2-amino-6-(1-(cyclopropyl)-4-(phenyl)-imidazol-5-yl)-benzimidazole | 422.2 (M + H)+ |
| 155 | 1-isopropylsulfonyl-2-amino-6-(1-(cyclopentyl)-4-(phenyl)-imidazol-5-yl)-benzimidazole | 450.3 (M + H)+ |
| 156 | 1-isopropylsulfonyl-2-amino-6-(1-(ethyl)-4-(4-fluorophenyl)-imidazol-5-yl)-benzimidazole | 428.2 (M + H)+ |
| 157 | 1-isopropylsulfonyl-2-amino-6-(1-(cyclopropyl)-4-(4-fluorophenyl)-imidazol-5-yl)-benzimidazole | 440.3 (M + H)+ |
| 158 | 1-isopropylsulfonyl-2-amino-6-(1-(cyclopentyl)-4-(4-fluorophenyl)-imidazol-5-yl)-benzimidazole | 468.3 (M + H)+ |
| 159 | 1-isopropylsulfonyl-2-amino-6-(1-(cyclohexyl)-4-(4-fluorophenyl)-imidazol-5-yl)-benzimidazole | 482.3 (M + H)+ |
| 160 | 1-isopropylsulfonyl-2-amino-6-(1-((pyridin-3-yl)methyl)-4-(3-fluorophenyl)-imidazol-5-yl)-benzimidazole | 491.2 (M + H)+ |
| 161 | 1-isopropylsulfonyl-2-amino-6-(1-((pyridin-3-yl)methyl)-4-(2-fluorophenyl)-imidazol-5-yl)-benzimidazole | 491.2 (M + H)+ |
| 162 | 1-isopropylsulfonyl-2-amino-6-(1-(cyclopropyl)-4-(2-fluorophenyl)-imidazol-5-yl)-benzimidazole | 440.1 (M + H)+ |
| 163 | 1-isopropylsulfonyl-2-amino-6-(1-(cyclopropyl)-4-(3-fluorophenyl)-imidazol-5-yl)-benzimidazole | 440.1 (M + H)+ |
| 164 | 1-isopropylsulfonyl-2-amino-6-(1-(methyl)-4-(2,4-difluorophenyl)-imidazol-5-yl)-benzimidazole | 432.2 (M + H)+ |
| 165 | 1-isopropylsulfonyl-2-amino-6-(1-(trans-4-hydroxycyclohex-1-yl)-4-(2,4-difluorophenyl)-imidazol-5-yl)-benzimidazole | 516.2 (M + H)+ |
| 166 | 1-isopropylsulfonyl-2-amino-6-(1-(cyclohexyl)-4-(2,4-difluorophenyl)-imidazol-5-yl)-benzimidazole | 500.2 (M + H)+ |
| 167 | 1-isopropylsulfonyl-2-amino-6-(1-(cyclopropyl)-4-(2,4-difluorophenyl)-imidazol-5-yl)-benzimidazole | 458.2 (M + H)+ |
| 168 | 1-isopropylsulfonyl-2-amino-6-(1-(methyl)-4-(2,3-difluorophenyl)-imidazol-5-yl)-benzimidazole | 432.1 (M + H)+ |

-continued

| EXAMPLE | Compound | MS(ESI+): m/z |
|---|---|---|
| 169 | 1-isopropylsulfonyl-2-amino-6-(1-(trans-4-hydroxycyclohex-1-yl)-4-(2,3-difluorophenyl)-imidazol-5-yl)-benzimidazole | 516.1 (M + H)+ |
| 170 | 1-isopropylsulfonyl-2-amino-6-(1-(1-(ethoxycarbonyl)piperidin-4-yl)-4-(2-fluorophenyl)-imidazol-5-yl)-benzimidazole | 555.1 (M + H)+ |
| 171 | 1-isopropylsulfonyl-2-amino-6-(1-(1-(ethoxycarbonyl)piperidin-4-yl)-4-(3-fluorophenyl)-imidazol-5-yl)-benzimidazole | 555.1 (M + H)+ |

EXAMPLE 172

1-isopropylsulfonyl-2-amino-6-(1-(cyclopropyl)-4-(2-fluorophenyl))-imidazol-5-yl) benzimidazole methanesulfonate Add methanesulfonic acid (0.029 ml, 0.455 mmol)) to a solution of 1-isopropylsulfonyl-2-amino-6-(1-(cyclopropyl)-4-(2-fluorophenyl)-imidazol-5-yl) benzimidazole (0.200 g, 0.455 mmol) prepared following the procedure for Example 110 in 10% methanol/dichloromethane (3 mL). Remove solvents under reduced pressure to 1-isopropylsulfonyl-2-amino-6-(1-(cyclopropyl)$_4$-(2-fluorophenyl)-imidazol-5-yl) benzimidazole methanesulfonate (0.25 g). MS(ES+): m/z=440.1 (M+H)+

EXAMPLE 173

1-isopropylsulfonyl-2-amino-6-(5-(3-fluorophenyl)-imidazol-4-yl)-benzimidazole

Treat 1-isopropylsulfonyl-2-amino-6-formylbenzimidazole(0.3 g, 1.1 mmol) in THF (5 mL) with ammonium hydroxide (0.39 mL, 3.4 mol) and stir for 3 hours at room temperature. Treat the reaction with 3-fluorophenyl-tolylsulfonomethylisocyanide (0.23 g, 0.8 mmol) and piperazine (0.096 g, 1.1 mmol). Stir the reaction for 5 hours and then dilute in EtOAc. Wash the organic phase with water and saturated aqueous sodium chloride, dry over sodium sulfate, filter, and remove the solvent in vacuo. Slurry the residue in cold EtOAc and filter to afford 0.195 g (44%) of the desired product. MS(ES+) m/z=400.2 (M+H)+

The compounds of Examples 174-176 may be prepared essentially as described in Example 173.

| Example | Compound | MS(ESI+): m/z |
|---|---|---|
| 174 | 1-isopropylsulfonyl-2-amino-6-(5-(2-fluorophenyl)-imidazol-4-yl)-benzimidazole | 400.2 (M + H)+ |
| 175 | 1-isopropylsulfonyl-2-amino-6-(5-(2,4-fluorophenyl)-imidazol-4-yl)-benzimidazole | 418.1 (M + H)+ |
| 176 | 1-isopropylsulfonyl-2-amino-6-(5-(2,3-fluorophenyl)-imidazol-4-yl)-benzimidazole | 418.1 (M + H)+ |

EXAMPLE 177

1-isopropylsulfonyl-2-amino-6-(1-p-nitrophenyl-4-(phenyl)-imidazol-5-yl)-benzimidazole Add to a reaction tube p-nitroaniline (0.138 g, 1 mmol), 1-isopropylsulfonyl-2-amino-6-formylbenzimidazole (Preparation 1, 0.267 g, 1 mmol), acetic acid (10 µL) and toluene (2 mL). Seal the reaction vessel and heat the suspension to 120° C. for 24 hours. Wash the crude imine with CHCl$_3$ and dry in vacuo to afford 300 mg of yellow powder. MS(ES)+: m/z=388.1 (M+H)+

Suspend NaH (65 mg, 60% mineral oil) was in dimethoxyethane (DME) (2 mL) at room temperature. Add α-(p-toluenesulfonyl)benzylisocyanide (Preparation 2, 0.135 g, 0.5 mmol) to the suspension, stir for 5 minutes, and add the imine (0.116 g, 0.3 mmol). After 2 hours, introduce water and EtOAc into the reaction, and rapidly stir the contents for 1-2 minutes, transfer to a separatory funnel, wash the organic phase with water, and then wash with saturated aqueous sodium chloride. Dry the organic layer over Na$_2$SO$_4$, filter, and concentrate to afford the desired product. Purify by chromatographic separation over a small silica column using 3:2 MeCl$_2$/MeCN+10% MeOH to afford 138 mg of the desired product. MS(ES+): m/z=503.3 (M+H)+

EXAMPLE 178

1-isopropylsulfonyl-2-amino-6-(1-(4-amino)-4-(phenyl)-imidazol-5-yl)-benzimidazole To 0.025 g (0.05 mmol) of 1-isopropylsulfonyl-2-amino-6-(1-p-nitrophenyl-4-(phenyl)-imidazol-5-yl)-benzimidazole in EtOH (1 mL) at room temperature add SnCl$_2$ dihydrate (50 mg, 0.22 mmol). After 3 hours, treat the crude reaction with H$_2$O (1 mL), stir another 25 minutes, and then add Na$_2$CO$_3$ to take the pH to approximately 10. Transfer the reaction mixture to a separatory funnel and dilute with EtOAc and water. Reextract the aqueous layer 3 times with EtOAc, wash the combined organics with saturated aqueous sodium chloride, dry over Na$_2$SO$_4$, filter and concentrate in vacuo to afford the crude product. Purify by chromatography using preparative TLC (Silica, 20×20 cm×1 mm, 20:1 MeCl$_2$/MeOH to afford 6 mg of desired product. MS(ES+): m/z=473.2 (M+H)+

EXAMPLE 179

1-isopropylsulfonyl-2-amino-6-(2-(methyl)-4-(phenyl)-thiazol-5-yl)-benzimidazole A. 2-methyl-4-phenylthiazole Add thioacetamide (0.09 g, 1.2 mmol) to a solution of 2-bromoacetophenone (0.2 g, 1.0 mmol) in 30 mL dioxane. Stir at room temperature for 4 hours, dilute with ethyl acetate, wash sequentially with aqueous sodium carbonate (3×15 mL) and water (3×20 mL). Dry the organic phase over sodium sulfate, concentrate under reduced pressure, and subject the residue to silica gel chromatography, eluting with hexane containing 10% ethyl acetate to provide the desired compound in 78% yield. MS(ES$^+$): m/z=176.1 (M+H)$^+$ B. 2-methyl-4-phenyl-5-(tributylstannyl)thiazole Add n-butyllithium (0.46 mL, 0.74 mmol, 1.6 M in tetrahydrofuran) to a solution of 2-methyl-4-phenylthiazole (0.13 g, 0.74 mmol) in tetrahydrofuran (7 mL) cooled to −78° C. under a nitrogen atmosphere. Stir at −78° C. for 45 minutes, add tributyltin chloride (0.2 mL, 0.74 mmol), and stir for 2 hours as the reaction mixture warms to room temperature. Add aqueous ammonium chloride and then partition the mixture between ethyl acetate and water. Extract the aqueous phase with ethyl acetate. Wash the combined organic layers sequentially with water and saturated aqueous sodium chloride, dry over sodium sulfate, and concentrate under reduced pressure. Subject the residue to silica gel chromatography, eluting with hexane containing 10% ethyl acetate to provide the desired compound in 68% yield. MS(ES$^+$): m/z=466.1 (M+H)$^+$ C. Coupling Stir a mixture of 2-methyl-4-phenyl-5-(tributylstannyl) thiazole (0.1 g, 0.21 mmol), 1-isopropylsulfonyl-2-amino-6-iodobenzimidazole (0.07 g, 0.21 mmol), and (acetonitrile) palladium(II) chloride (0.021 mmol) in dry dimethylformamide (2 mL) at 100° C. for 4 hours under a nitrogen atmosphere. Cool to room temperature and dilute with ethyl acetate (20 mL). Wash sequentially with water (3×5 mL) and saturated aqueous sodium chloride (3×5 mL), dry over sodium sulfate, and concentrate under reduced pressure. Subject the residue to silica gel chromatography, eluting with 7:1 dichloromethane:acetonitrile to provide the title compound as a white solid in 2% yield. MS(ES$^+$): m/z=413.0 (M+H)$^+$

EXAMPLE 180

1-isopropylsulfonyl-2-amino-6-(2,4-diphenyl-thiazol-5-yl)-benzimidazole

Beginning with thiobenzamide and 2-bromoacetophenone, prepare the title compound essentially as described in Example 179, 12% yield. MS(ES$^+$): m/z=474.8 (M+H)$^+$

EXAMPLE 181

2-amino-6-(2-(2,6-difluorophenyl)-5-(phenyl)-imidazol-4-yl)-benzimidazole

Stir a mixture of 1-isopropylsulfonyl-2-amino-6-(2-(2,6-difluorophenyl)-5-(phenyl)-imidazol-4-yl)-benzimidazole (0.07 g, 0.142 mmol) and 1.42 mL 1 N sodium hydroxide in 1:1 water:acetonitrile at 60° C. for 1 hour. Cool the mixture to room temperature and dilute with water and ethyl acetate. Extract the aqueous phase with ethyl acetate (3 times). Wash the combined organic phases sequentially with water and saturated aqueous sodium chloride, dry over sodium sulfate, and concentrate under reduced pressure. Subject the residue to silica gel chromatography, eluting with 2:1 dichloromethane:methanol to provide the title compound in 93% yield. MS(ES$^+$): m/z=388.0 (M+H)$^+$ The compounds of Examples 182-183 may be prepared essentially as described in Example 181.

| EXAMPLE | Compound | MS(ES$^+$): m/z |
|---|---|---|
| 182 | 2-amino-6-(5-(phenyl)-imidazol-4-yl)-benzimidazole | 276.0 (M + H)$^+$ |
| 183 | 2-amino-6-(2-(thien-2-yl)-5-(phenyl))-imidazol-4-yl)-benzimidazole | 358.8 (M + H)$^+$ |

EXAMPLE 184

1-isopropylsulfonyl-2-amino-6-(2-(4-aminophenyl)-5-(phenyl)-imidazol-4-yl)-benzimidazole Purge a suspension of 1-isopropylsulfonyl-2-amino-6-(2-(4-nitrophenyl)-5-(phenyl)-imidazol-4-yl)-benzimidazole (0.149 g, 0.3 mmol) and 10% palladium on carbon (0.03 mmol) in methanol with hydrogen for 10 minutes and then stir under a hydrogen atmosphere for 6 hours. Filter through a bed of Celite® and concentrate the residue under reduced pressure. Subject the residue to silica gel chromatography, eluting with 4% methanol in dichloromethane to provide the title compound in 28% yield. MS(ES$^+$): m/z=473.0 (M+H)$^+$

EXAMPLE 185

1-isopropylsulfonyl-2-amino-6-(2-(2-aminothien-5-yl)-5-(phenyl)-imidazol-4-yl)-benzimidazole Beginning with 1-isopropylsulfonyl-2-amino-6-(2-(2-nitrothien-5-yl)-5-(phenyl)-imidazol-4-yl)-benzimidazole, prepare the title compound essentially as described in Example 184, 22% yield. MS(ES$^+$): m/z=479.0 (M+H)$^+$

EXAMPLES 186 AND 187

1-isopropylsulfonyl-2-amino-6-(1-(methyl)-2-(2,6-difluorophenyl)-5-(phenyl)-imidazol-4-yl)-benzimidazole and 1-isopropylsulfonyl-2-amino-6-(1-(methyl)-2-(2,6-difluorophenyl)-4-(phenyl)-imidazol-5-yl)-benzimidazole Add cesium carbonate (0.134 mmol) and methyl iodide (0.134 mmol) to a solution of 1-isopropylsulfonyl-2-amino-6-(2-(2,6-difluorophenyl)-5-(phenyl)-imidazol-4-yl-benzimidazole (0.12 mmol) in dry dimethylformamide (2.5 mL) at 0° C. Stir the mixture at room temperature for 16 hours, dilute with water and ethyl acetate, and separate the layers. Extract the aqueous phase with ethyl acetate (3 times). Wash the combined organic phases sequentially with cold water (5 times) and saturated aqueous sodium chloride, dry over sodium sulfate, and concentrate under reduced pressure. Subject the residue to silica gel chromatography. Dissolve the isomer mixture in dichloromethane and subject this mixture to preparative HPLC (Kromasil Si60, 7 μm, 20×250 mm ID) eluting with dichloromethane containing 4% methanol (100 mL/min) to provide 1-isopropylsulfonyl-2-amino-6-(1-(methyl)-2-(2,6-difluorophenyl)-5-(phenyl)-imidazol-4-yl)-benzimidazole (11.1 minutes) in 22% yield. MS(ES$^+$): m/z=508.2 (M+H)$^+$ and 1-isopropylsulfonyl-2-amino-6-(1-(methyl)-2-(2,6-difluorophenyl)-4-(phenyl)-imidazol-5-yl)-benzimidazole (16.1 min) in 33% yield. MS(ES$^+$): m/z=508.2 (M+H)$^+$

EXAMPLES 188 AND 189

1-isopropylsulfonyl-2-amino-6-(1-(methyl)-2-(thien-2-yl)-5-(phenyl)-imidazol-4-yl)-benzimidazole and 1-isopropylsulfonyl-2-amino-6-(1-(methyl)-2-(thien-2-yl)-4(phenyl)-imidazol-5-yl)-benzimidazole Beginning with 1-isopropylsulfonyl-2-amino-6-(2-(thien-2-yl)-5-(phenyl)-imidazol-4-yl)-benzimidazole and 1-isopropylsulfonyl-2-amino-6-(1-methyl-2-(thien-2-yl)-5-(phenyl)-imidazol-4-yl)-benzimidazole and 1-isopropylsulfonyl-2-amino-6-((1-methyl-2-(thien-2-yl)-4-phenyl)-imidazol-5-yl)-benzimidazole, prepare the title compounds essentially as described in Example 187. MS(ES$^+$): m/z=478.2 (M+H)$^+$

EXAMPLE 190

1-isopropylsulfonyl-2-amino-6-(2-(piperidin-4-yl)-5-(phenyl)-imidazol-4-yl)-benzimidazole Vigorously stir a mixture of 1-isopropylsulfonyl-2-amino-6-(2-(1-(benzyloxycarbonyl)piperidin-4-yl)-5-(phenyl)-imidazol-4-yl)-benzimidazole (0.74 g, 1.24 mmol), ammonium formate (4.94 mmol), and 10% palladium on carbon (0.12 mmol) in 30 mL absolute ethanol at reflux for 5 hours. Cool the reaction mixture to room temperature, filter through a bed of Celite®, and concentrate the filtrate under reduced pressure. Subject the residue to silica gel chromatography, eluting with 19:1 dichloromethane:methanol to provide the title compound. MS(ES$^+$): m/z=465.2 (M+H)$^+$

EXAMPLE 191

1-isopropylsulfonyl-2-amino-6-(2-(piperidin-4-yl)-5-(4-fluorophenyl)-imidazol-4-yl)-benzimidazole di-trifluoroacetate Add hydrogen chloride in ethyl acetate to a solution of 1-isopropylsulfonyl-2-amino-6-((2-(1-(tert-butoxycarbonyl)-piperidin-4-yl)-5-(4-fluorophenyl))-imidazol-4-yl)-benzimidazol (0.05 mmol) in ethyl acetate (2 mL) and stir the mixture at room temperature over night. Filter the resulting suspension and wash with diethyl ether to provide the title compound in 25% yield. Dissolve the solid in 1:1 dimethylsulfoxide:acetonitrile and subject to HPLC (YMC C18, 5 μm, 20×50 mm ID) eluting with a gradient of water+0.05% trifluoroacetic acid:acetonitrile+0.05% trifluoroacetic acid from 90:10 to 45:55 in 15 minutes (9 mL/min) to provide the title compound 25%, 9.33 min). MS(ES$^+$): m(z=483.2 (M+H)$^+$

EXAMPLE 192

1-isopropylsulfonyl-2-amino-6-(1-(piperidin-4-yl)-4-(phenyl)-imidazol-5-yl)-benzimidazole Heat a mixture of 1-isopropylsulfonyl-2-amino-6-(1-(1-(ethoxycarbonyl)piperidin-4-yl)-4(phenyl)-imidazol-5-yl) benzimidazole (55 mg) in concentrated hydrochloric acid at reflux for 24 hours. Cool the mixture to room temperature, add 5 N sodium hydroxide until the mixture is basic, and extract with dichloromethane. Concentrate the organic phase under reduced pressure and subject the residue to silica gel chromatography, eluting with dichloromethane followed by 1:1 dichloromethane:methanol to provide 20 mg (43%) of the title compound. MS(ES$^+$): m/z=465.0 (M+H)$^+$

EXAMPLE 193

1-isopropylsulfonyl-2-amino-6-(1-(piperidin-4-yl)-4-(4-fluorophenyl)-imidazol-5-yl)-benzimidazole Beginning with 1-isopropylsulfonyl-2-amino-6-(1-(1-(ethoxycarbonyl)piperidin-4-yl)-4-(4-fluorophenyl)-imidazol-5-yl)-benzimidazole, prepare the title compound essentially as described in Example 192. MS(ES$^+$): m/z=483.0 (M+H)$^+$

EXAMPLE 194

1-isopropylsulfonyl-2-amino-6-(2-(1-(ethyl)piperidin-4-yl)-5-(phenyl)-imidazol-4-yl)-benzimidazole Stir a mixture of 1-isopropylsulfonyl-2-amino-6-(2-(piperidin-4-yl)-5-(phenyl)-imidazol-4-yl)-benzimidazole (0.574 g, 1.23 mmol), triethylamine (3.1 mmol), and iodoethane (1.54 mmol) in anhydrous dimethylformamide (5 mL) at room temperature for 6 hours. Partition the mixture between ethyl acetate and water. Extract the aqueous layer with ethyl acetate (3 times). Wash the combined organic layers sequentially with cold water (5 times) and saturated aqueous sodium chloride, dry over sodium sulfate, and concentrate under reduced pressure. Subject the residue to silica gel chromatography to provide the title compound in 76% yield. MS(ES$^+$): m/z=493.2 (M+H)$^+$ The compounds of Examples 195-203 may be prepared essentially as described in Example 194.

| Example | Compound | MS(ES$^+$): m/z |
|---|---|---|
| 195 | 1-isopropylsulfonyl-2-amino-6-(2-(1-(methylpiperidin-4-yl))-5-(phenyl)-imidazol-4-yl)-benzimidazole | 479.1 (M + H)$^+$ |

-continued

| Example | Compound | MS(ES+): m/z |
|---|---|---|
| 196 | 1-isopropylsulfonyl-2-amino-6-(2-(1-(3,3,3-trifluoroprop-1-yl)piperidin-4-yl)-5-(phenyl)-imidazol-4-yl)-benzimidazole | 561.3 (M + H)+ |
| 197 | 1-isopropylsulfonyl-2-amino-6-(2-(1-(2-hydroxyeth-1-yl)piperidin-4-yl)-5-(phenyl)-imidazol-4-yl)-benzimidazole | 509.2 (M + H)+ |
| 198 | 1-isopropylsulfonyl-2-amino-6-(2-(1-(benzyl)piperidin-4-yl)-5-(phenyl)-imidazol-4-yl)-benzimidazole | 555.2 (M + H)+ |
| 199 | 1-isopropylsulfonyl-2-amino-6-(2-(1-(2-dimethylamino-ethyl)piperidin-4-yl)-5-(phenyl)-imidazol-4-yl)-benzimidazole | 536.2 (M + H)+ |
| 200 | 1-isopropylsulfonyl-2-amino-6-(2-(1-(isobutyl)piperidin-4-yl)-5-(phenyl)-imidazol-4-yl)-benzimidazole | 521. (M + H)+ |
| 201 | 1-isopropylsulfonyl-2-amino-6-(2-(1-(isobutyl)piperidin-4-yl)-5-(4-fluorophenyl)-imidazol-4-yl)-benzimidazole | 539.3 (M + H)+ |
| 202 | 1-isopropylsulfonyl-2-amino-6-(2-(1-(pyridin-2-yl-methyl)piperidin-4-yl)-5-(phenyl)-imidazol-4-yl)-benzimidazole | 556.3 (M + H)+ |
| 203 | 1-isopropylsulfonyl-2-amino-6-(2-(1-(1-methyl-1H-imidazol-2-yl-methyl)piperidin-4-yl-5-(phenyl)-imidazol-4-yl)-benzimidazole | 559.3 (M + H)+ |

EXAMPLE 204

1-isopropylsulfonyl-2-amino-6-(1-(1-(methyl)piperidin-4-yl)-4-(phenyl)-imidazol-5-yl)-benzimidazole Add aqueous formaldehyde (37% w/w, 0.15 mmol) to a solution of 1-isopropylsulfonyl-2-amino-6-(1-(piperidin-4-yl)-4-(phenyl)-imidazol-5-yl)-benzimidazole (75 mg) in methanol (10 mL). Stir the mixture at room temperature for 30 minutes, then cool to 0° C. Add acetic acid (0.3 mL) followed by sodium cyanoborohydride (18 mg) and stir over night at room temperature. Concentrate the mixture under reduced pressure and then dissolve the residue in ethyl acetate. Wash the solution twice with 1 N sodium hydroxide and concentrate the organic phase under reduced pressure to provide 60 mg (79%) of the title compound. MS(ES+): m/z=479.6 (M+H)+

The compounds of Examples 205-206 may be prepared essentially as described in Example 204.

| Example | Compound | MS(ES+): m/z |
|---|---|---|
| 205 | 1-isopropylsulfonyl-2-amino-6-(1-(1-methylpiperidin-4-yl)-4-(4-fluorophenyl)-imidazol-5-yl)-benzimidazole | 497.6 (M + H)+ |
| 206 | 1-isopropylsulfonyl-2-amino-6-(1-(1-(isopropyl)piperidin-4-yl)-4-(phenyl)-imidazol-5-yl)-benzimidazole | 507.6 (M + H)+ |

EXAMPLE 207

1-isopropylsulfonyl-2-amino-6-((1-(cyclohexan-1-on-4-yl)-4-(phenyl)-imidazol-5-yl)-benzimidazole Stir a solution of 1-isopropylsulfonyl-2-amino-6-(1-(1,4-dioxaspiro[4.5]dec-8-yl)-4-(phenyl)-imidazol-5-yl)-benz imidazole (0.05 g, 0.1 mmol) in 3 N hydrochloric acid (5 mL) for 3 days at room temperature. Add 5 N sodium hydroxide to neutralize the mixture and extract with dichloromethane (3×10 mL). Dry the combined organic phases over sodium sulfate and concentrate under reduced pressure to provide 0.038 g (83%) of the title compound. MS(ES+): m/z=478.2 (M+H)+

EXAMPLE 208

1-isopropylsulfonyl-2-amino-6-(1-(4-hydroxycyclohex-1-yl)-(phenyl)-imidazol-5-yl)-benzimidazole Add a solution of sodium borohydride (0.28 g) in methanol (5 mL) to a solution of 1-isopropylsulfonyl-2-amino-6-(1-(cyclohexan-1-on-4-yl)-4(phenyl)-imidazol-5-yl)-benzimidazole (0.35 g, 0.7 mmol) in 10 mL tetrahydrofuran and 10 mL methanol. Stir the reaction mixture for 30 minutes at room temperature, dilute with water (50 mL), and extract with ethyl acetate (2×15 mL). Wash the combined organic extracts with saturated aqueous sodium chloride, dry over sodium sulfate, and concentrate under reduced pressure to provide 0.345 g (98%) of the title compound. MS(ES+): m/z=480.2 (M+H)+

EXAMPLE 209

1-isopropylsulfonyl-2-amino-6-(1-(4-aminocyclohex-1-yl)-4-(phenyl)-imidazol-5-yl)-benzimidazole hydrochloride Stir a solution of 1-isopropylsulfonyl-2-amino-6-(1-(4-(N-[tert-butoxycarbonyl]amino)cyclohex-1-yl)-4-(phenyl)-imidazol-5-yl)-benzimidazole (0.14 g, 0.2 mmol) in 1 M hydrogen chloride in acetic acid (5 mL) at room temperature for 1 hour. Filter the suspension and dry the solid to provide 0.017 g (15%) of the title compound. MS(ES+): m/z=479.0 (M+H)+

EXAMPLE 210

1-isopropylsulfonyl-2-aminobenzyl-6-(4-(phenyl)-imidazol-5-yl)-benzimidazole

Beginning with 1-isopropylsulfonyl-2-aminobenzyl-6-(α-((tert-butyldimethylsilyl)oxy)-α-(phenyl)acetyl)benzimidazole, prepare the title compound essentially as described in Example 1. Yield 12%. MS(ES$^+$): m/z=472.1 (M+H)$^+$

EXAMPLE 211

2-aminobenzyl-6-(4-(phenyl)-imidazol-5-yl)-benzimidazole

Beginning with 1-isopropylsulfonyl-2-aminobenzyl-6-(4-(phenyl)-imidazol-5-yl)-benzimidazole, prepare the title compound essentially as described in Example 181. Yield: 91%. MS(ES$^+$): m/z=366.1 (M+H)$^+$

EXAMPLES 212 AND 213

1-isopropylsulfonyl-2-aminoethyl-6-(2-(2,6-(difluoro)phenyl)-5-(phenyl)-imidazol-4-yl)-benzimidazole and 2-aminoethyl-6-(2-(2,6-(difluoro)phenyl)-5-(phenyl)-imidazol-4-yl)-benzimidazole Beginning with 1-isopropylsulfonyl-2-aminoethyl-6-(α-((tert-butyldimethylsilyl)oxy)-α-(phenyl)acetyl)benzimidazole, prepare the title compound essentially as described in Example 1. Yield: 42%. MS(ES$^+$): m/z=522.1 (M+H)$^+$. Along with the desired product, a 12% of desulphonylated product 2-aminoethyl-6-(2-(2,6-(difluoro)phenyl)-5-(phenyl)-imidazolyl)-benzimidazole is isolated. MS(ES$^+$): m/z=416.2 (M+H)$^+$

EXAMPLE 214

1-isopropylsulfonyl-6-(1-(4-(methoxy)benzyl)-4-(phenyl)-imidazol-5-yl)-benzimidazole A. 1-isopropylsulfonyl-2-chloro-6-(1-(4-methoxy-benzyl)-4-(phenyl)-imidazol-5-yl)-benzimidazol.

Beginning with 1-isopropylsulfonyl-2-amino-6-(1-(4-methoxy-benzyl)-4-(phenyl)-imidazol-5-yl)-benzimidazole, prepare the title compound essentially as described in Preparation 100. Yield 14%. MS(ES$^+$): m/z=521.2 (M+H)$^+$ B. Reduction To a stirred suspension of the starting 2-chlorobenzimidazole derivative (30 mg, 0.057 mmol, 1 equiv) in 3 mL of MeOH, add Et$_3$N (0.04 mL) dropwise followed by the addition of 10% weight Pd/C catalyst (100 mol %). Purge the suspension with hydrogen for 5 minutes. Stir the mixture under hydrogen atmosphere (1 atm) overnight. Filter the catalyst through a pad of Celite® and rinse several times with EtOAc. Concentrate the solvents in vacuo and purify the residue by silica gel chromatography eluting with 3% CH$_2$Cl$_2$:MeOH to afford the title compound (44% yield). MS(ES): m/z=487.1 (M+H)$^+$

EXAMPLE 215

1-isopropylsulfonyl-2-amino-6-(1-(cyclopropyl)-2-(bromo)-4-(2-fluorophenyl)-imidazol-5-yl)-benzimidazole Add bromine (0.34 mL, 6.545 mmol) dropwise over 5 minutes to a solution of 1-isopropylsulfonyl-2-amino-6-(1-(cyclopropyl)-4-(2-fluorophenyl)-imidazol-5-yl)-benzimidazole (2.61 g, 5.95 mmol) in chloroform (0.7 L) and stir for 18 hours. Wash with water, saturated sodium bicarbonate, dry with magnesium sulfate, filter and remove solvents under reduced pressure. Purify the residue on silica gel eluting with ethyl acetate/dichloromethane mixtures to provide the title compound (2.41 g). MS(ES$^+$): m/z=518.0 (M+H)$^+$

EXAMPLE 216

1-isopropylsulfonyl-2-amino-6-(1-(cyclopropyl)-2-(4-chlorophenyl)-4-(2-fluorophenyl)-imidazol 5-yl)-benzimidazole methanesulfonate Combine 1-isopropylsulfonyl-2-amino-6-(1-(cyclopropyl)-2-(bromo)-4-(2-fluorophenyl)-imidazol-5-yl)-benzimidazole (0.214 g, 0.41 mmol), 4-chlorophenyl boronic acid (0.077 g, 0.50 mmol), tetrakis(triphenylphosphine)-palladium (0.0234 g, 0.021 mmol), 2 M sodium carbonate (0.62 mL), methanol (2.0 mL) and toluene (20 mL) and heat to reflux for 3 hours. Cool to ambient temperature, dilute with ethyl acetate, wash with water saturated sodium carbonate, saturated sodium chloride, dry with magnesium sulfate, filter and remove solvents under reduced pressure. Purify the residue on silica gel eluting with dichloromethane/methanol mixtures to provide 0.196 g of the free base. Treat with methanesulfonic acid as previously described to provide the title compound (0.232 g). MS(ES$^+$): m/z=550.2 (M+H)$^+$

EXAMPLE 217

1-isopropylsulfonyl-2-amino-6-(1-(cyclopropyl)-2-(2,4-difluorophenyl)-4-(2-fluorophenyl))-imidazol-5-yl)-benzimidazole methanesulfonate Beginning with 1-isopropylsulfonyl-2-amino-6-(1-(cyclopropyl)-2-(bromo)-4-(2-fluorophenyl)-imidazol-5-yl)-benzimidazole, prepare the title compound essentially as described in Example 216 (0.179 g). MS(ES$^+$): m/z=552.2 (M+H)$^+$

EXAMPLE 218

1-isopropylsulfonyl-2-amino-6-(1-(cyclopropyl)-2-(trimethylsilylethynyl)-4-(2-fluorophenyl)-imidazol-5-yl)-benzimidazole Combine 1-isopropylsulfonyl-2-amino-6-(1-(cyclopropyl)-2-(bromo)-4-(2-fluorophenyl)-imidazol-5-yl)-benzimidazole (0.332 g, 0.64 mmol), trimethylsilylacetylene (0.36 mL, 2.56 mmol), tetrakis(triphenylphosphine)-palladium (0.150 g, 0.128 mmol), triethylamine (2 mL) and dimethylformamide (4 mL) and heat to 70° C. for 18 hours. Cool to ambient temperature and remove solvents under reduced pressure. Purify the residue on silica gel eluting with acetonitrile/dichloromethane mixtures to provide the title compound (0.295 g). MS(ES+): m/z=536.2 (M+H)+

EXAMPLE 219

1-isopropylsulfonyl-2-amino-6-(1-(cyclopropyl)-(2-but-3-yn-1-ol)-4-(2-fluorophenyl)-imidazol-5-yl)-benzimidazole methanesulfonate Beginning with 1-isopropylsulfonyl-2-amino-6-(1-(cyclopropyl)-2-(bromo)-4-(2-fluorophenyl)-imidazol-5-yl)-benzimidazole, prepare the free base essentially as described in Example 218. Treat with methanesulfonic acid as previously described to provide the title compound (0.096 g). MS(ES+): m/z=508.4 (M+H)+

EXAMPLE 220

1-isopropylsulfonyl-2-amino-6-(1-(cyclopropyl)-2-(ethynyl)(2-fluorophenyl)-imidazol-5-yl)-benzimidazole methanesulfonate Add 1 M tetra-n-butylammonium fluoride (0.15 mL, 0.15 mmol) to a solution of 1-isopropylsulfonyl-2-amino-6-(1-(cyclopropyl)-2-(trimethylsilylethynyl)-4-(2-fluorophenyl))-imidazol-5-yl)-benzimidazole (0.054 g, 0.101 mmol) in tetrahydrofuran (4 mL) and stir for 5 minutes. Dilute with ethyl acetate, wash with water, 50% saturated sodium chloride, dry with magnesium sulfate, filter and remove solvents under redced pressure. Purify the residue on silica gel eluting with hexane/ethyl acetate mixtures to provide the free base (0.037 g). Treat with methanesulfonic acid as previously described to provide the title compound (0.045 g). MS(ES+): m/z=464.1 (M+H)+

EXAMPLE 221

1-isopropylsulfonyl-2-amino-6-(1-(cyclopropyl)-2-(ethyl)$_4$-(2-fluorophenyl)-imidazol-5-yl)-benzimidazole methanesulfonate Add 10% palladium on carbon (0.010 g) to a solution of 1-isopropylsulfonyl-2-amino-6-(1-(cyclopropyl)-2-(ethynyl)-4-(2-fluorophenyl))-imidazol-5-yl)-benzimidazole (0.074 g, 0.16 mmol) in methanol (15 mL) and hydrogenate under 1 atmosphere hydrogen gas for 1.5 hours. Filter and remove solvents under reduced pressure. Purify the residue on silica gel. Treat with methanesulfonic acid as previously described to provide the title compound (0.087 g). MS(ES+): m/z=468.1 (M+H)+

EXAMPLE 222

1-isopropylsulfonyl-2-amino-6-(1-(cyclopropyl)-2-(1,2,3-triazol-4-yl)-4-(2-fluorophenyl)-5-yl)-benzimidazole methanesulfonate Combine 1-isopropylsulfonyl-2-amino-6-(1-(cyclopropyl)-2-(ethynyl)-4-(2-fluorophenyl)-imidazol-5-yl)-benzimidazole (0.114 g, 0.247 mmol), trimethylsilylazide (0.165 mL, 1.23 mmol) and 1,4-dioxane (2 mL) and heat under microwave irradiation at 140° C. for 1 hour. Cool to ambient temperature, add methanol (5 mL) and remove solvents under reduced pressure. Purify the residue on silica gel eluting with dichloromethane/methanol mixtures. Treat with methanesulfonic acid as previously described to provide the title compound (0.088 g). MS(ES+): m/z=507.1 (M+H)+

EXAMPLE 223

1-isopropylsulfonyl-2-amino-6-(1-(cyclopropyl)-2-azido-4-(2-fluorophenyl)-imidazol-5-yl)-benzimidazole Combine 1.9 M phenyllithium (0.42 mL, 0.80 mmol) dropwise to a solution of 1-isopropylsulfonyl-2-amino-6-(1-(cyclopropyl)-2-(bromo)-4-(2-fluorophenyl))-imidazol-5-yl)-benzimidazole(0.103 g, 0.20 mmol) in tetrahydrofuran (3 mL) at −78° C. and stir 20 minutes. Add 1.7 M tert-butyllithium (0.28 mL, 0.48 mmol) dropwise over 5 minutes and stir 60 minutes. Add p-toluenesulfonylazide (0.064 g, 0.323 mmol) in tetrahydrofuran (0.4 mL) dropwise over 2 minutes and stir at −78° C. for 1 hour. Warm to 0° C., dilute with ethyl acetate and wash with saturated sodium chloride. Neutralize aqueous sodium chloride wash with aqueous 1 N hydrochloric acid and back extract with ethyl acetate. Combine organic layers and dry with magnesium sulfate, filter and remove solvents under reduced pressure. Purify the residue on silica gel eluting with acetonitrile/dichloromethane mixtures to provide the title compound (0.035 g). MS(ES+): m/z=481.1 (M+H)+

EXAMPLE 224

1-isopropylsulfonyl-2-amino-6-(1-(cyclopropyl)-2-(amino)-4-(2-fluorophenyl)-imidazol-5-yl)-benzimidazole methanesulfonate Beginning with 1-isopropylsulfonyl-2-amino-6-(1-(cyclopropyl)-2-(nitro)-4-(2-fluorophenyl))-imidazol-5-yl)-benzimidazole prepare the title compound essentially as described in Example 221 (0.031 g). MS(ES+): m/z=455.1 (M+H)+

EXAMPLE 225

1-isopropylsulfonyl-2-amino-6-(1-cyclohexyl-2-(bromo)-4-(2-fluorophenyl))-imidazol-5-yl)-benzimidazole Beginning with 1-isopropylsulfonyl-2-amino-6-(1-(cyclohexyl)-4-(phenyl)-imidazol-5-yl)-benzimidazole, prepare title compound essentially as described in Example 215, MS(ES+): m/z=543.9 (M+H)+

EXAMPLE 226

1-isopropylsulfonyl-2-amino-6-(1-(cyclohexyl)-2-(ethynyl)-4-(phenyl)-imidazol-5-yl)-benzimidazole Beginning with 1-isopropylsulfonyl-2-amino-6-(1-(cyclohexyl)-2-(bromo)-4-(phenyl)-imidazol-5-yl)-benzimidazole, prepare the title compound essentially as described in Examples 218 and 220; MS(ES+): m/z=488.1 (M+H)+

EXAMPLE 227

1-isopropylsulfonyl-2-amino-6-(2-(2,4-difluorophenyl)-5-(3,5-difluorophenyl))-imidazol-4-yl)-benzimidazole Hydrogenate a mixture of 1-isopropylsulfonyl-2-amino-6-(1-(benzyl)-2-(2,4-difluorophenyl)-5-(3,5-difluorophenyl)-imidazol-4-yl)-benzimidazole (0.084 g, 0.778 mmol), palladium black (0.084 g) and methanol (50 mL) at 50° C. with hydrogen gas (55 psi) for 18 hours. Cool the reaction to ambient temperature, filter, and remove the solvent under reduced pressure. Purify the residue on silica gel eluting with dichloromethane/methanol mixtures to provide the title compound (0.025 g). MS(ES$^+$): m/z=530.0 (M+H)$^+$ The free base of Examples 228-231 are prepared essentially as described in Preparation 66-67 and Example 227. The methanesulfonate salts are prepared by dissolving the free base in 10% methanol/dichloromethane, adding 1.0 equivalent methanesulfonic acid and removing the solvents under reduced pressure to provide the methanesulfonate salts.

| Example | Compound | MS(ES$^+$): m/z |
|---|---|---|
| 228 | 1-isopropylsulfonyl-2-amino-6-(2,5-di-(2,4-difluorophenyl)-imidazol-4-yl)-benzimidazole | 530 (M + H)$^+$ |
| 229 | 1-isopropylsulfonyl-2-amino-6-(2-(4-fluorophenyl)-5-(2-methyl-4-fluorophenyl)-imidazol-4-yl)-benzimidazole methanesulfonate | 508.1 (M + H)$^+$ |
| 230 | 1-isopropylsulfonyl-2-amino-6-(2-(4-fluorophenyl)-5-(2-methylphenyl)-imidazol-4-yl)-benzimidazole methanesulfonate | 490.1 (M + H)$^+$ |
| 231 | 1-isopropylsulfonyl-2-amino-6-(2-(4-fluorophenyl)-5-(4-methylphenyl)-imidazol-4-yl)-benzimidazole methanesulfonate | 490.1 (M + H)$^+$ |

The free base of Examples 232-235 are prepared essentially as described in Preparation 67 and Example 227. The methanesulfonate salts are prepared by dissolving the free base in 10% methanol/dichloromethane, adding 1.0 equivalent methanesulfonic acid and removing the solvents under reduced pressure to provide the mono-methanesulfonate salts.

| Example | Compound | MS(ES$^+$): m/z |
|---|---|---|
| 232 | 1-isopropylsulfonyl-2-amino-6-(6-(chloro)-2-(phenyl)-2,3-dihydro-imidazo[1,2-a]pyridin-3-yl)-benzimidazole methanesulfonate | 466.2 (M + H)$^+$ |
| 233 | 1-isopropylsulfonyl-2-amino-6-(7-(methyl)-2-(phenyl)-2,3-dihydro-imidazo[1,2-a]pyridin-3-yl)-benzimidazole methanesulfonate | 446.2 (M + H)$^+$ |
| 234 | 1-isopropylsulfonyl-2-amino-6-(8-(methyl)-2-(4-methoxyphenyl)-2,3-dihydro-imidazo[1,2-a]pyridin-3-yl)-benzimidazole methanesulfonate | 477.0 (M + H)$^+$ |
| 235 | 1-isopropylsulfonyl-2-amino-6-(2-(phenyl)-2,3-dihydro-benzo[d]imidazo[2,1-b]thiazol-3-yl)-benzimidazole methanesulfonate | 488.1 (M + H)$^+$ |

EXAMPLE 236

1-isopropylsulfonyl-2-amino-6-(2-(methyl)-5-(2,4-difluorophenyl)-imidazol-4-yl)-benzimidazole methanesulfonate To a solution of 1-isopropylsulfonyl-2-amino-6-(1-(benzyl)-2-(methyl)-5-(2,4-difluorophenyl)-imidazol-4-yl)-benzimidazole (390 mg, 0.75 mmol) in 100 mL methanol add palladium black (390 mg), and hydrogen gas at 50° C. overnight at 60 psi. The solution is filtered and purified by radial chromatography eluting with 8% methanol in methylene chloride to yield 152 mg (47%) of the title compound as an off-white solid. MS(ES$^+$): m/z=432.0 (M+H)$^+$ To a solution of 1-isopropylsulfonyl-2-amino-6-(2-(methyl)-5-(2,4-difluorophenyl)-imidazolyl-4-yl) -benzimidazole (152 mg, 0.35 mmol) in 5 mL methylene chloride with 3% methanol is added one equivalent of methanesulfonic acid (23 uL) and dried to 186 mg (100%) of the title compound as a tan solid. MS(ES$^+$): m/z=432.0 (M+H)$^+$ The compound of Example 237 may be prepared essentially as described in Example 236.

| Example | Compound | MS(ES$^+$): m/z |
|---|---|---|
| 237 | 1-isopropylsulfonyl-2-amino-6-(2-(methyl)-5-(m-tolyl)-imidazol-4-yl)-benzimidazole-methanesulfonate | 410.0 (M + H)$^+$ |

EXAMPLE 238

1-isopropylsulfonyl-2-amino-6-(3-(methyl)-1-(phenyl)-pyrazol-5-yl)-benzimidazole To a solution of 5-(bromo)-3-(methyl)-1-(phenyl)-pyrazole (264 mg, 1.11 mmol) in 6 mL DME add 1-isopropylsulfonyl-2-amino-benzimidazole-6-boronic acid (694 mg, 2.45 mmol). Add sodium carbonate (354 mg, 3.34 mmol) dissolved in 0.5 mL of water and trans-dichlorobis(triphenylphosphine) palladium (II) (234 mg, 0.33 mmol). Heat the mixture to 100° C. with stirring under nitrogen. After 2 hours, cool and filter over a pad of Celite® and sodium sulfate. Purify the crude product by radial chromatography eluting with 4% methanol in CH$_2$Cl$_2$ to yield 201 mg (46%) of the title compound. MS(ES$^+$): m/z=396.0 (M+H)$^+$ The compounds of Examples 239-240 may be prepared essentially as described in Example 238.

| Example | Compound | MS(ES$^+$): m/z |
|---|---|---|
| 239 | 1-isopropylsulfonyl-2-amino-6-(3-(tert-butyl)-1-(phenyl)-pyrazol-5-yl)-benzimidazole | 438.0 (M + H)$^+$ |
| 240 | 1-isopropylsulfonyl-2-amino-6-(4-(cyano)-1-(phenyl)-pyrazol-5-yl)-benzimidazole | 407.0 (M + H)$^+$ |

EXAMPLE 241

1-isopropylsulfonyl-2-amino-6-(2,4-(diphenyl)-1,2-dihydro-pyrazol-3-on-5-yl)-benzimidazole To a stirred solution of 1-isopropylsulfonyl-2-amino-6-(α-((1-hydroxy)-α-(phenyl)acetyl)-benzimidazole (0.25 mmol, 1 equiv.) in dry toluene (3 mL) add phenylhydrazine (0.27 mmol, 1.1 equiv.) and heat the mixture at reflux under nitrogen followed by TLC. Concentrate the reaction mixture and chromatograph using dichloromethane:methanol 30:1 to give the title compound (24% yield). MS(ACP$^+$): m/z=474.2 (M+H)$^+$ The compound of Examples 242-245 may be prepared essentially as described in Example 241.

| Example | Compound | MS(ACP$^+$): m/z |
|---|---|---|
| 242 | 1-isopropylsulfonyl-2-amino-6-(2-(phenyl)-4-(4-fluorophenyl)-1,2-dihydro-pyrazol-3-on-5-yl)-benzimidazole | 492.1 (M + H)$^+$ |
| 243 | 1-isopropylsulfonyl-2-amino-6-(2-(4-trifluoromethylphenyl)-4(-phenyl)-1,2-dihydro-pyrazol-3-on-5-yl)-benzimidazole | 542.2 (M + H)$^+$ |
| 244 | 1-isopropylsulfonyl-2-amino-6-(2-(2,5-difluorophenyl)-4-(phenyl)-1,2-dihydro-pyrazol-3-on-5-yl)-benzimidazole | 510.2 (M + H)$^+$ |
| 245 | 1-isopropylsulfonyl-2-amino-6-(2-(4-nitrophenyl)-4-(4-fluorophenyl)-1,2-dihydro-pyrazol-3-on-5-yl)-benzimidazole | 537.3 (M + H)$^+$ |

EXAMPLE 246

1-isopropylsulfonyl-2-amino-6-(1-(benzyl)-2-(methyl)-5-(2,4-difluorophenyl)-imidazol-4-yl)-benzimidazole To a solution of 1-(benzyl)-4-(bromo)-5-(2,4-difluorophenyl)-2-(methyl)-imidazole (1.12 g, 3.08 mmol) in 8 mL DME, add 1-isopropylsulfonyl-2-amino-benzimidazole-6-boronic acid (2.62 g, 9.25 mmol). Add sodium carbonate (0.98 g, 9.25 mmol) dissolved in 1 mL of water and trans-dichlorobis(triphenylphosphine) palladium (II) (0.65 g, 0.93 mmol). Heat the mixture to 100° C. with stirring under nitrogen. After 3 hours, cool the solution and filter over a pad of Celite® and sodium sulfate. Purify the residue by radial chromatography eluting with 3% methanol in CH$_2$Cl$_2$ with a gradient to 10% methanol. Perform a second purification by radial chromatography eluting with 4% methanol in CH$_2$Cl$_2$ with a gradient to 6% methanol to yield 390 mg (24%) of the title compound as a yellow solid. MS(ES$^+$): m/z=522.0 (M+H)$^+$

EXAMPLE 247

2-amino-6-(5-phenylimidazol-4-yl)-benzothiazole

Beginning with 2-amino-benzothiazole-6-carboxaldehyde, prepare the title compound essentially as described in Example 182. Yield (16%). MS(ES$^+$): m/z=293.0 (M+H)$^+$

EXAMPLE 248

2-amino-6-(1-(cyclohexyl)-4-(phenyl)-imidazol-5-yl)-benzothiazole

Beginning with 2-amino-benzothiazole-6-carboxaldehyde and cyclohexylamine, prepare the title compound essentially as described in Example 247. Yield (68%). MS(ES$^+$): m/z=375.1 (M+H)$^+$ General Procedure A: Sandmeyer Reaction Add one equivalent of benzothiazole in three portions over 5 minutes to a suspension of one equivalent copper(II) chloride and 1.5 equivalents tert-butylnitrite in 1 mL acetonitrile at 65° C. Add 0.1 mL ethylenediamine, pour the reaction mixture into water, and extract with ethyl acetate (3×25 mL). Wash the combined organic phases sequentially with water (2×15 mL) followed by saturated aqueous sodium chloride (15 mL), dry over sodium sulfate, and concentrate under reduced pressure. Purify the residue by silica gel chromatography, eluting with a gradient of hexane containing from 25-50% ethyl acetate.

EXAMPLE 249

2-chloro-6-(1-(cyclohexyl)-4-(phenyl)-imidazol-5-yl)-benzothiazole

Beginning with 2-amino-6-(1-(cyclohexyl)$_4$-(phenyl)-imidazol-5-yl)-benzothiazole, prepare the title compound essentially as described in the General Procedure A: Sandmeyer Reaction, Yield (24%). MS(ES$^+$): m/z=394.1 (M+H)$^+$

General Procedure B

Add one equivalent of amine to a solution of three equivalents of benzothiazole in 1 mL tetrahydrofuran. After 24 hours concentrate the reaction mixture under reduced pressure. Purify the residue by silica gel chromatography, eluting with hexane containing 25% ethyl acetate.

EXAMPLE 250

2-aminoethyl-6-(1-(cyclohexyl)-4-(phenyl)-imidazol-5-yl)-benzothiazole

Beginning with 2-chloro-6-(1-(cyclohexyl)-4-(phenyl)-imidazol-5-yl)-benzothiazole and ethyl amine, prepare the title compound essentially as described in General Procedure B. MS(ES$^+$): m/z=403.1 (M+H)$^+$

EXAMPLE 251

1-isopropylsulfonyl-2-amino-6-(5-(phenyl)-1,2,3-(triazol-4-yl))-benzimidazole

Combine and stir a mixture of 3-isopropylsulfonamidyl-4-amino-1-(5-phenyl)-1,2,3-triazol-4-yl (0.060 g), lithium methoxide (0.013 g) and cyanogen bromide (0.053 g) in dichloromethane (5 mL) under nitrogen for 48 hours. Purify the residue through an Oasis® HLB extraction cartridge 60 μM(LP) to give a white solid (0.050 g, 30%). MS(ES$^+$): m/z=382.44 (M+H)$^+$

EXAMPLE 252

1-isopropylsulfonyl-2-amino-6-(5-(phenyl)-pyrazol-4-yl)-benzimidazole

Add lithium methoxide (21 mg) and cyanogen bromide (89 mg) to a solution of 3-isopropylsulfonamidyl-4-amino-1-(5-phenyl)-pyrazol-4-yl-phenyl in 4.5 mL of CH$_2$Cl$_2$. Stir under nitrogen for 18 hours. Dilute with 2 mL of THF and 0.25 mL of MeOH to dissolve the solids and wash with 5% NaHCO$_3$. Back extract the aqueous phase with a 9:1 solution of CH$_2$Cl$_2$:MeOH. Separate the phases and dry the organic phase over magnesium sulfate and concentrate under reduced pressure. Subject the residue to silica gel chromatography, eluting with a gradient 2-3.5% CH$_2$Cl$_2$:MeOH to give a white solid (34 mg, 31%). MS(ES$^+$): m/z=382.5 (M+H)$^+$

EXAMPLE 253

1-isopropylsulfonyl-2-amino-6-(2-(2,6-difluorophenyl)-5-(phenyl)-imidazolyl-4-yl)-benzimidazole dimaleate Dissolve 2.50 g (5.0 mmol) in 15 mL of methanol and add 1.20 g (10.0 mmol) of maleic acid. Heat the reaction mixture to 40° C. with stirring for 10 minutes. Filter the reaction mixture. Heat the filtrate to 40-4° C. while adding 35 mL of ethyl acetate. Cool the mixture to room temperature with continued stirring. Product precipitate forms slowly. Collect the solid product by filtration, wash with ethyl acetate, and dry at 50° C. in a vacuum oven, 3.25 g, 92.8%. $^1$H NMR (500 MHz, CD3OD) δ7.75 (m, 1H); 7.62 (s, 1H); 7.54 (d, J=7.0 Hz, 2H); 7.48 (s, 1H); 7.46 (d, J=7.00 Hz, 2H); 7.38 (d, J=7.00 Hz, 1H); 7.38 (dd J=7.00 Hz, 2H); 6.29 (s, 4H); 3.60 (m, 1H); 1.26 (d, J=7.00

The ability of the compounds of the present invention to inhibit p38 kinase is demonstrated by standard assays well known to the skilled artisan, and are briefly described in the following paragraphs.

Inhibition of p38 Kinase

Standard Solution Preparations

The kinase buffer solution is prepared by combining 2.5 mL 1 M Tris-HCl (pH 7.5), 0.1 mL 1 M dithiothreitol, 1.0 mL 1 M magnesium chloride, and 300 μL 1% Triton X-100 and diluting to 100 mL with water. 84 mL of this kinase buffer solution is combined with 16 mL dimethylsulfoxide to prepare the 16% DMSO solution.

The 200 μM ATP solution is prepared by adding 102.6 μL 10 mM aqueous ATP, 25 μL $^{33}$P-ATP, and 163.5 μL of 4 mM aqueous Epidermal Growth Factor Peptide 661-681 (Biomol, Catalog #P-121) in 5 mL kinase buffer solution.

The p38 kinase enzyme solution is prepared by dissolving 9.5 μL concentrated enzyme solution (250 ng p38 enzyme/μL kinase buffer solution) in 1536 μL kinase buffer solution.

Sample Preparation

An 80 μM solution of each test compound and control compound are prepared by dissolving 2 μL of a 10 mM stock solution of the respective compounds in dimethylsulfoxide in 248 μL of the 16% DMSO solution in a Costar 96-well microtiter plate. The plate is placed onto the Tecan Genesis automated liquid handler for 1:3 serial dilutions.

Assay

10 μL of serially diluted compound is placed with a Beckman Multimek 96-well automated liquid handler to the assay plate. 20 μL of 200 μM ATP solution is added with a Titertek Multidrop 8-channel liquid handler. 10 μL of p38 kinase enzyme solution is transferred to the assay plate using the Multimek. The mixture is allowed to react for 40 minutes at 30° C. and then the reaction is stopped by adding 60 μL of freshly prepared 5% glacial acetic acid with Multidrop. 80 μL of this solution is transferred to an "MAPH" plate using the Multimek. The plates are allowed to set for 30 minutes at room temperature and then washed/aspirated on the Titertek MAP extractor with freshly prepared 0.5% glacial acetic acid (1×300 μL, 2×200 μL). The wells are blotted and 100 μL MicroScint-20 scintillation fluid (Packard Bioscience) is added with the Multidrop. The plates are allowed to sit for 30 minutes and counted on a PE/Wallac Microbeta Trilux scintillation counter for $^{33}$P-isotope.

All exemplified compounds were initially tested at 10 concentrations (20 μM-1 nM using 1:3 serial dilutions). Compounds with IC$_{50}$ values less than 25 nM were re-tested at a starting concentration of 2 μM to 0.1 nM (1:3 serial dilutions). IC$_{50}$ values were calculated (IDBS ActivityBase software) for each compound using non-linear regression. All exemplified compounds were tested essentially as described above and were found to inhibit the p38 kinase enzyme with an IC$_{50}$ of at least 5 μM.

Inhibition of TNF-α In Vitro

Mouse Peritoneal Macrophages 1 mL thioglycolate broth (5.0 g yeast extract, 15.0 g casitone or trypticase, 5.0 g dextrose, 2.5 g sodium chloride, 0.75 g L-cystine, 0.5 g sodium thioglycolate, 1.0 mg resazurin, and 0.75 g agar in 1.0 L distilled water) is injected into the peritoneal cavity of each Balb/C female mice. At day 4 or 5 post-injection the mice are sacrificed and then injected i.p. with 4 mL Dulbecco's phosphate-buffered saline (Bio-Whittaker) and the peritoneal macrophages are withdrawn by syringe.

Cytokine Production

Mouse peritoneal macrophages are counted with a hemocytometer and adjusted to $2.5 \times 10^6$ cells/ml complete media (RPMI-1640 medium containing 10% fetal bovine serum). Cells are plated in 96-well flat-bottom plates at $5 \times 10^5$ cells per 200 µl per well and allowed to settle and adhere to the bottom of the well for at least 3 hours. Cells are pre-treated with test compound or standard p38 kinase inhibitor using a series of 8 concentrations for 1 hour at 37° C. (20 µL/well). The cells are then treated with a mixture of 50 ng/L lipopolysaccharide (LPS) and 10 U/mL interferon-γ for 18 hours at 37° C. (20 µL/well). The conditioned media is harvested and assayed for TNF-α production using the Luminex procedure.

TNF-α/Luminex Detection Assay for Inhibition of TNF-α In Vitro (Bio-Rad Bio-Plex Kit—Catalog #171-G12221)

The lyophilized premixed TNF-α standard (1 standard tube/two 96-well plates) is reconstituted with 50 µL sterile water (500,000 pg/mL). The samples are vortexed for 5 seconds, incubated on ice for 30 minutes, and vortexed for 5 seconds before use. A set of twelve 1.5 ml tubes are labeled with #1-thru #12 and then the amounts of cell media shown below added to the appropriate tubes (standard concentrations are as follows: 50,000; 25,000; 12,500; 6,250; 3,125; 1,562.5; 781.3; 390.6; 195.3; 97.7; 48.8; and 24.4 pg/mL). The premixed anti-cytokine conjugated beads are vortexed (25×) vigorously for 30 seconds. The anti-cytokine conjugated beads are diluted to a 1× concentration using 1× Bio-Plex Assay Buffer. For every plate, 240 µL of the pre-mixed beads is added to 5760 µL of Bio-Plex Assay Buffer. A Millipore 96-well filter plate is blocked with 100 µL/well of blocking buffer. The blocking buffer is filtered through using a Millipore filtration system and then toweled dry. Two washes are performed on the filter plate with 100 µl/well of Bio-Plex Assay Buffer and toweled dry. The 1× anti-cytokine conjugated beads are vortexed for 15 seconds and added 50 µL to each well. This is filtered through and toweled dry. Two washes are performed on plates with 100 µl/well of Bio-Plex Wash Buffer. Again, it is filtered through and toweled dry. 50 µL of sample or standard is added to each sample well. This is incubated for 60 seconds at room temperature on a shaker protected from light at setting 6 and then for 30 minutes at setting 3 and then placed in the refrigerator overnight. Three washes are performed with Bio-Plex Wash Buffer, then filtered and toweled dry. The cytokine detection antibody is prepared (~10 minutes prior to use) for every plate and 60 µL of the premixed cytokine detection antibody stock is added to 5940 µL of Bio-Plex Detection Antibody Diluent. 50 µL of cytokine detection antibody is added and incubated for 60 seconds at room temperature on a shaker protected from light at setting 6 and then for 30 minutes at setting 3. Three washes are performed with the Bio-Plex Wash Buffer. This is filtered through and toweled dry. Strept-PE (~10 minutes prior to use) is prepared for every plate and 60 µL to 5940 µL of Bio-Plex Assay Buffer added. 50 µL of Streptavidin-PE is added to each well and incubated for 60 seconds at room temperature on a shaker protected from light at setting 6 and then for 10 minutes at setting 3. Three washes are performed with Bio-Plex Wash Buffer. This is filtered through. The beads are re-suspended in 100 µL/well of Bio-Plex Assay Buffer. Standards and samples are read on a Luminex machine. These intensity readings are then converted to picogram/milliliter units based on a 12-point standard curve created in duplicate using a four-parameter logistic regression method (Bio-Plex Manager, Versions 2.0 and 3.0, Bio-Rad), and the $IC_{50}$ calculated.

The compounds of Examples 1, 6, 16, and 17 were tested essentially as described above and suppressed TNF-α in vitro with an $IC_{50}$ less than 100 nM.

Inhibition of TNF-α In Vivo

Compounds are administered p.o. (100, 30, 10 and 3 mg/kg) to female Balb/c mice (5 mice/dose). After 2 hours, lipopolysaccharide (LPS, *E. coli* serotype 0111:B4, 5 mg/kg) is administered i.v. in the tail vein of each mouse. One hour after LPS administration the mice are euthanized by $CO_2$ inhalation and blood is collected via cardiac puncture. Serum is analyzed for TNF-α levels by Luminex procedure.

TNF-α/Luminex Detection Assay for Inhibition of TNF-α In Vivo (Bio-Rad Bio-Plex Kit—Catalog #171-G12221)

Reconstitute the lyophilized premixed TNF-α standard (1 standard tube/two 96-well plates) with 50 µL sterile water (500,000 pg/mL). Gently vortex for 5 seconds, incubate on ice for 30 minutes, and vortex for 5 seconds before use. Label a set of twelve 1.5 ml tubes with #1-thru #12 and then add the amounts of mouse serum standard diluent shown below to the appropriate tubes (standard concentrations are as follows: 50,000; 25,000; 12,500; 6,250; 3,125; 1,562.5; 781.3; 390.6; 195.3; 97.7; 48.8; and 24.4 pg/mL). Vortex the premixed anti-cytokine conjugated beads (25×) vigorously for 30 seconds. Dilute the anti-cytokine conjugated beads to a 1× concentration using 1× Bio-Plex Assay Buffer. For every plate, add 240 µL of the pre-mixed beads to 5760 µL of Bio-Plex Assay Buffer. Block a Millipore 96-well filter plate with 100 µL/well of blocking buffer. Filter through the blocking buffer using a Millipore filtration system. Towel dry. Perform 2 washes on the filter plate with 100 µl/well of Bio-Plex Assay Buffer and towel dry. Vortex the 1× anti-cytokine conjugated beads for 15 seconds and add 50 µL to each well. Filter through and towel dry. Perform 2 washes on plates with 100 µl/well of Bio-Plex Wash Buffer. Filter through and towel dry. Add 25 µL of serum sample and 25 µL of diluent (Bio-Rad) or 50 µL standard to each sample well. Incubate for 60 seconds at room temperature on a shaker protected from light at setting 6 and then for 30 minutes at setting 3 and then place in the refrigerator overnight. Perform 3 washes with Bio-Plex Wash Buffer.

Filter through and towel dry. Prepare cytokine detection antibody (~10 minutes prior to use) for every plate, add 60 µL of the premixed cytokine detection antibody stock to 5940 µL of Bio-Plex Detection Antibody Diluent. Add 50 µL of cytokine detection antibody and incubate for 60 seconds at room temp on a shaker protected from light at setting 6 and then for 30 minutes at setting 3. Perform 3 washes with Bio-Plex Wash Buffer. Filter through and towel dry. Prepare striped-PE (~10 minutes prior to use) for every plate, add 60 µL to 5940 µL of Bio-Plex Assay Buffer. Add 50 µL of Streptavidin-PE to each well and incubate for 60 seconds at room temp on a shaker protected from light at setting 6 and then for 10 minutes at setting 3. Perform 3 washes with Bio-Plex Wash Buffer. Filter through. Re-suspend the beads in 100 µL/well of Bio-Plex Assay Buffer. Read standards and samples on Lumen machine. These intensity readings are then converted to pictogram/milliliter units based on a 12-point standard curve created in duplicate using a four-parameter logistic regression method (Bio-Plex Manager 2.0, Bio-Rad), and the $IC_{50}$ calculated.

The compounds of Examples 1, 6, and 16 were tested essentially as described above and suppressed TNF-α in vivo with an $IC_{50}$ less than 100 mg/kg.

Effect on Intra-Articular LPS Induced TNF-α

Intra-articular injection of LPS into rat Andes induces the synthesis of TNF-α, which can be measured in synovial lavage fluid. High levels of TNF-α are detectable within 2 hours. Since the joint is the site where arthritis develops, this model can rapidly determine whether an orally administered compound has an effect on an inflammatory response in the synovium.

Six female Lewis rats (150-200 g) are place in each treatment group. The animals are given vehicle (1% NaC-arboxymethylcellulose-0.25% Tween 80) or Example 77 (free base) (1 mg/kg, 3 mg/kg, 10 mg/kg, and 30 mg/kg) orally. One hour later, 10 µl LPS (10 µg) is administered intra-articulately into the right ankle of each rat, while the left ankle receives 10 µL of saline. After two hours, each anode is laved with 100 µL of saline. The lavage is collected and stored at −80° C.
Group#1: Vehicle (1% NaCMC-0.25% Tween 80, 1 mL, PO)
Group#2: Example 77 (free base) (1 mg/kg, 1 mLl, PO)
Group#3: Example 77 (free base) (3 mg/kg, 1 mL, PO)
Group#4: Example 77 (free base) (10 mg/kg, 1 mL, PO)
Group#5: Example 77 (free base) (30 mg/kg, 1 mL, PO)

TNF-α was measured with a commercially available ELISA kit (R&D, RTA00). Treatment with Example 77 produced a dose-dependent inhibition of TNF-α synthesis, as measured in the synovial lavage fluid. The TMED50=10 mg/kg for Example 77 in this assay.

B16F10 Melanoma Target (MAPKAP-K2 Phosphorylation) and B16F10 Melanoma Metastasis Efficacy Model Inhibition of B16F10 Melanoma Lung Metastases The B16F10 melanoma cell line is obtained from the American Type Culture Collection, Rockville, Md. The cells are cultured in RPMI-1640 medium supplemented with 10% fetal calf serum. The cells grown in vitro are harvested during their exponential growth phase by gentle trypsinization, washed twice in medium, and resuspended in serum-free RPMI-1640 medium. The number of monodisperse viable cells is determined using a hemocytometer and adjusted to $1 \times 10^6$ cells/mL. Tumor cells are injected intravenously into the tail vein of normal C57B16 mice with an inoculum volume of 0.2 ml containing 200,000 cells. Mice are treated with test compound or vehicle control starting 1 day before i.v. tumor inoculation. Example 77 (free base) is prepared as a suspension formulation in 1% NaCMC/0.25% polysorbate 80 and probe sonicated in an injection volume of 1% body weight (e.g., the 30 mg/kg dose level is prepared at 3 mg/ml and 0.2 cc was administered per 20 gram mouse). Mice are treated orally tid. with the compound at 30, 10, and 3 mg/kg (90, 30, and 9 mg/kg/day) from days −1 through 16 after tumor cell inoculation. Control mice receive the vehicle alone in an identical manner. On day 16, the mice are sacrificed, and the lungs are harvested and fixed in 3% paraformaldehyde. Lung lesions are quantitated by manual counting under a dissecting microscope.

The test compound was tested in the B16F10 melanoma lung metastasis model orally at 3, 10, and 30 mg/kg, tid from one day before to 16 days after i.v. tumor inoculation (total dose 9, 30 and 90 mg/kg/day). The lungs were harvested on day 16 and lung lesions were quantitated. The test compound caused 54%, 73%, and 95% inhibition of lung metastasis formation for the 3, 10 and 30 mg/kg dose levels, respectively (p<0.001 at all three dose levels).

B16F10 Target (phosphorylated MAPKAPK-2) Studies.

The B16F10 melanoma cell line is obtained from the American Type Culture Collection, Rockville, Md. The cells are cultured in RPMI-1640 medium supplemented with 10% fetal calf serum. The cells grown in vitro are harvested during their exponential growth phase by gentle trypsinization, washed twice in medium, and resuspended in serum-free RPMI-1640 medium. The number of viable cells is determined using a hemocytometer and adjusted to $1 \times 10^7$/mL. Tumor cells are injected subcutaneously in normal C57B16 mice. Inoculum volume per mouse is 0.2 mL (2,000,000 cells). When the tumors reach 300-500 mg, the mice are used for target inhibition studies at either a fixed time (2.5 hours) after p.o. compound treatment or pharmacodynamic studies where the tumors are collected at multiple time-points (e.g., 3, 6, 9, 12, 15, and 18 hours) after p.o. compound treatment.

Protein Extraction and Immuno-Blot Analysis

Tumors collected as described above are immediately snap-frozen in liquid nitrogen and stored at −80° C. Tumor tissues are homogenized on ice using a Daunce homogogenizer in an extraction buffer (25 mM Tris pH 7.5 containing the following protease inhibitors: 10 µg/ml leupeptin, 10 µg/mL soybean tryp-chymotrypsin inhibitor, 10 µg/mL N-tosyl-L-phenylalanine chloromethyl ketone, 10 µg/ml aprotinin, Na-p-tosyl-L-arginine methyl ester, 7 mM benzamidine, 0.3 mM phenylmethylsulfonyl fluoride and two tablets of Roche complete protease inhibitor cocktail; following phosphatase inhibitors: 60 mM beta-glycerophosphate, 1 mM sodium vanadate, 10 mM sodium fluoride. 20 mM p-nitrophenyl phosphate, 1 µM okadaic acid, 1 µM microcystin, 2.5 mM sodium pyrophoate; and 1 mM dithiothreitol, 15 mM EDTA, 5 mM EGTA, 1% Triton X100 and 150 mM sodium chloride). Tissue lysates are cleared by centrifugation in a refrigerated microcentrifuge at 14,000 rpm and at 1° C. for 20 minutes. Supernatants are transferred to fresh microfuge tubes prechilled on ice and snap-freeze again in liquid nitrogen or dry ice. After quick thaw to about 80% completion in lukewarm water, the samples are placed on ice to complete thaw. The samples are centrifuged again at 14,000 rpm and at 1° C. for 15 minutes. The supernatant is transferred to fresh prechilled microfuge tubes and protein concentrations are measured using Bio-Rad protein assay reagents using bovine serum albumin as protein standard.

Protein extracts are equalized with the extraction buffer. An equal volume of 2×SDS sample buffer is added to the protein extracts and boiled in a waterbath for 5 minutes. 100 μg of protein extract per sample is used for electrophoresis on 4-20% gradient SDS-PAGE gel and transferred onto nitrocellulose (NC) membranes. NC membranes are blocked in 5% BSA in TBST (20 mM Tris pH7.5, 500 mM sodium chloride, 0.05% Tween 20 and 0.02% sodium azide) for least 1 hour. The membranes are then incubated in primary antibody at 1:1,000 with 5% BSA in TBST overnight on a shaker with 80 rpm at 4° C. Membranes are washed 4×, 10 minutes each, with TBST. The membranes are then incubated for 40 minutes with secondary antibody HRP (horse radish peroxidase) conjugate at 1:10,000 dilution in 3% non-fat milk in TBST and washed again 4 times with TBST, 10 minutes each. The immuno-blots are then visualized by enhanced chemiluminescence (ECL, Amersham) as per manufacturer's instructions. All primary antibodies are purchased from Cell Signaling and secondary antibody HRP conjugates are obtained from Amersham. Gels, membranes and apparatus used for electrophoresis and Western blotting are purchased from Invitrogen. Protein bands of interest are quantified from films using Kodak Image Station 1000.

The compound of Example 77 showed excellent dose-dependent activities against p38 MAPK in tumors harvested 2.5 hours after dosing, seen as a dose-dependent inhibition of MAPKAPK-2 phosphorylation. MAPKAPK-2 is a physiological substrate of p38 MAPK. Appreciable inhibition of MAPKAPK-2 phosphorylation by the compound of Example 77 was observed at doses as low as 0.3 mg/kg and ANOVA TMED50 was determined at 3 mg/kg. The compound of Example 77 at doses >30 mg/kg reduced the phosphorylation level of MAPKAPK-2 in the tumors by >80% (P<0.001). In the time course study, the compound of Example 77 was administered at 30 mg/kg and tumors were excised at various time intervals after dosing for up to 18 hours. Western blotting analysis of MAPKAPK-2 phosphorylation showed that the compound of Example 77 inhibited p38 MAPK activity for up to 9 hours. By 12 hours after dosing, the level of MAPKAPK-2 phosphorylation in the treated tumors returned to a similar level as in the vehicle control.

The compound of Example 77 was tested in the B16F10 melanoma lung metastasis model orally at 3, 10, and 30 mg/kg, tid from one day before to 16 days after i.v. tumor inoculation (total dose 9, 30 and 90 mg/kg/day). The lungs were harvested on day 16 and lung lesions were quantitated. The compound of Example 77 caused 54%, 73%, and 95% inhibition of lung metastasis formation for the 3, 10 and 30 mg/kg dose levels, respectively (p<0.001 at all three dose levels).

P815 Tumor Model

Female(6-8 weeks old) DBA/2 mice (Taconic) are implanted subcutaneously into the hind flank region on day 0 with P815 cells (0.5×10$^6$ cells in 200 ul of RPMI 1640). P815 tumor cells are purchased from ATCC and are cultured in RPMI 1640 medium, supplemented with glutamine and 10% bovine serum at 37° C. in 5% $CO_2$ cell culture incubator. Tumor-bearing animals are treated with oral administration of Example 77 (free base), at different doses or vehicle with frequency of three times a day started on the day of implantation. Tumor growth is monitored every 2 days by measuring perpendicular diameters. Tumor volume expressed in milligram (mg) is determined as the product of the largest diameter (a) and its perpendicular (b) according to the formula [tumor volume=a×b$^2$×0.536].

In Vivo Target Inhibition Study in P815 Mastocytoma Model

In vivo target inhibition is determined by measuring the effect of inhibitor treatment on the phosphorylation of MAPKAP-K2 expressed in P815 tumor tissues. Tumors in DBA/2 mice received P815 cells subcutaneous implantation are allowed to grow to a size of 300-500 mg without treatment. Tumor bearing mice are then given oral administration of Example 77 (free base) or vehicle. To investigate time course related target inhibition by Example 77 (free base), tumors are harvested from $CO_2$ sacrificed animals at the indicated times (3 hours, 6 hours, 12 hours, and 18 hours) after compound is dosed at 30 mg/kg. Dose-dependent target inhibition by Example 77 (free base) is investigated by harvesting tumors at 3 hours after orally given different doses of Example 77 (free base) or vehicle. Harvested tumors are immediately snap frozen onto dry ice, pulverized, homogenized and lysed in cooled lysis buffer containing proteinase and phosphatase inhibitors. After centrifugation to remove cell debris, supernatants containing 100 microgram total proteins are resuspended in 2×Tris-Glycin loading buffer and subjected to sodium dodecyl sulfate-polyacrylamide gel electrophoresis (10% Tris-Glycine) under reducing conditions. Proteins are subsequently blotted onto a PDVF membrane and were then blocked in 5% milk PBS containing 0.1% Tween-20 for 1 hour at room temperature. The membrane is then incubated with primary antibody (anti-phospho-MAPKAP-K2, Cell Signaling) at 4° C. overnight followed by incubation with secondary antibody (anti-rabbit HRP-conjugated IgG) at room temperature 1 hour. Phospho-MAPKAP-K2 expression level is visualized by Phospho-Image detection system after the enhanced chemiluminescence (ECL) detection is used to reflect the presence of proteins on the PVDF blots. Expression level of phospho-p38 MAP kinase and total p-38 MAP kinase is also monitored by similar western blotting procedure.

Time- and Dose-Dependent Inhibition of MAPKAP-K2 Phosphorylation by Example 77 (Free Base) in P815 Tumors In Vivo The effect of oral administration of a single dose of Example 77 (free base) on MAPKAP-K2 phosphorylation was evaluated in DBA/2 mice bearing P815 tumors. Administration of Example 77 (free base) at 30 mg/kg caused a time-dependent inhibition of MAPKAP-K2 phosphorylation. This inhibitory effect of the compound happened as early as 3 hours after animals are dosed and extended to 12 hours. It was also evident that phosphorylation of MAPKAP-K2 recovered completely at 18 hours after dosing. When P815 tumor bearing animals were given Example 77 (free base) at different doses (3, 10 and 30 mg/kg) and their tumors were harvested for measuring protein expression at 3 hours after dosing, a significant dose-dependent inhibition of MAPKAP-K2 phosphorylation was demonstrated. In these animal studies Example 77 (free base) did not alter both p38 MAP kinase phosphorylation and total p38 MAP kinase expression in vivo.

Inhibition of P815 Tumor Growth In Vivo

The in vivo activity of Example 77 (free base) was assessed on the growth of P815 tumors grafted subcutaneously in DBA/2 mice. Oral administration of Example 77 (free base) at tid doses between 0.1 and 30 mg/kg resulted in dose-dependent inhibition of P815 tumor growth, with 67% inhibition of tumor volume at 30 mg/kg ($p<0.01$, three independent studies), 55% inhibition at 3 mg/kg ($p<0.05$, 2 independent studies), and 30 to 14% inhibition at lower doses.

Rat Collagen Induced Arthritis Efficacy Model

Female Lewis rats (($\approx$190 gm, Charles River Labs) are immunized with Bovine type II collagen (2 mg/ml) emulsified with an equal volume of adjuvant (aluminum hydroxide). were used. The rats are immunized with approximately 0.3 mg of the emulsion intradermally on the back near the base of the tail. All animals are re-immunized 7 days later according to the same protocol. The rats begin to develop arthritis (characterized by swelling and redness of one or both ankles) from 12 to 14 days after the first immunization. The rats are equally distributed into five treatment groups at the first signs of arthritis and treatment is initiated with each rat dosed bid for 14 days.

Treatment Groups:
Group 1 Vehicle (1% NaCarboxymethylcellulose+0.25% Tween 80) 1 mL, PO, Bid×14 days
Group 2 Example 77 (free base), 5 mg/kg, 1 mL, PO, Bid×14
Group 3 Example 77 (free base), 15 mg/kg, 1 mL, PO, Bid×14
Group 4 Example 77 (free base), 30 mg/kg, 1 mL, PO, Bid×14
Group 5 Prednisolone 10 mg/kg, 1 mL, PO, qd×14

Ankle diameter is measured with calipers 5 days a week and recorded. Data is expressed as the area under the curve (AUC) generated from the composite inflammation scores and statistical analysis performed. At all doses of Example 77 there was a significant reduction in ankle diameter with a maximum reduction of 46% at 30 mg/kg ($p<0.0001$). Prednisolone reduced the inflammation to pre-arthritic levels.

At the termination of the study, animals were sacrificed and ankles processed for histological evaluation. The histology score is based on a 0-5 scale for each of 4 parameters Inflammation, pannus, cartilage damage, bone resorption). In animals treated with Example 77, a dose dependent inhibition of joint pathology was observed. Significant reduction in overall joint scores was obtained in animals treated with Example 77 at 15 and 30 mg/kg ($p<0.03$ and $p=0.0031$ respectively).

Oral administration of the compounds of the present invention is preferred. However, oral administration is not the only route or even the only preferred route. For example, transdermal administration may be very desirable for patients who are forgetful or petulant about taking oral medicine, and the intravenous route may be preferred as a matter of convenience or to avoid potential complications related to oral administration. Compounds of Formula I may also be administered by the percutaneous, intramuscular, intranasal or intrarectal route in particular circumstances. The route of administration may be varied in any way, limited by the physical properties of the drugs, the convenience of the patient and the caregiver, and other relevant circumstances (*Remington's Pharmaceutical Sciences*, 18th Edition, Mack Publishing Co. (1990)).

The pharmaceutical compositions are prepared in a manner well known in the pharmaceutical art. The carrier or excipient may be a solid, semi-solid, or liquid material that can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

The compounds of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations of the present invention may be determined by methods well known to the skilled artisan.

The tablets, pills, capsules, troches, and the like may also contain one or more of the following adjuvants: binders such as povidone, hydroxypropyl cellulose, microcrystalline cellulose, or gelatin; excipients or diluents such as: starch, lactose, microcrystalline cellulose or dicalcium phosphate, disintegrating agents such as: croscarmellose, crospovidone, sodium starch glycolate, corn starch and the like; lubricants such as: magnesium stearate, stearic acid, talc or hydrogenated vegetable oil; glidants such as colloidal silicon dioxide; wetting agents such as: sodium lauryl sulfate and polysorbate 80; and sweetening agents such as: sucrose, aspartame or saccharin may be added or a flavoring agent such as: peppermint, methyl salicylate or orange flavoring.

When the dosage unit form is a capsule, it may contain, in addition to materials of the above type, a liquid carrier such as polyethylene glycol or a fatty oil. Other dosage unit forms may contain other various materials that modify the physical form of the dosage unit, for example, as coatings. Thus, tablets or pills may be coated with sugar, hydroxypropyl methylcellulose, polymethacrylates, or other coating agents. Syrups may contain, in addition to the present compounds, sucrose as a sweetening agent and certain preservatives, dyes and colorings and flavors. Materials used in preparing these various compositions should be pharmaceutically pure and non-toxic in the amounts used.

The compounds of Formula I are generally effective over a wide dosage range. For example, dosages per day normally fall within the range of about 0.0001 to about 30 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

We claim:

1. A compound of Formula I:

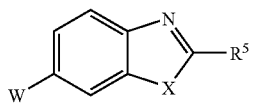

I

Where:

W is:

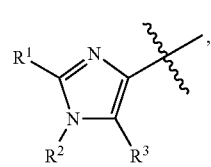

(i)

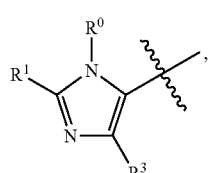

(ii)

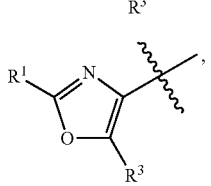

(iii)

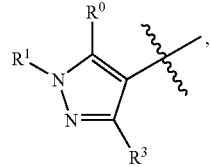

(iv)

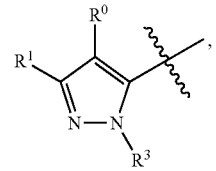

(v)

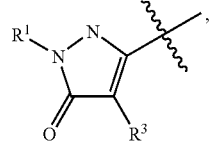

(vi)

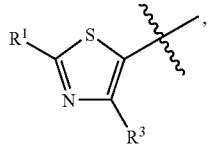

(vii)

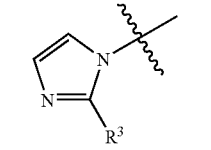

(viii)

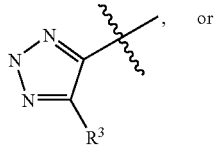

(ix)

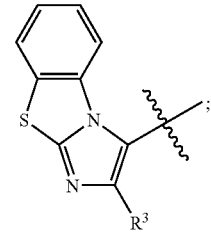

(x)

X is $N(R^4)$ or S;

$R^0$ is (a) selected from the group consisting of hydrogen, $C_1$-$C_6$ alkyl, cyano, ($C_1$-$C_4$ alkylene)-$R^{11}$, 3-hydroxyprop-2-yl, (1-phenyl)-2-hydroxyeth-1-yl, (1-cyclohexyl)-3-hydroxyprop-2-yl, 4-methoxybenzyl, 1,4-dioxoaspiro[4,5]dec-8-yl, tetrahydropyran, 2,2,6,6-tetramethylpiperidin-4-yl, and cyclohexan-1-on-4-yl, (b) phenyl optionally substituted with one substituent selected from the group consisting of nitro and amino, (c) piperidin-4-yl optionally substituted with one substituent selected from the group consisting of $C_1$-$C_4$ alkyl, $C_1$-$C_4$ alkoxycarbonyl, and benzyl, or (d) $C_3$-$C_6$ cycloalkyl optionally substituted with one substituent selected from the group consisting of $C_1$-$C_4$ alkoxycarbonylamino, amino, hydroxy, and $C_1$-$C_4$ alkylene-OH;

$R^1$ is (a) selected from the group consisting of hydrogen, $C_1$-$C_6$ alkyl, $C_2$-$C_4$ alkynyl, halo, amino, azido, formyl, 1-($C_1$-$C_4$ alkoxycarbonyl)ethen-2-yl, 1-($C_1$-$C_4$ alkoxycarbonyl)ethyl, 1-($C_1$-$C_4$ carboxy)ethyl, ($C_1$-$C_4$ alkylene)benzyloxy, trifluoromethyl, trimethylsilylethynyl, but-3-yn-1-ol, , $C_3$-$C_6$ cycloalkyl, tetrahydropyran-4-yl, hydroxymethyl, 2-(piperidin-1-yl)methyl, N,N',N'-[trimethyl]-2-(aminoethylamino) methyl, (morpholin-4-yl)methyl, dimethylaminomethyl, N-[2-(piperidin-1-yl)eth-1-yl]-aminomethyl, N',N'-dimethyl-2-(aminoethylamino)methyl, pyridinyl, thiazolyl, triazolyl, benzo (1,3)dioxolan-5-yl, and imidazol-2-yl, (b) phenyl optionally substituted with one to three substituents independently selected from the group consisting of $C_1$-$C_4$ alkyl, halo, nitro, amino, $C_1$-$C_4$ alkoxy, trifluoromethyl, trifluoromethoxy, trifluoromethylsulfanyl, methylsulfonyl, methylsulfonamidyl, pyrrolidin-1-yl, morpholin-4-yl, 4-($C_1$-$C_4$ alkyl)piperazin-1-yl, —NR$^6$R$^7$, and $C_1$-$C_4$ alkoxy optionally substituted with one substituent selected from the group consisting of piperidin-1-yl, pyrrolidin-1-yl, morpholin-4-yl, azepin-4-yl, and di($C_1$-$C_4$ alkyl)amino, (c) thienyl optionally substituted with one substituent selected from the group consisting of halo, nitro, amino, and $C_1$-$C_4$ alkyl, or (d) piperidin-4-yl optionally substituted at the 1-position from the group consisting of $C_1$-$C_4$ alkyl, $C_1$-$C_4$ alkoxycarbonyl, benzyloxycarbonyl, and ($C_1$-$C_4$ alkylene)-R$^8$;

Alternatively $R^0$ and $R^1$ may be taken together to form a fully saturated $C_3$-$C_4$ carbon chain or a fully unsaturated $C_3$-$C_4$ carbon chain optionally substituted with halo or $C_1$-$C_4$ alkyl;

$R^2$ is hydrogen, $C_1$-$C_4$ alkyl, or benzyl;

$R^3$ is thienyl or phenyl optionally substituted with one to two substituents independently selected from the group consisting of halo, $C_1$-$C_4$ alkyl, $C_1$-$C_4$ alkoxy, and trifluoromethyl;

$R^4$ is ($C_1$-$C_4$ alkyl)sulfonyl, ($C_3$-$C_6$ cycloalkyl)sulfonyl, or ($C_1$-$C_4$ alkyl)$_2$N-sulfonyl;

$R^5$ is halo, hydrogen, or —NR$^9$R$^{10}$;

$R^6$ and $R^7$ are individually at each occurrence selected from hydrogen, carbonyl, or $C_1$-$C_4$ alkyl providing that at least one of $R^6$ and $R^7$ is hydrogen;

$R^8$ is hydroxy, trifluoromethyl, dimethylamino, phenyl, pyridinyl, or 1-methylimidazol-2-yl,;

$R^9$ is independently at each instance hydrogen or $C_1$-$C_4$ alkyl;

$R^{10}$ is hydrogen, $C_1$-$C_4$ alkyl, or benzyl;

$R^{11}$ is $C_1$-$C_4$ alkoxy, hydroxy, $C_1$-$C_4$ alkoxycarbonyl, $C_1$-$C_4$ alkoxycarbonylamino, $C_3$-$C_6$ cycloalkyl, phenyl optionally substituted with one to two substituents independently selected from the group consisting of $C_1$-$C_4$ alkoxy and halo, morpholin-4-yl, or pyridinyl;

provided that when W is

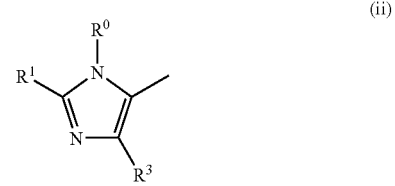

then (a) at least one of $R^0$ and $R^1$ is hydrogen or $C_1$-$C_6$ alkyl; or (b) $R^0$ and $R^1$ may be taken together to form a fully saturated $C_3$-$C_4$ carbon chain or a fully unsaturated $C_3$-$C_4$ carbon chain optionally substituted with halo or $C_1$-$C_4$ alkyl;

also provided that when X is S, W is

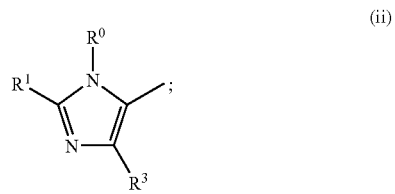

or a pharmaceutically acceptable salt or a pharmaceutically acceptable solvate thereof.

2. A compound of claim 1, where W is either

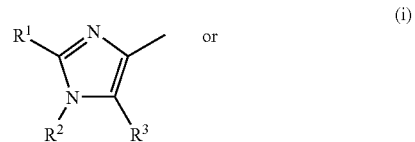

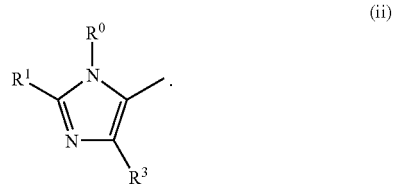

3. A compound of claim 1, which is 1-isopropylsulfonyl-2-amino-6-(2-(2,6-difluorophenyl)-5-(phenyl)-imidazol-4-yl)-benzimidazole or a pharmaceutically acceptable salt or a pharmaceutically acceptable solvate thereof.

4. A pharmaceutical formulation comprising a compound of claim 1 and a pharmaceutically acceptable carrier, diluent, or excipient.

5. A compound of claim 2, where X is NR$^4$ and $R^4$ is ($C_1$-$C_4$alky)sulfonyl.

6. A compound of claim 5, where $R^4$ is (isopropyl)sulfonyl and $R^5$ is —$NH_2$.

7. A compound of claim 5, where $R^4$ is (tert-butyl)sulfonyl and $R^5$ —$NH_2$.

8. A compound of claim 7, where $R^1$ is tert-butyl.

9. A method of inhibiting lung melanoma metastasis comprising administering to a mammal in need of such treatment a p38 inhibiting amount of a compound of claim 1.

* * * * *